United States Patent
Deprez et al.

(10) Patent No.: US 11,053,204 B2
(45) Date of Patent: Jul. 6, 2021

(54) PYRIMIDINYLOXY BENZENE DERIVATIVES AS HERBICIDES

(71) Applicant: FMC Corporation, Philadelphia, PA (US)

(72) Inventors: Nicholas Ryan Deprez, East Windsor, NJ (US); John Robbins Debergh, Middletown, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 15/556,476

(22) PCT Filed: Jun. 1, 2016

(86) PCT No.: PCT/US2016/035229
§ 371 (c)(1),
(2) Date: Sep. 7, 2017

(87) PCT Pub. No.: WO2016/196606
PCT Pub. Date: Dec. 8, 2016

(65) Prior Publication Data
US 2018/0105501 A1 Apr. 19, 2018

Related U.S. Application Data

(60) Provisional application No. 62/171,294, filed on Jun. 5, 2015.

(51) Int. Cl.
C07D 239/34 (2006.01)
A01N 43/54 (2006.01)

(52) U.S. Cl.
CPC .......... *C07D 239/34* (2013.01); *A01N 43/54* (2013.01); *A01N 2300/00* (2013.01)

(58) Field of Classification Search
CPC ... C07D 239/34; A01N 43/54; A01N 2300/00
See application file for complete search history.

(56) References Cited

U.S. PATENT DOCUMENTS

| | | | |
|---|---|---|---|
| 2,891,855 A | 6/1959 | Hans et al. | |
| 3,013,054 A | 12/1961 | Richter | |
| 4,248,619 A | 2/1981 | Serban et al. | |
| 4,371,736 A | 2/1983 | Selby | |
| 4,423,047 A | 12/1983 | Benneche et al. | |
| 4,427,437 A | 1/1984 | Serban et al. | |
| 4,460,588 A | 7/1984 | Serban et al. | |
| 4,634,649 A | 1/1987 | Knapp | |
| 4,863,924 A | 9/1989 | Haga et al. | |
| 4,871,387 A * | 10/1989 | Sasse ................... | A01N 43/40 504/223 |
| 4,889,552 A | 12/1989 | Wada et al. | |
| 5,962,685 A | 10/1999 | Ueda et al. | |
| 6,268,310 B1 | 7/2001 | Ueda et al. | |
| 7,642,264 B2 | 1/2010 | Gatti McArthur et al. | |
| 7,786,044 B2 | 8/2010 | Epp et al. | |
| 8,431,607 B2 | 4/2013 | Liu et al. | |
| 9,567,318 B2 | 2/2017 | Chiosis et al. | |
| 9,695,155 B2 | 7/2017 | Sharpe et al. | |
| 9,963,442 B2 | 5/2018 | Satterfield | |
| 10,131,652 B2 | 11/2018 | Deprez et al. | |
| 10,485,235 B2 | 11/2019 | Stevenson et al. | |
| 10,654,840 B2 | 5/2020 | Deprez et al. | |
| 2009/0221547 A1 | 9/2009 | Gao et al. | |
| 2009/0291971 A1 * | 11/2009 | Mansour ............. | C07D 239/88 514/260.1 |
| 2010/0022538 A1 | 1/2010 | Boebel et al. | |

(Continued)

FOREIGN PATENT DOCUMENTS

| | | |
|---|---|---|
| AU | 3916678 | 1/1981 |
| AU | 7839166 A | 1/1981 |

(Continued)

OTHER PUBLICATIONS

Saito, Yoshihiro et al. "Preparation of pyrimidine derivatives as herbicides". XP002735697, retrieved from STN Database accession No. 1992:545339 abstract, CAS-RN 143437-16-5.
Selby et al., "N-Azolyl Phenoxypyrimidine Herbicides: Novel Inhibitors of Carotenoid Biosynthesis Part 1,"Water-Soluble Polymers: Synthesis, Solution Properties and Applications, vol. 800, Jan. 1, 2002 (Jan. 1, 2002), pp. 74-84, XP001120637, ISBN: 978-0-541-23408-9.
Hiroshi Okada et al., "Synthesis and Antitumor Activities of Novel Benzoylphenylurea Derivatives", Chemical and Pharmaceutical Bulletin, vol. 39, No. 9, 1991, pp. 2308-2315, XP001205628, ISSN: 0009-2363.
PCT International Search Report for WO2016/196606, dated Aug. 5, 2016.

(Continued)

*Primary Examiner* — John Pak
*Assistant Examiner* — Andriae M Holt
(74) *Attorney, Agent, or Firm* — FMC Corporation; Reed A Coats

(57) ABSTRACT

Disclosed are compounds of Formula 1, including all stereoisomers, N-oxides, and salts thereof,

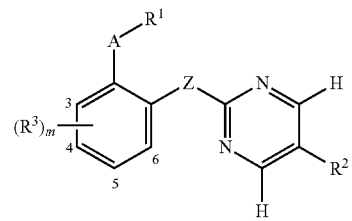

wherein
A, Z, $R^1$ $R^2$, $R^3$ and m are as defined in the disclosure. Also disclosed are compositions containing the compounds of Formula 1 and methods for controlling undesired vegetation comprising contacting the undesired vegetation or its environment with an effective amount of a compound or a composition of the invention.

16 Claims, No Drawings

(56) References Cited

U.S. PATENT DOCUMENTS

| | | |
|---|---|---|
| 2012/0252818 A1 | 10/2012 | Chiosis et al. |
| 2016/0333000 A1 | 11/2016 | Deprez et al. |
| 2017/0190671 A1 | 7/2017 | Reddy et al. |
| 2017/0204081 A1 | 7/2017 | Satterfield |
| 2018/0020664 A1 | 1/2018 | Reddy et al. |
| 2018/0206497 A1 | 7/2018 | Stevenson et al. |
| 2020/0055826 A1 | 2/2020 | Dao et al. |

FOREIGN PATENT DOCUMENTS

| | | |
|---|---|---|
| AU | 535637 B2 | 3/1984 |
| CA | 2290379 A1 | 11/1998 |
| CN | 86108213 | 7/1987 |
| CN | 1743319 | 3/2006 |
| CN | 101367766 | 2/2009 |
| DE | 4438824 A1 | 4/1995 |
| EP | 0001187 A1 | 3/1979 |
| EP | 008192 | 2/1980 |
| EP | 0008192 A1 | 2/1980 |
| EP | 0410590 A1 | 1/1991 |
| EP | 0226104 B1 | 2/1991 |
| EP | 0665224 A1 | 8/1995 |
| GB | 2237570 B | 5/1993 |
| JP | 54117486 | 9/1979 |
| JP | S61236766 A | 10/1986 |
| JP | H4108777 A | 4/1992 |
| JP | 10251255 A | 9/1998 |
| JP | 2012012299 A | 1/2012 |
| JP | 5753178 B2 | 7/2015 |
| WO | 8400685 A1 | 3/1984 |
| WO | 9417059 A1 | 8/1994 |
| WO | 199603399 | 2/1996 |
| WO | 9633994 | 10/1996 |
| WO | 9633994 A1 | 10/1996 |
| WO | 9840379 A1 | 9/1998 |
| WO | 9852938 A1 | 11/1998 |
| WO | 20070095602 | 8/2007 |
| WO | 20080009963 | 1/2008 |
| WO | 2012039141 A1 | 3/2012 |
| WO | 2012076877 | 6/2012 |
| WO | 2015108779 A1 | 7/2015 |

OTHER PUBLICATIONS

US Registry, Columbus, OH, Registry 1708459-71-5, 1467117-33-4, 1410198-95-6, 1406953-26-1, 1406953-21-6, 1405334-69-1, 1341743-06-3, 1303451-33-3, 1275377-53-1, 1770715-88-2, 1713091-81-6, 1713090-70-0, 1712816-03-9, 1712628-58-4, 1711920-35-2, 1711592-73-2, 1711248-57-5, 1711124-76-3, 1563425-59-1, 1562695-66-2, 1562580-07-7, 1561249-97-5, 1561237-35-1, 1549277-09-9, 1545632-35-6, 1541703-38-1, 1497265-38-9, 1493273-89-4, 1493019-06-9, 1489928-78-0, 1484372-21-5, 1484221-73-9, 1478489-93-8, 1477982-24-3, 1477796-60-3, 1467306-53-1, 1411677-38-7, 1411677-31-0, 1409911-18-7, 1409911-04-1, 1408627-48-4, 1406966-19-5, 1406966-13-9, 1406755-88-1, 1405689-57-7, 1405334-66-8, 1405028-95-6, 1308732-13-9, 1293192-07-0, 1293143-24-4, 1276193-73-7, 1276077-63-4, 1275449-10-9, Jun. 1, 2015.

US Registry, Columbus, OH, Registry, 887431-94-9, Jun. 12, 2006.

Li Yuanxiang, "Study of synthesis and herbicidal activity of novel 4,6-dimethoxypyrimidine derivatives", Chinese Doctoral Dissertations Full-text Database?Engineering Science And Technology Series I, No. 9, Sep. 15, 2009.

Hiroshi Okada et al., "Synthesis and Antitumor Activities of Novel Benzoylphenylurea Derivatives", Chemical and Pharmaceutical Bulletin, vol. 39, No. 9, 1991, pp. 2308-2315 XP001205268, ISSN: 0009-2363.

* cited by examiner

PYRIMIDINYLOXY BENZENE DERIVATIVES AS HERBICIDES

CROSS-REFERENCE TO RELATED APPLICATIONS

This application is a continuation of International Application No. PCT/US2016/035229, filed on Jun. 1, 2016, which claims priority to U.S. Provisional Application No. 62/171,294, filed on Jun. 5, 2015, both of which are incorporated by reference in their entirety herein.

FIELD OF THE INVENTION

This invention relates to certain pyrimidinyloxy benzene derivatives, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1 (including all geometric and stereoisomers), N-oxides, and salts thereof, agricultural compositions containing them and their use as herbicides:

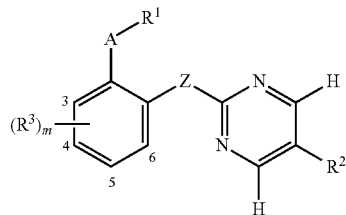

1 wherein
A is;

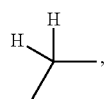

A-1

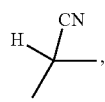

A-2

A-3

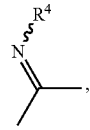

A-4

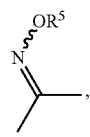

A-5

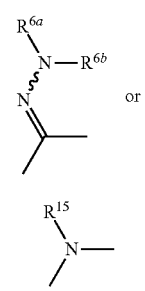

A-6 or

A-7

B is O or S;
$R^1$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_3$-$C_6$ halocycloalkylalkyl, $C_4$-$C_8$ alkylcycloalkyl, $C_4$-$C_8$ cycloalkylalkyl, $C_1$-$C_6$ alkylamino, $C_1$-$C_6$ haloalkylamino, $C_2$-$C_{10}$ dialkylamino, $C_2$-$C_{10}$ halodialkylamino, $C_3$-$C_6$ cycloamino, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy, $C_3$-$C_6$ cycloalkoxy, $C_3$-$C_6$ halocycloalkoxy, $C_4$-$C_8$ cycloalkylalkoxy, $C_4$-$C_8$ halocycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_6$ cyanoalkyl, $C_2$-$C_6$ cyanoalkoxy, $C_3$-$C_7$ cyanoalkoxyalkyl, $C_1$-$C_6$ hydroxyalkyl, $C_1$-$C_6$ nitroalkyl, $C_1$-$C_6$ alkylthio, $C_1$-$C_6$ haloalkylthio, $C_3$-$C_8$ cycloalkylthio, $C_1$-$C_6$ alkenylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_2$-$C_6$ alkylthioalkyl, $C_2$-$C_6$ haloalkylthioalkyl, benzyl, —N($R^7$)(O$R^8$), —ON($R^{9a}$)($R^{9b}$) or —N($R^7$)N($R^{9a}$)($R^{9b}$);
Z is O or S;
$R^2$ is halogen, cyano, nitro, $C_1$-$C_6$ alkoxy, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl or —SO$_n$$R^{10}$;
each $R^3$ is independently halogen, cyano, nitro, CHO, C(=O)NH$_2$, C(=S)NH$_2$, SO$_2$NH$_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_2$-$C_4$ alkoxy, $C_3$-$C_4$ alkenyloxy, $C_3$-$C_4$ alkynyloxy, $C_1$-$C_4$ haloalkoxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_2$-$C_4$ alkylthioalkyl, —C(=O)N($R^{11a}$)($R^{11b}$), —C(=NO$R^{12}$)H, —C(=N($R^{13}$))H or —SO$_n$$R^{14}$;

m is 0, 1, 2 or 3;

each n is independently 0, 1 or 2;

$R^4$ is H, $C_1$-$C_6$ alkyl or $C_1$-$C_6$ haloalkyl;

$R^5$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkoxyalkyl, $C_2$-$C_6$ haloalkoxyalkyl, $C_2$-$C_6$ alkoxyhaloalkyl, $C_2$-$C_6$ cyanoalkyl, $C_3$-$C_7$ cyanoalkoxyalkyl, $C_1$-$C_6$ hydroxyalkyl, $C_1$-$C_6$ nitroalkyl, $C_2$-$C_6$ alkylthioalkyl, $C_2$-$C_6$ haloalkylthioalkyl or benzyl;

each $R^{6a}$ and $R^{6b}$ is independently H, $C_1$-$C_6$ alkyl or $C_1$-$C_6$ haloalkyl;

$R^7$ is H, $C_1$-$C_6$ alkyl or $C_1$-$C_6$ haloalkyl;

$R^8$ is H, $C_1$-$C_6$ alkyl, $C_1$-$C_6$ haloalkyl, $C_2$-$C_6$ alkoxyalkyl, $C_2$-$C_6$ haloalkoxyalkyl or $C_2$-$C_6$ cyanoalkyl;

each $R^{9a}$ and $R^{9b}$ is independently H, $C_1$-$C_6$ alkyl or $C_1$-$C_6$ haloalkyl;

$R^{10}$ is independently $C_1$-$C_6$ alkyl, $C_1$-$C_6$ haloalkyl, $C_1$-$C_6$ alkylamino or $C_2$-$C_{10}$ dialkylamino;

each $R^{11a}$ is independently $C_1$-$C_4$ alkyl or $C_1$-$C_4$ haloalkyl;

each $R^{11b}$ is independently H, $C_1$-$C_4$ alkyl or $C_1$-$C_4$ haloalkyl;

each $R^{12}$ is independently H or $C_1$-$C_4$ alkyl;

each $R^{13}$ is independently H, amino, $C_1$-$C_4$ alkyl or $C_1$-$C_4$ alkylamino;

each $R^{14}$ is independently $C_1$-$C_6$ alkyl, $C_1$-$C_6$ haloalkyl, $C_1$-$C_6$ alkylamino or $C_2$-$C_{10}$ dialkylamino; and $R^{15}$ is H or $C_1$-$C_6$ alkyl;

provided that (i) when A is A-1 then $R^1$ is other than H, $C_1$-$C_6$ alkyl or $C_2$-$C_6$ alkenyl;

(ii) when A is A-6, then $R^1$ is other than $C_1$-$C_6$ alkylsulfonyl;

(iii) when A is A-1, $R^2$ is Cl and $R^3$ is 3-Br, then $R^1$ is other than $C_2$ alkylthio, $C_2$ alkylsulfinyl or $C_2$ alkylsulfonyl; and (iv) the compound of Formula 1 is other than methyl 2-[(5-chloro-2-pyrimidinyl)oxy]benzoate (CAS Registry No. 854215-38-6), methyl 2-[(5-bromo-2-pyrimidinyl)oxy]benzoate (CAS Registry No. 1086397-52-5), 1-[2-[(5-bromo-2-pyrimidinyl)oxy]phenyl]-ethanone (CAS Registry No. 1147704-06-0) and 2-[(5-bromo-2-pyrimidinyl)oxy]-benzeneacetonitrile (CAS Registry No. 138193-83-6).

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. Examples of "alkoxyalkoxy" include $CH_3OCH_2O$, $(CH_3)_2CHOCH_2O$, $CH_3OCH_2CH_2O$ and $CH_3CH_2OCH_2CH_2CH_2O$. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Cyanoalkyl" denotes an alkyl group substituted with one cyano group. "Cyanoalkoxy" denotes an alkoxy group substituted with one cyano group. "Cyanoalkoxyalkyl" denotes an alkoxyalkyl group substituted with one cyano group. Examples of "cyanoalkyl" include $NCCH_2$, $NCCH_2CH_2$ and $CH_3CH(CN)CH_2$. The term "hydroxyalkyl" denotes an alkyl group substituted with one hydroxy group. Examples of "hydroxyoalkyl" include $HOCH_2$—, $HOCH_2CH_2$— and $CH_3CH(OH)CH_2$—. The term "nitroalkyl" denotes an alkyl group substituted with one nitro group. Examples of "nitroalkyl" include $O_2NCH_2$—, $O_2NCH_2CH_2$— and $CH_3CH(NO_2)CH_2$—. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkylalkoxy" denotes cycloalkyl substitution on an alkoxy moiety. The term "cycloalkylcarbonyl" denotes cycloalkyl substitution bonded through a carbonyl moiety. Examples of "cycloalkylcarbonyl" include c-Pr(C=O)—, cyclopentyl(C=O)—. The term "cycloalkylsulfonyl" denotes cycloalkyl substitution bonded through a sulfonyl moiety. Examples of "cycloalkylsulfonyl" include c-Pr(S=O$_2$)—, cyclopentyl(S=O$_2$)—. The term "cycloalkylthio" denotes cycloalkyl substitution bonded through a sulfer atom. Examples of "cycloalkylthio" include c-Pr(S)—, cyclopenty(S)—. Examples of "cycloalkylalkoxy" include cyclopropylmethoxy, cyclopentylethoxy. The term "cycloalkoxy" denotes cycloalkyl linked through an oxygen atom such as cyclopentyloxy and cyclohexyloxy. The term "cycloamino" denotes a cyclic amine moiety bonded through nitrogen. Examples of "cycloamino" include —$N[CH_2CH_2CH_2$—] (i.e. azetidine) and —$N[CH_2CH_2CH_2CH_2$—], (i.e. pyrrolidine).

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "halocycloalkyl", "haloalkoxy", "haloalkylthio", "haloalkylsulfinyl", "haloalkylsulfonyl", "haloalkenyl", "haloalkynyl", "haloalkoxyalkoxy", "alkoxyhaloalkyl" and the like, are defined analogously to the term "haloalkyl". Examples of halocycloalkyl include c-Pr(2-Cl), c-Bu(2,2-di-Br) and c-Hex(3,5-di-Cl). Examples of "haloalkoxy" include $CF_3O$—, $CCl_3CH_2O$—, $HCF_2CH_2CH_2O$— and $CF_3CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—. Examples of "haloalkenyl" include $(Cl)_2C=CHCH_2$— and $CF_3CH_2CH=CHCH_2$—. Examples of "haloalkynyl" include $HC\equiv CCHCl$—, $CF_3C\equiv C$—, $CCl_3C\equiv C$— and $FCH_2C\equiv CCH_2$—. Examples of "haloalkoxyalkoxy" include $CF_3OCH_2O$—, $ClCH_2CH_2OCH_2CH_2O$—, $Cl_3CCH_2OCH_2O$— as well as branched alkyl derivatives. Examples of "alkoxyhaloalkyl" include $CH_3OCF_2CH_2$—, $CH_3CH_2OCH_2CCl_2$—, $CF_3CH_2CH_2OCH_2$— as well as branched alkyl derivatives.

The term "haloalkenyloxy" refers to a haloalkenyl group bonded through oxygen. Examples of "haloalkenyloxy" include $(Cl)_2C=CHCH_2O$— and $CF_3CH_2CH=CHCH_2O$—. The term "haloalkylamino" refers to a haloalkyl group bonded through a nitrogen atom (i.e. as a secondary amine). Examples of "haloalkylamino" include $CF_3NH$—, $CCl_3CH_2NH$—, $HCF_2CH_2CH_2NH$— and $CF_3CH_2NH$—. The term "haloalkylcarbonyl" refers to a haloalkyl group bonded through a carbonyl moiety. Examples of "haloalkylcarbonyl" include $CH_2ClC(=O)$—, $CH_3CHClCH_2C(=O)$— and $(CH_3)_2CCl(=O)$—. The term "haloalkylthioalkyl" refers to a haloalkylthio group bonded through an alkyl moiety. Examples of "haloalkylthioalkyl" include $CCl_3SCH_2$—, $CF_3SCH_2$—, $CCl_3CH_2SCH_2$— and $ClCH_2CH_2CH_2SCH_2$—. The term "haloalkynyloxy" refers to a haloalkynyl group bonded through an oxygen atom. Examples of "haloalkynyloxy" include $HC\equiv CCHClO$—, $CF_3C\equiv CO$—, $CCl_3C\equiv CO$— and $FCH_2C\equiv CCH_2O$— haloalkynyloxy. The term "haloalkoxyalkyl" refers to a haloalkoxy group bonded through an alkyl moiety. Examples of "haloalkoxyalkyl" include $CF_3OCH_2$—, $ClCH_2CH_2OCH_2CH_2$—, $Cl_3CCH_2OCH_2$— as well as branched alkyl derivatives. The term "halocycloalkoxy" refers to a halocycloalkyl group bonded through an oxygenatom. Examples of "halocycloalkoxy" include c-Pr(2-Cl)$CH_2O$— and c-Bu(1-Cl)$CH_2CH_2O$—. The term "halodialkylamino" indicate two haloalkyl groups bonded through nitrogen. Examples of "halodialkylamino" include $(CH_2Cl)_2N$—, $(CH_2CH_2Cl)_2N$— and $(CH_2CH_2Cl)(CH_2Br)N$—.

"Alkylcarbonyl" denotes a straight-chain or branched alkyl moieties bonded to a C(=O) moiety. Examples of "alkylcarbonyl" include $CH_3C(=O)$—, $CH_3CH_2CH_2C(=O)$— and $(CH_3)_2CHC(=O)$—. Examples of "alkoxycarbonyl" include CH$_3$OC(=O)—, CH$_3$CH$_2$OC(=O)—, CH$_3$CH$_2$CH$_2$OC(=O)—, (CH$_3$)$_2$CHOC(=O)— and the different butoxy- or pentoxycarbonyl isomers. Examples of "alkylcarbonyloxy" include CH$_3$C(=O)O—, CH$_3$CH$_2$CH$_2$C(=O)O— and (CH$_3$)$_2$CHC(=O)O—

The total number of carbon atoms in a substituent group is indicated by the "C$_i$-C$_j$" prefix where i and j are numbers from 1 to 10. For example, C$_1$-C$_4$ alkylsulfonyl designates methylsulfonyl through butylsulfonyl; C$_2$ alkoxyalkyl designates CH$_3$OCH$_2$—; C$_3$ alkoxyalkyl designates, for example, CH$_3$CH(OCH$_3$)—, CH$_3$OCH$_2$CH$_2$— or CH$_3$CH$_2$OCH$_2$—; and C$_4$ alkoxyalkyl designates the various isomers of an alkyl group substituted with an alkoxy group containing a total of four carbon atoms, examples including CH$_3$CH$_2$CH$_2$OCH$_2$— and CH$_3$CH$_2$OCH$_2$CH$_2$—.

When a compound is substituted with a substituent bearing a subscript that indicates the number of said substituents can exceed 1, said substituents (when they exceed 1) are independently selected from the group of defined substituents, e.g., (R$^3$)$_m$, where m is 0, 1, 2 or 3. Further, when the subscript indicates a range, e.g. (R)$_{i-j}$, then the number of substituents may be selected from the integers between i and j inclusive. When a group contains a substituent which can be hydrogen, for example (R$^1$ or R$^4$), then when this substituent is taken as hydrogen, it is recognized that this is equivalent to said group being unsubstituted. When a variable group is shown to be optionally attached to a position, for example (R$^3$)$_m$ wherein m may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of Formula 1 is carbocyclic or heterocyclic. The term "ring system" denotes two or more fused rings. The term "ring member" refers to an atom or other moiety (e.g., C(=O), C(=S), S(O) or S(O)$_2$) forming the backbone of a ring or ring system.

A compound of Formula 1 in the Summary of the Invention can alternatively be represented by the following:

1-A-1

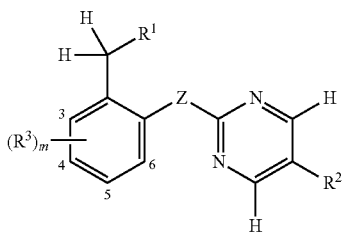

1-A-2

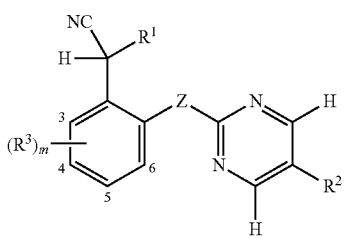

1-A-3

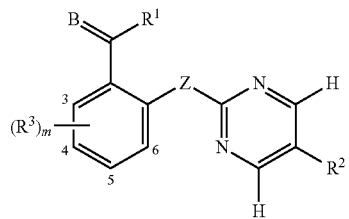

1-A-4

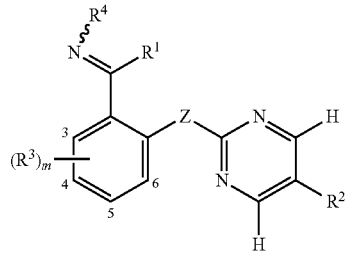

1-A-5

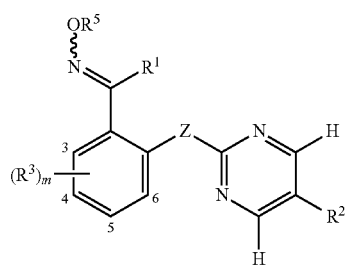

1-A-6

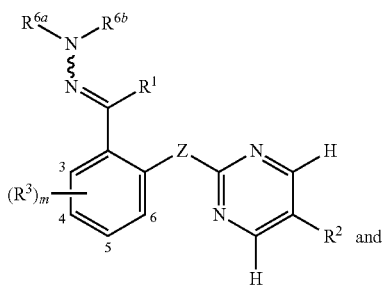

and

1-A-7

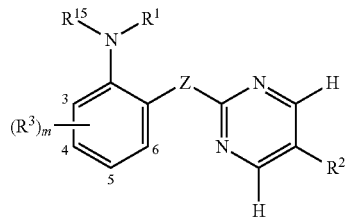

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" in which no ring in the ring system is aromatic. The term "nonaromatic heterocyclic ring system" denotes a heterocyclic ring system in which no ring in the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. For a comprehensive discussion of all aspects of stereoisomerism, see Ernest L. Eliel and Samuel H. Wilen, *Stereochemistry of Organic Compounds*, John Wiley & Sons, 1994.

Compounds of this invention can exist as one or more conformational isomers due to restricted rotation about the amide bond (e.g., C(=A)-$R^1$ wherein $R^1$ is alkylamino) in Formula 1. This invention comprises mixtures of conformational isomers. In addition, this invention includes compounds that are enriched in one conformer relative to others.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include:

Embodiment 1

A compound of Formula 1 including all geometric and stereoisomers, N-oxides, and salts thereof, agricultural compositions containing them and their use as herbicides.

Embodiment 2

A compound of Embodiment 1 wherein A is A-1, A-2, A-3 or A-5.

Embodiment 3

A compound of Embodiment 2 wherein A is A-1, A-2 or A-5.

Embodiment 4

A compound of Embodiment 3 wherein A is A-1 or A-2.

Embodiment 5

A compound of Embodiment 1 wherein A is A-1 or A-3.

Embodiment 6

A compound of Embodiment 1 wherein A is A-1.

Embodiment 7

A compound of Embodiment 1 wherein A is A-2.

Embodiment 8

A compound of Embodiment 1 wherein A is A-3.

Embodiment 9

A compound of Embodiment 1 wherein A is A-4.

Embodiment 10

A compound of Embodiment 1 wherein A is A-5.

Embodiment 11

A compound of Embodiment 1 wherein A is A-6.

Embodiment 12

A compound of Embodiment 1 wherein A is A-7.

Embodiment 13

A compound of any one of Embodiments 1, 2, 5 or 8 wherein B is O.

Embodiment 14

A compound of Formula 1 or any one of Embodiments 1 through 14 either alone or in combination, wherein $R^1$ is $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_3$-$C_6$ halocycloalkylalkyl, $C_4$-$C_8$ alkylcycloalkyl, $C_4$-$C_8$ cycloalkylalkyl, $C_1$-$C_6$ alkylamino, $C_1$-$C_6$ haloalkylamino, $C_2$-$C_{10}$ dialkylamino, $C_2$-$C_{10}$ halodialkylamino, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy, $C_3$-$C_6$ cycloalkoxy, $C_3$-$C_6$ halocycloalkoxy, $C_4$-$C_8$ cycloalkylalkoxy, $C_4$-$C_8$ halocycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_6$ cyanoalkyl, $C_2$-$C_6$ cyanoalkoxy, $C_3$-$C_7$ cyanoalkoxyalkyl, $C_1$-$C_6$ hydroxyalkyl, $C_1$-$C_6$ nitroalkyl, $C_1$-$C_6$ alkylthio, $C_1$-$C_6$ haloalkylthio, $C_3$-$C_8$ cycloalkylthio, $C_1$-$C_6$ alkenylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_2$-$C_6$ alkylthioalkyl, $C_2$-$C_6$ haloalkylthioalkyl, benzyl, —N($R^7$)(O$R^8$), —ON($R^{9a}$)($R^{9b}$) or —N($R^7$)N($R^{9a}$)($R^{9b}$).

Embodiment 15

A compound of Embodiment 14 wherein $R^1$ is $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_3$-$C_6$ halocycloalkylalkyl, $C_4$-$C_8$ alkylcycloalkyl, $C_4$-$C_8$ cycloalkylalkyl, $C_1$-$C_6$ alkylamino, $C_1$-$C_6$ haloalkylamino, $C_2$-$C_{10}$ dialkylamino, $C_2$-$C_{10}$ halodialkylamino, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy, $C_3$-$C_6$ cycloalkoxy, $C_3$-$C_6$ halocycloalkoxy, $C_4$-$C_8$ cycloalkylalkoxy, $C_4$-$C_8$ halocycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_6$ cyanoalkyl, $C_2$-$C_6$ cyanoalkoxy, $C_3$-$C_7$ cyanoalkoxyalkyl, $C_1$-$C_6$ hydroxyalkyl, $C_1$-$C_6$ nitroalkyl, $C_1$-$C_6$ alkylthio, $C_1$-$C_6$ haloalkylthio, $C_3$-$C_8$ cycloalkylthio, $C_1$-$C_6$ alkenylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_2$-$C_6$ alkylthioalkyl or $C_2$-$C_6$ haloalkylthioalkyl.

Embodiment 16

A compound of Embodiment 15 wherein $R^1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ cycloalkoxy, $C_4$-$C_8$ cycloalkylalkoxy, $C_2$-$C_6$ cyanoalkyl, $C_2$-$C_6$ cyanoalkoxy, $C_1$-$C_6$ alkylthio, $C_1$-$C_6$ haloalkylthio or $C_1$-$C_6$ alkenylthio.

Embodiment 17

A compound of Embodiment 16 wherein $R^1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_2$-$C_6$ cyanoalkyl, $C_2$-$C_6$ cyanoalkoxy, $C_1$-$C_6$ alkylthio, $C_1$-$C_6$ haloalkylthio or $C_1$-$C_6$ alkenylthio.

Embodiment 18

A compound of Embodiment 17 wherein $R^1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_1$-$C_6$ alkylthio, $C_1$-$C_6$ haloalkylthio or $C_1$-$C_6$ alkenylthio.

Embodiment 19

A compound of Embodiment 17 wherein $R^1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_6$ alkenyloxy, $C_3$-$C_6$ alkynyloxy or $C_3$-$C_6$ haloalkenyloxy.

Embodiment 20

A compound of Embodiment 19 wherein $R^1$ is $C_1$-$C_6$ alkyl, $C_2$-$C_6$ alkenyl, $C_1$-$C_6$ haloalkyl, $C_1$-$C_6$ alkoxy or $C_1$-$C_6$ haloalkoxy.

Embodiment 21

A compound of Embodiment 20 wherein $R^1$ is $C_1$-$C_6$ alkyl, $C_1$-$C_6$ haloalkyl, $C_1$-$C_6$ alkoxy or $C_1$-$C_6$ haloalkoxy.

Embodiment 22

A compound of Embodiment 21 wherein $R^1$ is $C_1$-$C_6$ alkyl.

Embodiment 23

A compound of Embodiment 21 wherein $R^1$ is $C_1$-$C_6$ haloalkyl.

Embodiment 24

A compound of Embodiment 21 wherein $R^1$ is $C_1$-$C_6$ alkoxy.

Embodiment 25

A compound of Embodiment 21 wherein $R^1$ is $C_2$-$C_6$ haloalkoxy.

Embodiment 26

A compound of Embodiment 21 wherein $R^1$ is $C_4$-$C_6$ alkyl, $C_3$-$C_6$ haloalkyl, $C_3$-$C_6$ alkoxy or $C_3$-$C_6$ haloalkoxy.

Embodiment 27

A compound of Embodiment 26 wherein when A is A-3 then $R^1$ is $C_3$-$C_6$ haloalkyl.

Embodiment 28

A compound of Embodiment 26 wherein when A is A-1 then $R^1$ is $C_4$-$C_6$ haloalkyl.

Embodiment 29

A compound of Embodiment 28 wherein when A is A-1 then $R^1$ is $C_4$-$C_5$ haloalkyl.

Embodiment 30

A compound of Embodiment 29 wherein when A is A-1 then $R^1$ is $CH_2CH_2CH_2CF_3$.

Embodiment 31

A compound of Embodiment 29 wherein when A is A-1 then $R^1$ is $CH_2CH_2CF_2CF_3$.

Embodiment 32

A compound of Embodiment 19 wherein when A is A-3 then $R^1$ is $C_4$-$C_6$ haloalkenyloxy.

Embodiment 33

A compound of Embodiment 26 wherein when A is A-3 then $R^1$ is $C_4$-$C_5$ haloalkoxy.

Embodiment 34

A compound of Embodiment 23 wherein $R^1$ is $CH_2CH_2CH_2CH_2CH_2CF_3$.

Embodiment 35

A compound of Embodiment 23 wherein $R^1$ is $CH_2CH_2CH_2CH_2CF_3$.

Embodiment 36

A compound of Embodiment 23 wherein $R^1$ is $CH_2CH_2CH_2CF_3$.

Embodiment 37

A compound of Embodiment 23 wherein $R^1$ is $CH_2CH_2CF_3$.

Embodiment 38

A compound of Embodiment 25 wherein $R^1$ is $OCH_2CH_2CH_2CH_2CF_3$.

Embodiment 39

A compound of Embodiment 25 wherein $R^1$ is $OCH_2CH_2CH_2CF_3$.

Embodiment 40

A compound of Embodiment 25 wherein $R^1$ is $OCH_2CH_2CF_3$.

Embodiment 41

A compound of Embodiment 25 wherein $R^1$ is $OCH_2CF_2CF_3$.

Embodiment 42

A compound of any one Embodiments 1 through 13 wherein $R^1$ is other than H.

Embodiment 43

A compound of any one Embodiments 1 through 14 wherein $R^1$ is other than benzyl (unsubstituted).

Embodiment 44

A compound of any one Embodiments 1 through 22 wherein $R^1$ is other than $CH_3$, $CH_2CH_3$ or $CH_2CH_2CH_3$.

Embodiment 45

A compound of any one Embodiments 1 through 20 or wherein $R^1$ is other than $CH_2CH=CH_2$, $CH=CHCH_3$, $C(=CH_2)CH_3$ or $CH=C(CH_3)_2$

Embodiment 46

A compound of Embodiment 1 wherein $R^1$ is other than propen-2-yl, propen-1-yl, n-propyl, ethyl, 1-methylethen-2-yl or 2-methylpropen-1-yl (i.e. $R^1$ is other than $CH_2CH=CH_2$, $CH_2CH_2CH_3$, $CH=CHCH_3$, $CH_2CH_3$, $C(=CH_2)CH_3$ or $CH=C(CH_3)_2$.

Embodiment 47

A compound of any one Embodiments 1 through 22 or 24 wherein $R^1$ is other than $OCH_3$.

Embodiment 48

A compound of Formula 1 or any one of Embodiments 1 through 47 either alone or in combination, wherein Z is O.

Embodiment 49

A compound of Formula 1 or any one of Embodiments 1 through 48 either alone or in combination, wherein $R^2$ is halogen, $C_1$-$C_4$ alkyl or $C_1$-$C_4$ haloalkyl.

Embodiment 50

A compound of Embodiment 49 wherein $R^2$ is halogen or $C_1$-$C_4$ alkyl.

Embodiment 51

A compound of Embodiment 50 wherein $R^2$ is halogen or $CH_3$.

Embodiment 52

A compound of Embodiment 51 wherein $R^2$ is halogen.

Embodiment 53

A compound of Embodiment 52 wherein $R^2$ is F, Cl or Br.

Embodiment 54

A compound of Embodiment 53 wherein $R^2$ is Cl.

Embodiment 55

A compound of Formula 1 or any one of Embodiments 1 through 54 either alone or in combination, wherein m is 0, 1 or 2.

Embodiment 56

A compound of Embodiment 55 wherein m is 0 or 1.

Embodiment 57

A compound of Embodiment 56 wherein m is 1.

Embodiment 58

A compound of Embodiment 57 wherein m is 1, at the 3, 4 or 6-position.

Embodiment 59

A compound of Embodiment 58 wherein m is 1, at the 3 or 4-position.

Embodiment 60

A compound of Embodiment 59 wherein m is 0 (i.e. each of the 3-, 4-, 5- and 6-positions are unsubstituted by $R^3$).

Embodiment 61

A compound of Formula 1 or any one of Embodiments 1 through 60 either alone or in combination, wherein each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_2$-$C_6$ alkoxyalkyl, $C_2$-$C_6$ haloalkoxyalkyl, $C_2$-$C_4$ alkylcarbonyloxy, $C_2$-$C_6$ cyanoalkyl, $-C(=O)N(R^{11a}R^{11b})$, $-C(=NOR^{12})H$ or $-SO_nR^{14}$.

Embodiment 62

A compound of Embodiment 61 wherein each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl, $C_2$-$C_6$ haloalkoxyalkyl, $C_2$-$C_6$ cyanoalkyl or $-SO_nR^{14}$.

Embodiment 63

A compound of Embodiment 62 wherein each $R^3$ is independently halogen, cyano, $C_1$-$C_4$ alkyl or $C_1$-$C_4$ haloalkyl.

Embodiment 64

A compound of Embodiment 63 wherein each $R^3$ is independently halogen, cyano, $C_1$-$C_3$ alkyl or $C_1$-$C_3$ haloalkyl.

Embodiment 65

A compound of Embodiment 64 wherein each $R^3$ is independently halogen, cyano, $C_1$-$C_2$ alkyl or $C_1$-$C_2$ haloalkyl.

Embodiment 66

A compound of Embodiment 65 wherein each $R^3$ is independently halogen, cyano, $CH_3$, $CH_2CH_3$ or $CF_3$.

Embodiment 67

A compound of Embodiment 66 wherein each $R^3$ is independently halogen, cyano or $CF_3$.

Embodiment 68

A compound of Embodiment 67 wherein each $R^3$ is independently F, Cl, Br or cyano.

Embodiment 69

A compound of Embodiment 68 wherein each $R^3$ is independently Br or cyano.

Embodiment 70

A compound of Embodiment 69 wherein each $R^3$ is independently halogen or cyano.

Embodiment 71

A compound of Embodiment 70 wherein each $R^3$ is independently cyano.

Embodiment 72

A compound of Embodiment 70 wherein each $R^3$ is independently halogen.

Embodiment 73

A compound of Embodiment 72 wherein each $R^3$ is independently Br.

Embodiment 74

A compound of Formula 1 or any one of Embodiments 1 through 73 either alone or in combination, wherein m is at least 1 and one $R^3$ is located at the 3-position (i.e. adjacent to the -$AR^1$ group) represented by the compound of Formula 1D

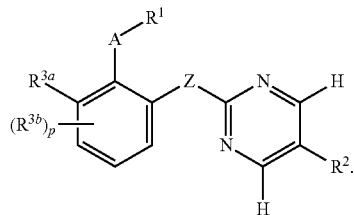

wherein A, $R^1$, $R^2$ and Z are as defined in the Summary of the Invention or in any one of Embodiments 1 through 59;
$R^{3a}$ is as defined for $R^3$ in any one of Embodiments 61 through 73;
$R^{3b}$ is as defined for $R^3$ in any one of Embodiments 61 through 73; and
p is 0 or 1.

Embodiment 75

A compound of Embodiment 74 wherein p is 1; $R^{3a}$ is halogen, cyano, $C_1$-$C_3$ alkyl, $C_1$-$C_3$ haloalkyl or $C_1$-$C_3$ alkoxy; and $R^{3b}$ is halogen, cyano, $C_1$-$C_3$ alkyl, $C_1$-$C_3$ haloalkyl or $C_1$-$C_3$ alkoxy.

Embodiment 76

A compound of Embodiment 75 wherein p is 0 and $R^{3a}$ is halogen, cyano, $C_1$-$C_3$ alkyl, $C_1$-$C_3$ haloalkyl or $C_1$-$C_3$ alkoxy.

Embodiment 77

A compound of Embodiment 76 wherein $R^{3a}$ is halogen or cyano.

Embodiment 78

A compound of Embodiment 77 wherein $R^{3a}$ is Br or cyano.

Embodiment 79

A compound of Formula 1 or any one of Embodiments 1 through 28 either alone or in combination, wherein $R^5$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_2$-$C_6$ alkoxyalkyl, $C_2$-$C_6$ haloalkoxyalkyl, $C_2$-$C_6$ cyanoalkyl, $C_3$-$C_7$ cyanoalkoxyalkyl, $C_2$-$C_6$ alkylthioalkyl or $C_2$-$C_6$ haloalkylthioalkyl.

Embodiment 80

A compound of Embodiment 79 wherein $R^5$ is $C_1$-$C_6$ alkyl or $C_1$-$C_6$ haloalkyl.

Embodiment 81

A compound of Embodiment 1 wherein when A is A-5, then $R^3$ is in the 4-, 5- or 6-position.

Embodiment 82

A compound of Embodiment 1 wherein when A is A-3, B is O, $R^3$ is 3-Br then $R^1$ is other then 3-bromopropane.

Embodiment 83

A compound of Embodiment 1 wherein when A is A-3, $R^3$ is halogen at the 3-position.

Embodiment 84

A compound of Embodiment 1 wherein when A is A-1, $R^3$ is cyano at the 3-position.

Embodiment 85

A compound of Embodiment 1 wherein $R^1$ is other than $C_3$-$C_6$ cycloamino.

Embodiment 86

A compound of Embodiment 1 wherein each $R^{11a}$ is independently $C_1$-$C_2$ alkyl $C_1$-$C_2$ haloalkyl.

Embodiment 87

A compound of Embodiment 1 wherein each $R^{11b}$ is independently $C_1$-$C_2$ alkyl or $C_1$-$C_2$ haloalkyl.

Embodiment 88

A compound of Embodiment 1 wherein each $R^{12}$ is independently H or $C_1$-$C_3$ alkyl.

Embodiment 89

A compound of Embodiment 1 wherein each $R^{14}$ is independently $C_1$-$C_3$ alkyl or $C_1$-$C_3$ haloalkyl.

Embodiment 90

A compound of Embodiment 1 wherein each $R^{14}$ is independently $C_1$-$C_3$ alkyl.

Embodiment 91

A compound of Embodiment 1 wherein m is 1, 2 or 3.

Embodiment 92

A compound of Embodiment 1 wherein m is 1 or 2.

Embodiments of this invention, including Embodiments 1-92 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-92 above as well as any other embodiments described herein, and any combination thereof, pertain to the compositions and methods of the present invention.

Combinations of Embodiments 1-92 are illustrated by:

Embodiment A

A compound of Formula 1 wherein
A is A-1, A-2, A-3 or A-5;
$R^1$ is $R^1$ is $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_3$-$C_6$ halocycloalkylalkyl, $C_4$-$C_8$ alkylcycloalkyl, $C_4$-$C_8$ cycloalkylalkyl, $C_1$-$C_6$ alkylamino, $C_1$-$C_6$ haloalkylamino, $C_2$-$C_{10}$ dialkylamino, $C_2$-$C_{10}$ halodialkylamino, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy, $C_3$-$C_6$ cycloalkoxy, $C_3$-$C_6$ halocycloalkoxy, $C_4$-$C_8$ cycloalkylalkoxy, $C_4$-$C_8$ halocycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_6$ cyanoalkyl, $C_2$-$C_6$ cyanoalkoxy, $C_3$-$C_7$ cyanoalkoxyalkyl, $C_1$-$C_6$ hydroxyalkyl, $C_1$-$C_6$ nitroalkyl, $C_1$-$C_6$ alkylthio, $C_1$-$C_6$ haloalkylthio, $C_3$-$C_8$ cycloalkylthio, $C_1$-$C_6$ alkenylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_2$-$C_6$ alkylthioalkyl or $C_2$-$C_6$ haloalkylthioalkyl;
$R^2$ is halogen, $C_1$-$C_4$ alkyl or $C_1$-$C_4$ haloalkyl;
each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_2$-$C_6$ alkoxyalkyl, $C_2$-$C_6$ haloalkoxyalkyl, $C_2$-$C_4$ alkylcarbonyloxy, $C_2$-$C_6$ cyanoalkyl, —C(=O)N($R^{11a}R^{11b}$), —C(=NOR$^{12}$)H or —SO$_n$R$^{14}$;
$R^5$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_2$-$C_6$ alkoxyalkyl, $C_2$-$C_6$ haloalkoxyalkyl, $C_2$-$C_6$ cyanoalkyl, $C_3$-$C_7$ cyanoalkoxyalkyl, $C_2$-$C_6$ alkylthioalkyl or $C_2$-$C_6$ haloalkylthioalkyl;
$R^{11a}$ is $C_1$-$C_2$ alkyl $C_1$-$C_2$ haloalkyl;
$R^{11b}$ is $C_1$-$C_2$ alkyl or $C_1$-$C_2$ haloalkyl;
$R^{12}$ is H or $C_1$-$C_3$ alkyl; and
$R^{14}$ is $C_1$-$C_3$ alkyl or $C_1$-$C_3$ haloalkyl.

Embodiment B

A compound of Embodiment A wherein
A is A-1, A-2 or A-5;
$R^1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ cycloalkoxy, $C_4$-$C_8$ cycloalkylalkoxy, $C_2$-$C_6$ cyanoalkyl, $C_2$-$C_6$ cyanoalkoxy, $C_1$-$C_6$ alkylthio, $C_1$-$C_6$ haloalkylthio or $C_1$-$C_6$ alkenylthio;
$R^2$ is halogen or $C_1$-$C_4$ alkyl;
each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl, $C_2$-$C_6$ haloalkoxyalkyl, $C_2$-$C_6$ cyanoalkyl or —SO$_n$R$^{14}$;
$R^5$ is $C_1$-$C_6$ alkyl or $C_1$-$C_6$ haloalkyl;
each $R^{14}$ is independently $C_1$-$C_3$ alkyl; and
m is 0, 1 or 2.

Embodiment C

A compound of Embodiment B wherein
A is A-1 or A-2;
$R^1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_2$-$C_6$ cyanoalkyl, $C_2$-$C_6$ cyanoalkoxy, $C_1$-$C_6$ alkylthio, $C_1$-$C_6$ haloalkylthio or $C_1$-$C_6$ alkenylthio;
$R^2$ is halogen or $CH_3$; and
each $R^3$ is independently halogen, cyano, $C_1$-$C_4$ alkyl or $C_1$-$C_4$ haloalkyl.

Embodiment D

A compound of Embodiment C wherein
A is A-1;
$R^1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_1$-$C_6$ alkylthio, $C_1$-$C_6$ haloalkylthio or $C_1$-$C_6$ alkenylthio;
Z is O;
$R^2$ is halogen;
each $R^3$ is independently halogen, cyano, $C_1$-$C_3$ alkyl or $C_1$-$C_3$ haloalkyl; and
m is 1 or 2.

Embodiment E

A compound of Embodiment C wherein
A is A-2;
$R^1$ is $C_1$-$C_6$ alkyl, $C_2$-$C_6$ alkenyl, $C_1$-$C_6$ haloalkyl, $C_1$-$C_6$ alkoxy or $C_1$-$C_6$ haloalkoxy;
Z is O;
$R^2$ is F, Cl or Br;
each $R^3$ is independently halogen, cyano, $C_1$-$C_2$ alkyl or $C_1$-$C_2$ haloalkyl; and
m is 0 or 1.

Embodiment F

A compound of Embodiment A wherein
A is A-3;
$R^1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ cycloalkoxy, $C_4$-$C_8$ cycloalkylalkoxy, $C_2$-$C_6$ cyanoalkyl, $C_2$-$C_6$ cyanoalkoxy, $C_1$-$C_6$ alkylthio, $C_1$-$C_6$ haloalkylthio or $C_1$-$C_6$ alkenylthio;
$R^2$ is halogen or $C_1$-$C_4$ alkyl;
each $R^3$ is independently halogen, cyano, $C_1$-$C_4$ alkyl or $C_1$-$C_4$ haloalkyl; and
m is 1 or 2.

Embodiment G

A compound of Embodiment F wherein
B is O;
$R^1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_2$-$C_6$ cyanoalkyl, $C_2$-$C_6$ cyanoalkoxy, $C_1$-$C_6$ alkylthio, $C_1$-$C_6$ haloalkylthio or $C_1$-$C_6$ alkenylthio;
Z is O;
$R^2$ is halogen or $CH_3$;
each $R^3$ is independently halogen, cyano, $C_1$-$C_3$ alkyl or $C_1$-$C_3$ haloalkyl; and
m is 1 or 2.

Specific embodiments include compounds of Formula 1 selected from the group consisting of:
3,3,3-trifluoropropyl 2-chloro-6-[(5-chloro-2-pyrimidinyl)oxy]benzoate (Compound 15);
3,3,3-trifluoro-1-methylpropyl 2-bromo-6-[(5-chloro-2-pyrimidinyl)oxy]benzoate (Compound 16);
propyl 2-bromo-6-[(5-chloro-2-pyrimidinyl)oxy]benzoate (Compound 13);
4,4,4-trifluorobutyl 2-bromo-6-[(5-chloro-2-pyrimidinyl)oxy]benzoate (Compound 20);
2-propen-1-yl 2-bromo-6-[(5-chloro-2-pyrimidinyl)oxy]benzoate (Compound 22);
3-buten-1-yl 2-bromo-6-[(5-chloro-2-pyrimidinyl)oxy]benzoate (Compound 21);
2,2,3,3,3-pentafluoropropyl 2-bromo-6-[(5-chloro-2-pyrimidinyl)oxy]benzoate (Compound 23);
3,3,3-trifluoropropyl 2-bromo-6-[(5-chloro-2-pyrimidinyl)oxy]benzoate (Compound 26);
1-[2-chloro-6-[(5-chloro-2-pyrimidinyl)oxy]phenyl]-4,4,4-trifluoro-1-butanone (Compound 107); and
3-[(5-chloro-2-pyrimidinyl)oxy]-2-(5,5,5-trifluoropentyl) benzonitrile (Compound 73).

Embodiments of the present invention as described in the Summary of the Invention include (where Formula 1P as used in the following Embodiments includes N-oxides and salts thereof):

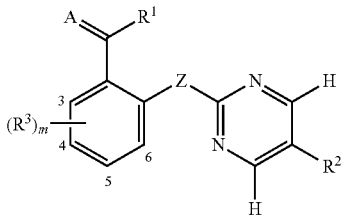

Embodiment P1

A compound of Formula 1P wherein A is $H_2$, O, S or $N(OR^5)$.

Embodiment P2

A compound of Embodiment P1 wherein A is $H_2$, O or $N(OR^5)$.

Embodiment P3

A compound of Embodiment P2 wherein A is O or $N(OR^5)$.

Embodiment P4

A compound of Embodiment P3 wherein A is O.

Embodiment P5

A compound of Embodiment P3 wherein A is $N(OR^5)$.

Embodiment P6

A compound of Formula 1P or any one of Embodiments P1 through P5 either alone or in combination, wherein $R^1$ is $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_1$-$C_6$ alkylamino, $C_1$-$C_6$ haloalkylamino, $C_2$-$C_{10}$ dialkylamino, $C_2$-$C_{10}$ halodialkylamino, $C_3$-$C_6$ cycloamino, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy, $C_3$-$C_6$ cycloalkoxy, $C_3$-$C_6$ halocycloalkoxy, $C_4$-$C_8$ cycloalkylalkoxy, $C_4$-$C_8$ halocycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_6$ cyanoalkyl, $C_2$-$C_6$ cyanoalkoxy, $C_3$-$C_7$ cyanoalkoxyalkyl, $C_1$-$C_6$ hydroxyalkyl, $C_1$-$C_6$ nitroalkyl, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_2$-$C_6$ alkylthioalkyl, $C_2$-$C_6$ haloalkylthioalkyl, benzyl, —$NR^7OR^8$, —$ON(R^{9a}R^{9b})$ or —$NR^7N(R^{9a}R^{9b})$.

Embodiment P7

A compound of Embodiment P6 wherein $R^1$ is $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_1$-$C_6$ alkylamino, $C_1$-$C_6$ haloalkylamino, $C_2$-$C_{10}$ dialkylamino, $C_2$-$C_{10}$ halodialkylamino, $C_3$-$C_6$ cycloamino, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy, $C_3$-$C_6$ cycloalkoxy, $C_3$-$C_6$ halocycloalkoxy, $C_4$-$C_8$ cycloalkylalkoxy, $C_4$-$C_8$ halocycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_6$ cyanoalkyl, $C_2$-$C_6$ cyanoalkoxy, $C_3$-$C_7$ cyanoalkoxyalkyl, $C_1$-$C_6$ hydroxyalkyl, $C_1$-$C_6$ nitroalkyl, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_2$-$C_6$ alkylthioalkyl or $C_2$-$C_6$ haloalkylthioalkyl.

Embodiment P8

A compound of Embodiment P7 wherein $R^1$ is $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy or $C_3$-$C_6$ cycloalkoxy.

Embodiment P9

A compound of Embodiment P8 wherein $R^1$ is $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy or $C_3$-$C_6$ cycloalkoxy.

Embodiment P10

A compound of Formula 1P or any one of Embodiments P1 through P9 either alone or in combination, wherein Z is O.

Embodiment P11

A compound of Formula 1P or any one of Embodiments P1 through P10 either alone or in combination, wherein $R^2$ is halogen, $C_1$-$C_4$ alkyl or $C_1$-$C_4$ haloalkyl.

Embodiment P12

A compound of Embodiment P11 wherein $R^2$ is halogen or $C_1$-$C_4$ alkyl.

Embodiment P13

A compound of Embodiment P12 wherein $R^2$ is halogen or $CH_3$.

Embodiment P14

A compound of Embodiment P13 wherein $R^2$ is halogen.

Embodiment P15

A compound of Embodiment P14 wherein $R^2$ is F, Cl or Br.

Embodiment P16

A compound of Formula 1P or any one of Embodiments P1 through P15 either alone or in combination, wherein m is 0, 1 or 2.

Embodiment P17

A compound of Embodiment P16 wherein m is 0 or 1.

Embodiment P18

A compound of Embodiment P17 wherein m is 1.

Embodiment P19

A compound of Embodiment P17 wherein m is 0 (i.e. the 3-, 4-, 5- and 6-positions are unsubstituted by $R^3$).

Embodiment P20

A compound of Formula 1P or any one of Embodiments P1 through P19 either alone or in combination, wherein each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_2$-$C_6$ alkoxyalkyl, $C_2$-$C_6$ haloalkoxyalkyl, $C_2$-$C_4$ alkylcarbonyloxy, $C_2$-$C_6$ cyanoalkyl, —$C(=O)N(R^{11a}R^{11b})$, —$C(=NOR^{12})H$ or —$SO_nR^{14}$.

Embodiment P21

A compound of Embodiment P20 wherein each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl, $C_2$-$C_6$ haloalkoxyalkyl, $C_2$-$C_6$ cyanoalkyl or —$SO_nR^{14}$.

Embodiment P22

A compound of Embodiment P21 wherein each $R^3$ is independently halogen, cyano, $C_1$-$C_4$ alkyl or $C_1$-$C_4$ haloalkyl.

Embodiment P23

A compound of Embodiment P22 wherein each $R^3$ is independently halogen or cyano.

Embodiment P24

A compound of Embodiment P23 wherein each $R^3$ is independently cyano.

Embodiment P25

A compound of Embodiment P23 wherein each $R^3$ is independently halogen.

Embodiment P26

A compound of Embodiment P23 wherein each $R^3$ is independently Br.

Embodiment P27

A compound of Formula 1P or any one of Embodiments P1 through P26 either alone or in combination, wherein m is 1 and $R^3$ is located at the 3-position (i.e. adjacent to the $C(=A)R^1$ group).

Embodiment P28

A compound of Formula 1P or any one of Embodiments P1 through P26 either alone or in combination, wherein m is 2 and $R^3$ is located at the 3- and the 6-position (i.e. adjacent to the $C(=A)R^1$ group and the Z(pyrimidine group).

Embodiment P29

A compound of Formula 1P or any one of Embodiments P1 through P28 either alone or in combination, wherein $R^5$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_2$-$C_6$ alkoxyalkyl, $C_2$-$C_6$ haloalkoxyalkyl, $C_2$-$C_6$ cyanoalkyl, $C_3$-$C_7$ cyanoalkoxyalkyl, $C_2$-$C_6$ alkylthioalkyl or $C_2$-$C_6$ haloalkylthioalkyl.

Embodiment P30

A compound of Embodiment P29 wherein $R^5$ is $C_1$-$C_6$ alkyl, or $C_1$-$C_6$ haloalkyl.

Embodiments of this invention, including Embodiments P1-P30 above as well as any other embodiments described herein, can be combined in any manner, and the descriptions of variables in the embodiments pertain not only to the compounds of Formula 1P but also to the starting compounds and intermediate compounds useful for preparing the compounds of Formula 1P. In addition, embodiments of this invention, including Embodiments P1-P30 above as well as any other embodiments described herein, and any combination thereof, pertain to the compositions and methods of the present invention.

Combinations of Embodiments P1-P30 are illustrated by:

Embodiment PA

A compound of Formula 1P wherein
A is $H_2$, O, S or $N(OR^5)$;
$R^1$ is $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_1$-$C_6$ alkylamino, $C_1$-$C_6$ haloalkylamino, $C_2$-$C_{10}$ dialkylamino, $C_2$-$C_{10}$ halodialkylamino, $C_3$-$C_6$ cycloamino, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy, $C_3$-$C_6$ cycloalkoxy, $C_3$-$C_6$ halocycloalkoxy, $C_4$-$C_8$ cycloalkylalkoxy, $C_4$-$C_8$ halocycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_6$ cyanoalkyl, $C_2$-$C_6$ cyanoalkoxy, $C_3$-$C_7$ cyanoalkoxyalkyl, $C_1$-$C_6$ hydroxyalkyl, $C_1$-$C_6$ nitroalkyl, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_2$-$C_6$ alkylthioalkyl or $C_2$-$C_6$ haloalkylthioalkyl;
Z is O;
$R^2$ is halogen, $C_1$-$C_4$ alkyl or $C_1$-$C_4$ haloalkyl;
each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl, $C_2$-$C_6$ haloalkoxyalkyl, $C_2$-$C_6$ cyanoalkyl or —$SO_nR^{14}$; and
m is 0, 1 or 2.

Embodiment PB

A compound of Embodiment PA wherein
A is $H_2$, O or $N(OR^5)$;
$R^1$ is $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy or $C_3$-$C_6$ cycloalkoxy;
$R^2$ is halogen or $C_1$-$C_4$ alkyl;
each $R^3$ is independently halogen, cyano, $C_1$-$C_4$ alkyl or $C_1$-$C_4$ haloalkyl;
$R^5$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_2$-$C_6$ alkoxyalkyl, $C_2$-$C_6$ haloalkoxyalkyl, $C_2$-$C_6$ cyanoalkyl, $C_3$-$C_7$ cyanoalkoxyalkyl, $C_2$-$C_6$ alkylthioalkyl or $C_2$-$C_6$ haloalkylthioalkyl; and
m is 0 or 1.

Embodiment PC

A compound of Embodiment PB wherein
A is O or $N(OR^5)$;
$R^1$ is $C_1$-$C_6$ alkoxy, $C_3$-$C_6$ alkenyloxy, $C_3$-$C_6$ alkynyloxy, $C_1$-$C_6$ haloalkoxy, $C_3$-$C_6$ haloalkenyloxy, $C_3$-$C_6$ haloalkynyloxy or $C_3$-$C_6$ cycloalkoxy;
$R^2$ is halogen or $CH_3$;
$R^3$ is independently halogen or cyano; and
$R^5$ is $C_1$-$C_6$ alkyl, or $C_1$-$C_6$ haloalkyl.

Embodiment PD

A compound of Embodiment PC wherein
A is O;
$R^2$ is halogen; and
each $R^3$ is independently halogen.

Specific embodiments include compounds of Formula 1 selected from the group consisting of:

3,3,3-trifluoropropyl 2-chloro-6-[(5-chloro-2-pyrimidinyl) oxy]benzoate (Compound 15), 3,3,3-trifluoro-1-methylpropyl 2-bromo-6-[(5-chloro-2-pyrimidinyl)oxy]benzoate (Compound 16), propyl 2-bromo-6-[(5-chloro-2-pyrimidinyl)oxy]benzoate (Compound 13), 4,4,4-trifluorobutyl 2-bromo-6-[(5-chloro-2-pyrimidinyl)oxy]benzoate (Compound 20), 2-propen-1-yl 2-bromo-6-[(5-chloro-2-pyrimidinyl)oxy] benzoate (Compound 22), 3-buten-1-yl 2-bromo-6-[(5-chloro-2-pyrimidinyl)oxy]benzoate (Compound 21), 2,2,3,3,3-pentafluoropropyl 2-bromo-6-[(5-chloro-2-pyrimidinyl)oxy]benzoate (Compound 23), and 3,3,3-trifluoropropyl 2-bromo-6-[(5-chloro-2-pyrimidinyl) oxy]benzoate (Compound 26).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenzmethyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimehyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3 (2H)-pyridazinone, 4-(4-fluorophenyl)-6-[(2-hydroxy-6-oxo-1-cyclohexen-1-yl)carbonyl]-2-methyl-1,2,4-triazine-3,5(2H, 4H)-dione, 5-[(2-hydroxy-6-oxo-1-cyclohexen-1-yl) carbonyl]-2-(3-methoxyphenyl)-3-(3-methoxypropyl)-4 (3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, cyclopyrimorate (6-chloro-3-(2-cyclopropyl-6-methylphenoxy)-4-pyridazinyl 4-morpholinecarboxylate), 3-(2-chloro-3,6-difluorophenyl)-4-hydroxy-1-methyl-1,5-naphthyridin-2(1H)-one, 7-(3,5-dichloro-4-pyridinyl)-5-(2,2-difluoroethyl)-8-hydroxypyrido[2,3-b]pyrazin-6(5H)-one and 4-(2,6- diethyl-4-methylphenyl)-5-hydroxy-2,6-dimethyl-3 (2H)-pyridazinone.

HST inhibitors also include compounds of Formulae A and B.

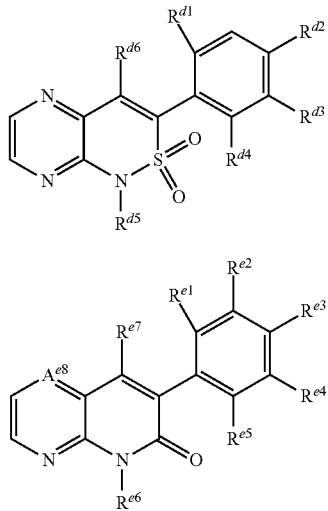

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide.

An embodiment of the present invention is a herbicidal mixture comprising (a) a compound of Formula 1, and (b) at least one additional active ingredient selected from (b1) photosystem II inhibitors, (b2) acetohydroxy acid synthase (AHAS) inhibitors, (b4) auxin mimics, (b5) 5-enol-pyruvyl-shikimate-3-phosphate (EPSP) synthase inhibitors, (b7) protoporphyrinogen oxidase (PPO) inhibitors, (b9) very long chain fatty acid (VLCFA) elongase inhibitors and (b12) 4-hydroxyphenyl-pyruvate dioxygenase (HPPD) inhibitors.

The compounds of Formula 1 can be prepared by general methods known in the art of synthetic organic chemistry. One or more of the following methods and variations as described in Schemes 1-10 can be used to prepare the compounds of Formula 1. The definitions of (A, Z, $R^1$, $R^2$, $R^3$, $R^4$, $R^5$, $R^{6a}$ and $R^{6b}$) in the compounds of Formulae 1-17 below are as defined above in the Summary of the Invention unless otherwise noted. Compounds of Formulae 1a-1b are various subsets of the compounds of Formula 1, and all substituents for Formulae 1a-1b are as defined above for Formula 1 unless otherwise noted.

As shown in Scheme 1 a compound of Formula 1 can be prepared by nucleophilic substitution by heating a compound of Formula 2 in a suitable solvent, such as acetonitrile, tetrahydrofuran or N,N-dimethylformamide in the presence of a base such as potassium or cesium carbonate, with a compound of Formula 3 (wherein LG is halogen or $SO_2Me$). The reaction is typically conducted at temperatures ranging from 20 to 110° C.

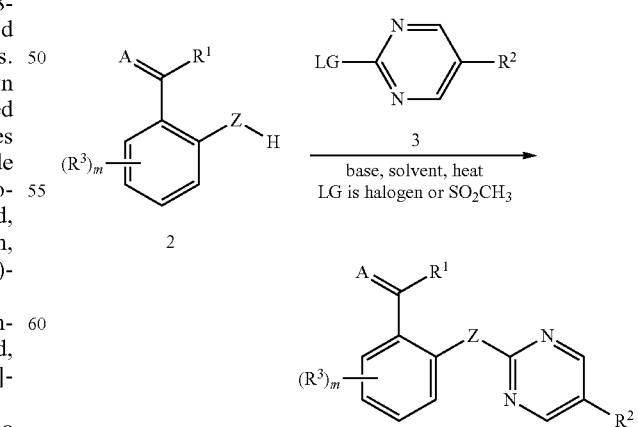

Scheme 1

As shown in Scheme 2, compounds of Formula 1b (wherein A is S) can be prepared by reacting compounds of Formula 1a (wherein A is A-3 and B is O) with a thionation reagent such as Lawesson's reagent, tetraphosphorus decasulfide or diphosphorus pentasulfide in a solvent such as tetrahydrofuran or toluene. Typically, the reaction is carried out at temperatures ranging from 0 to 115° C.

Scheme 2

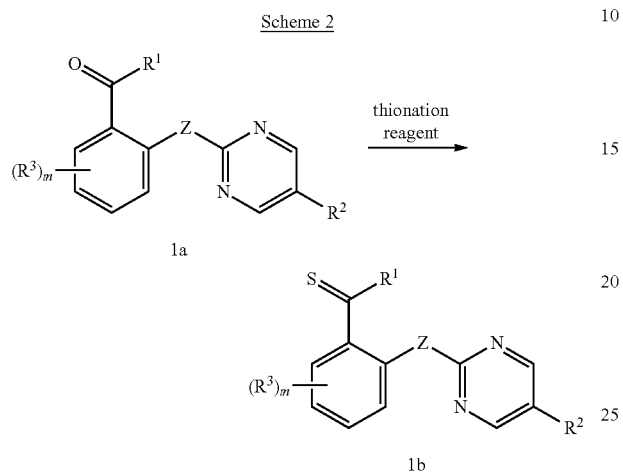

As shown in Scheme 3, a compound of Formula 2a (wherein A is A-3, B is O and Z is O) can be prepared by deprotection of a compound of Formula 4 (wherein $R^{20}$ is $CH_3$ or $C(=O)CH_3$) with a suitable deprotecting agent. Suitable methoxy (i.e. when $R^{20}$ is $CH_3$) deprotecting reagents such as $BBr_3$, $AlCl_3$ and HBr in acetic acid can be used in the presence of solvents such as toluene, dichloromethane and dichloroethane at a temperature of from −80 to 120° C. Suitable acetoxy (i.e. when $R^{20}$ is $C(=O)CH_3$) deprotecting agents include potassium carbonate in methanol or ammonium acetate in aqueous methanol at room temperature can be used as discussed in Das, et al., *Tetrahedron* 2003, 59, 1049-1054 and methods cited therein. Alternatively, a compound of Formula 4 can be combined with Amberlyst 15© in methanol (as discussed in Das, et al. *Tet. Lett.* 2003, 44, 5465-5468) or combined with sodium acetate in ethanol (as discussed in Narender, T., et al. *Synthetic Communications* 2009, 39(11), 1949-1956) to obtain a compound of Formula 2a. Other useful phenolic protecting groups suitable for use in preparing a compound of Formula 2a can be found in Greene, T. W.; Wuts, P. G. M. *Protective Groups in Organic Synthesis*, 4th ed.; Wiley: Hoboken, N.J., 1991.

Scheme 3

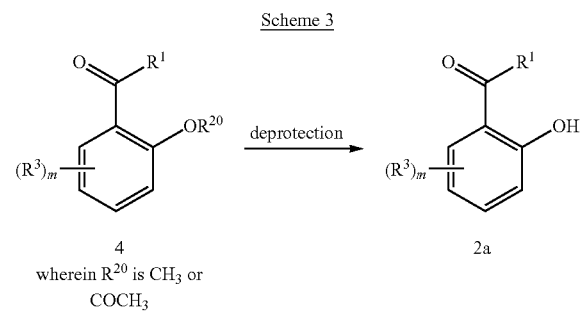

As shown in Scheme 4 compounds of Formula 5 (wherein $R^{1a}$ is alkyl, alkenyl, or alkynyl) can be prepared by reaction of organometallic reagents such as organomagnesium or organolithium reagents of Formula 6 with amides of the Formula 7. This reaction is typically carried out in a solvent such as tetrahydrofuran or diethyl ether at temperatures ranging from −78 to 25° C. To those skilled in the art, Amides such as Formula 7 are commonly referred to as a 'Weinreb Amide' and this type of transformation is commonly referred to as the 'Weinreb-Nahm ketone synthesis.' See *Synthesis* 2008, 23, 3707-3738 and references cited therein.

Scheme 4

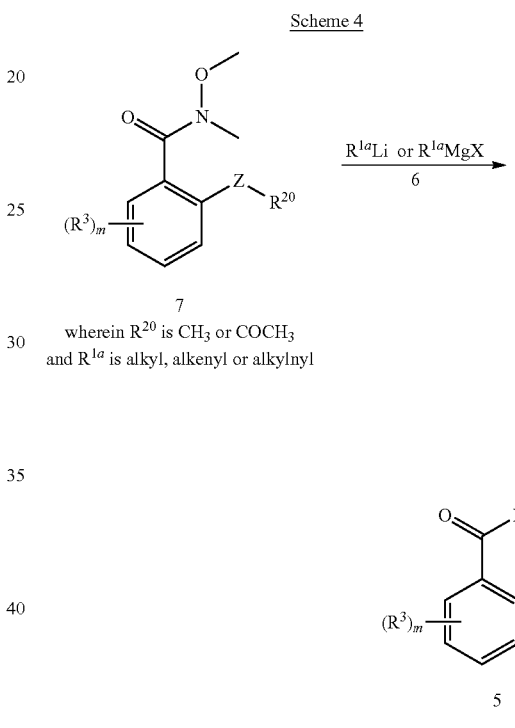

wherein $R^{20}$ is $CH_3$ or $COCH_3$
and $R^{1a}$ is alkyl, alkenyl or alkylnyl As shown in Scheme 5 compounds of Formula 8 can be prepared by reaction of acids of Formula 9 with alkylamines, alcohols or thiols of Formula 10 (wherein Rib is alkoxy, alkylthio or alkylamino) in the presence of a dehydrative coupling reagent such as propylphosphonic anhydride, dicyclohexylcarbodiimide, N-(3-dimethylaminopropyl)-N-ethylcarbodiimide, N,N-carbonyldiimidazole, 2-chloro-1,3-dimethylimidazolium chloride or 2-chloro-1-methylpyridinium iodide. Polymer-supported reagents, such as polymer-supported cyclohexylcarbodiimide, are also suitable. These reactions are typically run at temperatures ranging from 0-60° C. in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene. See *Organic Process Research & Development* 2009, 13, 900-906 for coupling conditions employing propylphosphonic anhydride.

Scheme 5

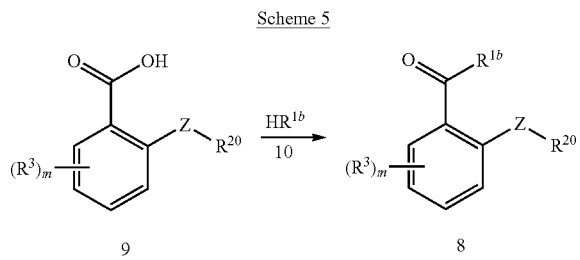

wherein $R^{20}$ is $CH_3$ or $COCH_3$
and $R^{1b}$ is alkoxy, thioalkyl or alkylamino In Scheme 6 a compounds of Formula 11 (wherein $R^x$ is $R^4$, $OR^5$ or $NR^{6a}R^{6b}$) can readily be prepared by condensation of an organoamine, organohydroxylamine, or organohydrazine with a compound of Formula 8, typically in the presence of either an acid or base. Reactions are typically run in solvents such as methanol, ethanol, dichloromethane, or toluene at temperatures ranging from 20-110° C. Suitable acids for the reactions include, but are not limited to, inorganic acids such as hydrochloric acids and organic acids such as acetic acid and trifluoroacetic acid. Suitable bases for the reaction include, but are not limited to, hydroxides such as sodium hydroxide, carbonates such as sodium and potassium carbonate, and organic bases such as sodium acetate and pyridine.

Scheme 6

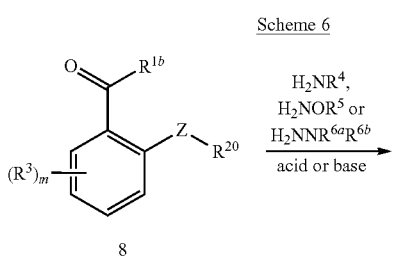

wherein $R^{20}$ is $CH_3$ or $COCH_3$
and $R^x$ is $R^4$, $OR^5$ or $NR^{6a}R^{6b}$

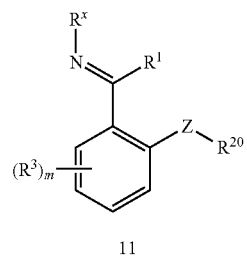

As shown in Scheme 7 benzylic alcohols of Formula 12 can be prepared by reduction of aldehydes of Formula 13 by a wide variety of methods well known to those skilled in the art. Suitable reducing agents for the reaction include, but are not limited to, sodium borohydride, lithium aluminum hydride, and diisobutylaluminium hydride. A variety of solvents are also suitable for this reaction and include, but are not limited to, methanol, ethanol, and tetrahydrofuran with typically reaction temperatures ranging from −10° C. to 25° C.

Scheme 7

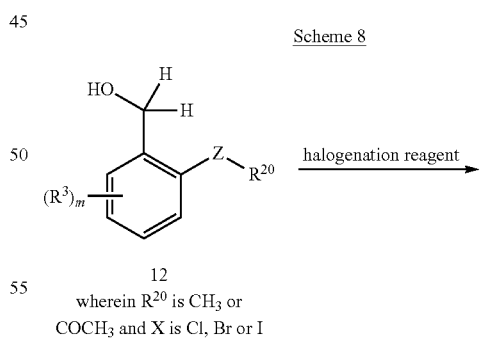

wherein $R^{20}$ is $CH_3$ or $COCH_3$

As shown in Scheme 8 benzylic halides of Formula 14 (wherein X is Cl, Br or I) can be prepared by substitution of alcohol with a halide on compounds of Formula 12 by a wide variety of methods well known to those skilled in the art. One such method employs thionyl chloride, optionally with N,N-dimethyl formamide, in solvents including, but not limited to dichloromethane, toluene, chloroform and no solvent at temperatures typically between 0-80° C. Alternatively compounds of the Formula 14 can be prepared from benzyl alcohols of the Formula 12 employing a phosphorus reagent and a halide regent. A typical phosphorus reagent is triphenyl phosphine and halide reagents include, but are not limited to, carbon tetrahalide, N-halosuccinimide, dihalide, and tetrahalomethane. Solvents suitable for this reaction include, but are not limited to, dichloromethane, tetrahydrofuran, and acetonitrile and typical reaction temperatures range from −78-50° C. This latter reaction is well known to those skilled in the art and is referred to as an 'Appel Reaction'. For examples see Smith, M. B.; March, J. *March's Advanced Organic Chemistry*, 6th ed., pages 576-580; John Wiley & Sons: Hoboken, N.J. and references therein.

Scheme 8

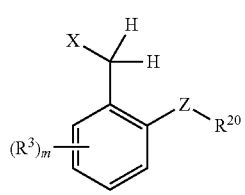

wherein $R^{20}$ is $CH_3$ or $COCH_3$ and X is Cl, Br or I

In Scheme 9 a benzylic heterateroatom containing compound of Formula 15 (wherein $R^{1b}$ is alkoxy, alkylthio or alkylamino) can readily be prepared by those skilled in the art by a displacement reaction with a compound of the Formula 14 using an appropriate heteroalkyl reagent of Formula 10 (alcohol, alkylamine, or thiol), typically in the presence of a base. Suitable solvents for the reaction include, but are not limited to, tetrahydrofuran, N,N-dimethylformamide, acetonitrile, toluene and dichloromethane. Suitable bases for the reaction include, but are not limited to, hydroxides such as sodium hydroxide and potassium hydroxide, hydride bases such as sodium hydride, carbonate bases such as sodium and potassium carbonate, and organic bases such as triethylamine and N,N-diethylisopropylamine. Additionally this reaction can be optionally substituted with an iodide, for example sodium iodide or tetrabutylammonium iodide.

Scheme 9

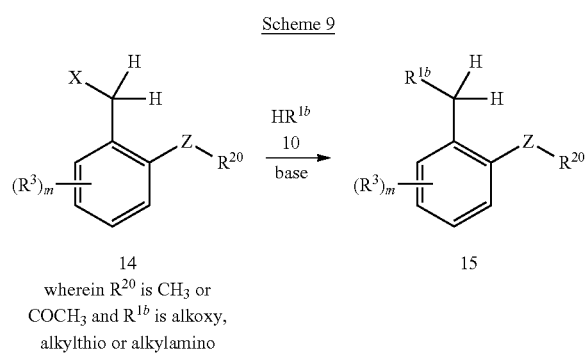

14 wherein $R^{20}$ is $CH_3$ or $COCH_3$ and $R^{1b}$ is alkoxy, alkylthio or alkylamino

15

As shown in Scheme 10 sulfone (n=1) and sulfoxides (n=2) of the Formula 16 can be readily prepared by the oxidation of a compound of Formula 17 (wherein A is A-1 and $R^{21}$ is alkyl or haloalkyl) by a wide variety of methods well known to those skilled in the art. Suitable reagents for this reaction include but are not limited to, dihydrogen peroxide, 3-chloro-benzenecarboxylic acid, sodium periodate, and Oxone. Typical solvents for this reaction include dichloromethane, methanol, tetrahydrofuran, and acetic acid and a typical reaction temperature range between −78 to 50° C. The sulfur is first oxidized to the sulfoxide (n=1) followed by oxidation to the sulfone (n=2). Careful monitoring reaction progress with well-established analytical methods (i.e. thin layer chromatography, nuclear magnetic resonance, etc.) allows for selection of the sulfoxide or sulfone.

Scheme 10

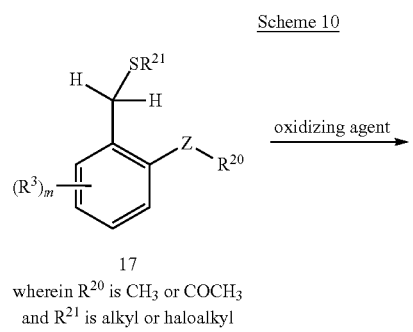

17 wherein $R^{20}$ is $CH_3$ or $COCH_3$ and $R^{21}$ is alkyl or haloalkyl

-continued

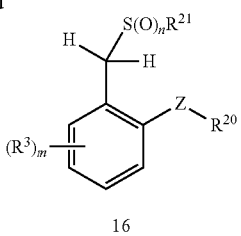

16

In Scheme 11 a compound of Formula 18 can readily be prepared by alkylation of a compound of Formula 19. This can be accomplished using an appropriate alkylating reagent in the presence of an appropriate base. Suitable solvents for this reaction generally include polar solvents including but not limited to N,N-dimethylformamide, dimethyl sulfoxide, acetonitrile, or tetrahydrofuran. Suitable bases generally include but are not limited to sodium hydride, sodium amide, sodium hydroxide, and lithium diisopropyl amide. Reaction temperatures range from 0° C. to 100° C. as described in synthesis Example 5.

Scheme 11

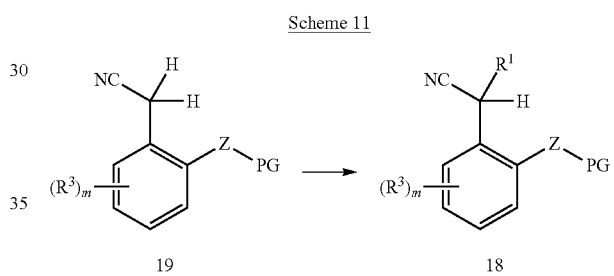

19                          18

As shown in Scheme 12 a compound of Formula 20 can be prepared through deoxygenation of a compound of Formula 21. One method utilizes a transition metal catalyst in the presence of a hydride source optionally in the presence of an acid utilizing a number of solvents including methanol and ethanol. A typical transition metal catalyst is palladium on carbon, and standard hydride sources include hydrogen gas, either at atmospheric or elevated pressure, or ammonium formate. Acids utilized for this reaction can include hydrochloric acid, sulfuric acid, and para-toluenesulfonic acid. An example of this reaction can be found in *J. Med. Chem.* 1992, 35, 1818. A second method employs a hydride source in combination with an acid. Typical hydride sources include triethylsilane and sodium borohydride, in combination with Brönsted acids such as trifluoroacetic acid and acetic acid, or Lewis acids such as boron trifluoride etherate. The solvent for these reactions can be the acid alone or as a mixture with a number of other common solvents such as dichloromethane or acetonitrile. An example of this reaction can be found in US 2007/0003539 or in Step B of synthesis Example 6.

Scheme 12

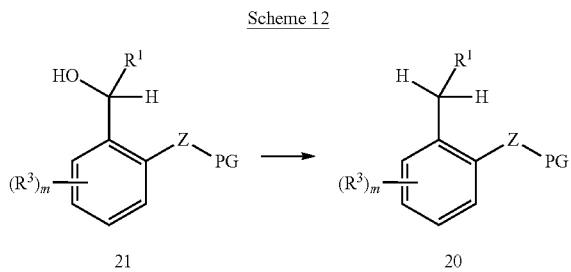

As shown in Scheme 13 a compound of Formula 22 (where $R^{1a}$ is alkyl, alenyl, or alkynyl) can be prepared by reaction of organometallic reagents such as organomagnesium or organolithium reagents with aldehydes of the Formula 23. This reaction is typically carried out in a solvent such as tetrahydrofuran or diethyl ether at temperatures ranging from −78 to 25° C. An example of this reaction can be found in *Synlett*, 2016, 27, 789 or as described in Step A of synthesis Example 6.

Scheme 13

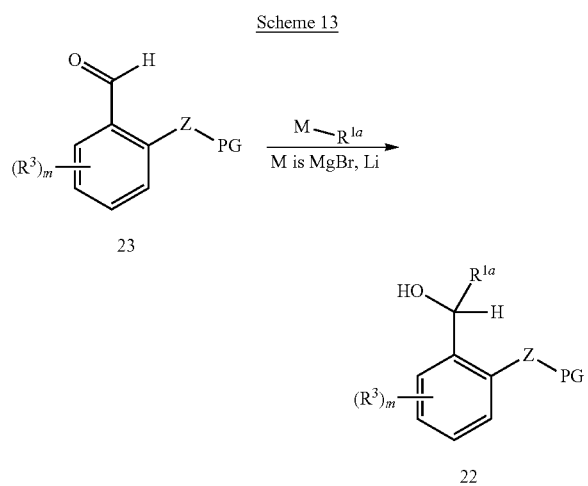

As shown in Scheme 14, compounds of Formula 25 can be prepared by a transition metal catalyzed coupling of a cyano group with a compound of Formula 24 ($R^{3a}$=Br or I). Conditions for this reaction generally include a cyanide source and a copper catalyst or palladium catalyst with a co-catalyst. This reaction is typically carried out with a copper(I) halide in the presence of a ligand such as 2-(methylamino)ethylamine or trans-N,N'-dimethylcyclohexane-1, 2-diamine with a metal cyanide salt. This reaction can be utilized in a range of polar aprotic solvents such as N,N-dimethylformamide, tetrahydrofuran, acetonitrile, N-methyl-2-pyrrolidone or toluene at temperatures ranging from 100 to 210° C. This reaction is known to those skilled in the art as the Rosenmund-von Braun reaction. Similar conditions can be utilized with copper(I) cyanide with or without the presence of added ligand and cyanide source. The analogous coupling can be affected by using a palladium catalyst such as tetrakis(triphenylphosphine)palladium, palladium diacetate, or tris(dibenzylideneacetone)dipalladium with optional phosphine ligands and a co-catalyst such as zinc cyanide. These reactions can be carried out in a range of polar aprotic solvents such as N,N-dimethylformamide, N-methyl-2-pyrrolidone, acetonitrile and 1,4-dioxane at temperatures ranging from 80 to 150° C. Alternatively a palladium co-catalyst such as copper(I) halide and a cyanide salt can be used in place of the zinc cyanide under similar conditions. An example of this reaction can be found in *J. Am. Chem. Soc.* 2003, 125, 2890 and as described in Step C of synthesis Example 6.

Scheme 14

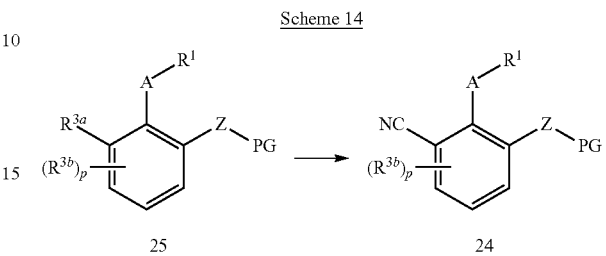

Compounds of Formulae 24, 22 and 20 can readily be converted to a compound of Formula 1 using the methods discussed for Scheme 3 and Scheme 1; by deprotection of the PG group and subsequent alkylation with a compound of Formula 3. It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet. Mass spectra (MS) are reported as the molecular weight of the highest isotopic abundance parent ion (M+1) formed by addition of H+ (molecular weight of 1) to the molecule, or (M−1) formed by the loss of H+ (molecular weight of 1) from the molecule, observed by using liquid chromatography coupled to a mass spectrometer (LCMS) using either atmospheric pressure chemical ionization (AP+) where "amu" stands for unified atomic mass units.

Example 1

Preparation of 2-[(5-chloro-2-pyrimidinyl)oxy]-N-(2,2,2-trifluoroethyl)benzamide (Compound 28)

Step A: Preparation of 2-methoxy-N-(2,2,2-trifluoroethyl)benzamide

A solution of 2,2,2-Trifluoroethylamine (1.28 g, 12.89 mmoles) and triethylamine (4.1 mL, 29.31 mmoles) in dichloromethane (30 mL) was cooled to 0° C. The reaction mixture was treated with a solution of 2-methoxybenzoyl chloride (2.0 g, 11.72 mmoles) in in dichloromethane (8 mL) at a temperature below 5° C. The reaction mixture was allowed to slowly warm to room temperature. De-ionized water was added and the mixture partitioned. The aqueous phase was extracted with dichloromethane. The combined organic phases were washed with 1N HCl and saturated aqueous sodium chloride solution and dried with magnesium sulfate and concentrated under vacuum to a white solid. The solid was filtered from hexanes to obtain the title compound (2.24 g) as a solid.

$^1$H NMR (400 MHz, CDCl$_3$) δ 8.20 (d, 2H), 7.49 (t, 1H), 7.10 (t, 1H), 7.00 (d, 1H), 4.10 (q, 2H), 3.99 (s, 3H).

Step B: Preparation of 2-hydroxy-N-(2,2,2-trifluoroethyl)benzamide

A solution of 2-methoxy-N-(2,2,2-trifluoroethyl)benzamide (i.e. the product of Step A) (1.0 g, 4.28 mmoles) in anhydrous dichloromethane (20 mL) was cooled with an ice-water bath to 0° C. The solution was treated with 1 M boron tribromide solution (4.72 mL, 4.72 mmoles) in dichloromethane dropwise and stirred for 3 hours. The reaction mixture was then poured into ice-water and partitioned. The aqueous phase was extracted with dichloromethane and then ethyl acetate. The combined organic phases were washed with saturated aqueous sodium chloride solution, dried with magnesium sulfate and concentrated under vacuum to a solid. The solid was filtered from hexanes to obtain the title compound (475 mg) as a solid.

$^1$H NMR (400 MHz, CDCl$_3$) δ 7.44 (t, 1H), 7.40 (d, 1H), 7.01 (d, 1H), 6.89 (t, 1H), 6.53 (bs, 1H), 4.13 (m, 2H).

Step C: Preparation of 2-[(5-chloro-2-pyrimidinyl)oxy]-N-(2,2,2-trifluoroethyl)-benzamide To a solution of 2-hydroxy-N-(2,2,2-trifluoroethyl)benzamide (i.e. the product of Step B) (100 mg, 0.456 mmoles) in acetonitrile (3 mL) was added 2,5-dichloropyrimidine (71 mg, 0.48 mmoles) and potassium carbonate (190 mg, 1.37 mmoles). The reaction mixture was heated to 80° C. for 12 hours. The reaction was partitioned between water and ethyl acetate, the organic phase was separated, dried with magnesium sulfate, and concentrated under vacuum. The residue was purified by chromatography on silica gel with a 5 gram Bond elut column, eluting with 20% ethyl acetate/hexanes to afford the title compound, a compound of the present invention, as an oil (0.30 g).

$^1$H NMR (400 MHz, CDCl$_3$) δ 8.30 (s, 2H), 7.65 (d, 1H), 7.48 (t, 1H), 7.31 (t, 1H), 7.21 (bs, 1H), 7.00 (d, 1H), 4.75 (q, 2H).

Example 2

Preparation of 3-buten-1-yl 2-bromo-6-[(5-chloro-2-pyrimidinyl)oxy]benzoate (Compound 21)

Step A: Preparation of 3-butenyl 2-bromo-6-hydroxybenzoate

To a stirred solution of 2-bromo-6-hydroxybenzoic acid (0.200 g, 0.921 mmol) in dry dichloromethane (3 mL) was added oxalyl chloride (94.8 μL, 1.11 mml) and 2 drops of N,N'-dimethylformamide. The reaction mixture was stirred at room temperature for 3 hours. The reaction mixture was then concentrated under vacuum and the residue was dissolved in dry dichloromethane (3 mL) and treated with 3-buten-1-ol (86.9 μL, 1.01 mmol) and 3 drops of triethylamine. The reaction mixture was stirred at room temperature for 18 hours. The reaction mixture was concentrated under vacuum onto Celite® diatomaceous earth filter aid and purified by column chromatography on silica gel, eluting with 0 to 20% ethyl acetate in hexanes to afford the title compound (0.117 g).

$^1$H NMR (500 MHz, CDCl$_3$) δ 10.96 (s, 1H), 7.24-7.17 (m, 2H), 6.98-6.93 (m, 1H), 5.95-5.87 (m, 1H), 5.22-5.18 (m, 1H), 5.15-5.12 (m, 1H), 4.47 (t, 2H), 2.62-2.57 (m, 2H).

Step B: Preparation of 3-buten-1-yl 2-bromo-6[(5-chloro-2-pyrimidinyl)oxy]benzoate To a stirred solution of 3-butenyl 2-bromo-6-hydroxybenzoate (i.e. the product of Step A) (0.117 g, 0.431 mmol) and 5-chloro-2-(methylsulfonyl)-pyrimidine (i.e. 5-chloro-2-methylsulfonylpyrimidine) (99.8 mg, 0.518 mmol) in N,N'-dimethylformamide (2 mL) was added potassium carbonate (85.9 mg, 0.646 mmol). The reaction mixture was stirred at room temperature for 18 hours. The reaction mixture was then filtered through a pad of Celite® diatomaceous earth filter aid and the filtrate was concentrated under vacuum. The crude residue was purified by column chromatography on silica gel, eluting with 0 to 30% ethyl acetate in hexanes to afford the title compound, a compound of the present invention, as a solid (0.104 g).

$^1$H NMR (500 MHz, CDCl$_3$) δ 8.48 (s, 2H), 7.53 (dd, 1H), 7.35 (t, 1H), 7.17 (dd, 1H), 5.75-5.65 (m, 1H), 5.11-4.99 (m, 2H), 4.29 (t, 2H), 2.39-2.34 (m, 2H).

Example 3

Preparation of 3,3,3-trifluoropropyl 2-bromo-6-[(5-chloro-2-pyrimidinyl)oxy]benzoate (Compound 26)

Step A: Preparation of 3,3,3-trifluoropropyl 2-bromo-6-hydroxybenzoate

To a stirred solution of 2-bromo-6-hydroxybenzoic acid (0.500 g, 2.30 mmol) and molecular sieves in 3,3,3-trifluoropropan-1-ol (15 mL) was added concentrated sulfuric acid (0.300 mL). The reaction mixture was heated at 78° C. for 24 hours. The reaction mixture was cooled to room temperature and filtered through a small pad of Celite® diatomaceous earth filter aid. The filtrate was diluted with ethyl acetate and washed with water, and saturated aqueous sodium chloride solution. The organic phase was separated, dried over magnesium sulfate and concentrated under vacuum. The crude material was purified by column chromatography on silica gel, eluting with 0 to 20% ethyl acetate in hexanes to afford the title compound (0.268 g).
$^1$H NMR (500 MHz, CDCl$_3$) δ 10.79 (s, 1H), 7.26-7.20 (m, 2H), 7.00-6.94 (m, 1H), 4.63 (t, 2H), 2.70 (m, 2H).

Step B: Preparation of 3,3,3-trifluoropropyl 2-bromo-6-[(5-chloro-2-pyrimidinyl)-oxy]benzoate To a stirred solution of 3,3,3-trifluoropropyl 2-bromo-6-hydroxybenzoate (i.e. the product of Step A) (0.124 g, 0.396 mmol) and 5-chloro-2-(methylsulfonyl)-pyrimidine (i.e. 5-chloro-2-methylsulfonylpyrimidine) (95.1 mg, 0.475 mmol) in N,N'-dimethylformamide (2 mL) was added potassium carbonate (82.1 mg, 0.594 mmol). The reaction was stirred at room temperature for 18 hours. The reaction mixture was filtered through a pad of Celite® diatomaceous earth filter aid and filtrate was concentrated under vacuum. The crude material was purified by column chromatography on silica gel, eluting with 0 to 30% ethyl acetate in hexanes to afford the title compound, a compound of the present invention, as a solid (55.0 mg).
$^1$H NMR (500 MHz, CDCl$_3$) δ 8.49 (s, 2H), 7.54 (dd, 1H), 7.38 (t, 1H), 7.20 (dd, 1H), 4.46 (t, 2H), 2.50 (m, 2H).

Example 4

Preparation of 1-[2-chloro-6-[(5-chloro-2-pyrimidinyl)oxy]phenyl]-4,4,4-trifluoro-1-butanone (Compound 107)

Step A: Preparation of 2-chloro-6-methoxy-α-(3,3,3-trifluoropropyl)benzenemethanol A reaction flask was charged with 1.92 g (79.18 mmol) of magnesium, a catalytic amount of iodine, and 50 mL of diethyl ether. The mixture was heated to reflux and 1,1,1-trifluoro-3-iodo-propane (10.64 g, 47.51 mmol) was added over 30 min. The mixture was allowed to cool to room temperature and transferred to a second reaction flask charged with 2-chloro-6-methoxy-benzaldehyde (6.75 g, 39.59 mmol) and 75 mL of tetrahydrofuran at −78° C. The reaction mixture was allowed to warm to room temperature, quenched with 1 N hydrochloric acid, and partitioned between diethyl ether and brine. The organic phase was dried over MgSO$_4$, filtered, and concentrated to provide 9.4 g of crude product that was used in the subsequent step without purification.

Step B: Preparation of 1-(2-chloro-6-methoxyphenyl)-4,4,4-trifluoro-1-butanone To a solution of 2-chloro-6-methoxy-α-(3,3,3-trifluoropropyl)benzenemethanol (i.e. the crude material obtained in Step A, 9.4 g) in 175 mL of acetone was added 15.7 mL (42 mmol) of 2.64 M Jones reagent over 15 min. The reaction mixture was stirred for an additional 30 min., quenched with 0.5 mL of isopropanol, and partitioned between diethyl ether and water. The organic phase was dried over MgSO$_4$, filtered, and concentrated. The crude material was purified by silica gel chromatography eluting with a hexane:ethyl acetate gradient to provide 7.0 g of the title compound.
$^1$H NMR (CDCl$_3$) δ 7.32-7.24 (m, 1H), 7.00 (d, 1H), 6.84 (d, 1H), 3.82 (s, 3H), 3.09-3.01 (m, 2H), 2.64-2.51 (m, 2H).

Step C: Preparation of 1-(2-chloro-6-hydroxyphenyl)-4,4,4-trifluoro-1-butanone To a solution of 1-(2-chloro-6-methoxyphenyl)-4,4,4-trifluoro-1-butanone (i.e. the product from Step B, 3.5 g, 13.2 mmol) of in 100 mL of dichloromethane was added boron tribromide (1.0 M in dichloromethane, 15.79 mL) at 0° C. The reaction solution was stirred for 2 h while warming to room temperature, which was then poured into ice cold dilute aqueous hydrochloric acid, and extracted with dichloromethane. The organic phase was dried over MgSO$_4$, filtered, and concentrated. The crude material was purified by silica gel chromatography eluting with a gradient of hexanes/ethyl acetate to provide 2.6 g of the title compound.
$^1$H NMR (CDCl$_3$) δ 11.88 (s, 1H), 7.35-7.30 (m, 1H), 7.01-6.98 (m, 1H), 6.96-6.92 (m, 1H), 3.55-3.49 (m, 2H), 2.65-2.53 (m, 2H).

Step D: Preparation of 1-[2-chloro-6-[(5-chloro-2-pyrimidinyl)oxy]phenyl]-4,4,4-trifluoro-1-butanone A reaction flask was charged with 1-(2-chloro-6-hydroxyphenyl)-4,4,4-trifluoro-1-butanone (i.e. the product obtained in Step C, 2.6 g, 10.3 mmol), 5-chloro-2-(methylsulfonyl)-pyrimidine (2.7 g, 14.0 mmol), potassium carbonate (1.7 g, 12.36 mmol), and 50 mL of isopropanol. The reaction mixture was heated to 50° C. for 1 h, poured into dilute ice cold aqueous hydrochloric acid, and extracted with diethyl ether repeatedly. The combined organic extracts were washed with brine, dried over MgSO$_4$, filtered, and concentrated. The crude material was purified by silica gel chromatography eluting with a gradient of hexanes/ethyl acetate to provide 3.0 g of the title compound, a compound of the invention.
$^1$H NMR (CDCl$_3$) δ 8.49 (s, 2H), 7.45-7.40 (m, 1H), 7.37-7.33 (m, 1H), 7.15-7.11 (m, 1H), 3.14-3.08 (m, 2H), 2.57-2.46 (m, 2H).

Example 5

Preparation of 2-[(5-chloro-2-pyrmidinyl)oxy]-α-pentylbenzeneacetonitrile (Compound 141)

Step A: Preparation of 2-methoxy-α-pentylbenzeneacetonitrile

To a solution of 2-methoxy-benzeneacetonitrile (500 mg, 3.39 mmol) in dimethylsulfoxide (5 mL) was added aqueous sodium hydroxide (50%, 0.75 mL) followed by 1-bromopentane (559 mg, 0.458 mL, 3.76 mmol) and the reaction mixture was stirred at ambient temperature for 18 h. The reaction mixture was partitioned between ethyl acetate and water, the organic phase was washed with water (3×). The organic phase was dried over MgSO$_4$ and concentrated under vacuum. The resulting residue was purified by chromatography on silica gel eluting with a gradient of 0 to 50% ethyl acetate in hexanes to afford the desired product in quantitative yield.
$^1$H NMR (500 MHz, CDCl$_3$) δ 7.38-7.41 (m, 1H), 7.27-7.31 (m, 1H), 6.96-7.01 (m, 1H), 6.87-6.91 (m, 1H), 4.15-

4.20 (m, 1H), 3.85 (s, 3H), 1.77-1.90 (m, 2H), 1.41-1.58 (m, 2H), 1.27-1.37 (m, 4H), 0.84-0.94 (m, 3H).

Step B: Preparation of 2-hydroxy-α-pentylbenzeneacetonitrile

To a solution of 2-methoxy-α-pentylbenzeneacetonitrile (i.e. the product of Step A, 440 mg, 2.02 mmol) in dichloromethane (10 mL) at 0° C. was added boron tribromide (1.0 M in dichloromethane, 10 mL, 10 mmol) and the reaction was allowed to warm to room temperature over 18 h. The reaction mixture was quenched with a saturated solution of sodium carbonate, the phases were separated and the organic layer was dried over $MgSO_4$. The solvent was removed under vacuum and purified by chromatography on silica gel, eluting with a gradient of 0 to 50% ethyl acetate in hexanes to afford the desired product (232 mg)
$^1$H NMR (500 MHz, $CDCl_3$) δ 7.35-7.39 (m, 1H), 7.15-7.20 (m, 1H), 6.93-6.98 (m, 1H), 6.76-6.79 (m, 1H), 5.28-5.40 (bs, 1H), 4.14-4.20 (m, 1H), 1.84-1.93 (m, 2H), 1.42-1.58 (m, 2H), 1.25-1.38 (m, 4H), 0.85-0.91 (m, 3H).

Step C: Preparation of 2-[(5-chloro-2-pyrmidinyl)oxy]-α-pentylbenzeneacetonitrile To a solution of 2-hydroxy-α-pentylbenzeneacetonitrile (208 mg, 1.02 mmol) in N,N'-dimethylformamide (2.0 mL) was added potassium carbonate (169 mg, 1.22 mmol) followed by 5-chloro-2-(methylsulfonyl)-pyrimidine (137 mg, 1.07 mmol) and the reaction was heated to 35° C. for 5 h. The reaction was partitioned between ethyl acetate and water. The organic phase was washed with water (3×), followed by drying over $MgSO_4$ and concentrating. The resulting residue was purified by chromatography on silica gel eluting with a gradient of 0 to 30% ethyl acetate in hexanes to afford the title product, a compound of the invention (171 mg).
$^1$H NMR (500 MHz, $CDCl_3$) δ 8.51 (s, 2H), 7.56-7.58 (m, 1H), 7.38-7.42 (m, 1H), 7.31-7.35 (m, 1H), 7.12-7.15 (m, 1H), 3.99-4.03 (m, 1H), 1.80-1.96 (m, 2H), 1.36-1.55 (m, 2H), 1.20-1.28 (m, 4H), 0.81-0.87 (m, 3H).

Example 6

Preparation of 3-[(5-chloro-2-pyrimidinyl)oxy]-2-(5,5,5-trifluoropentyl)benzonitrile (Compound 73)

Step A: Preparation of 2-bromo-6-methoxy-α-(4,4,4-trifluorobutyl)benzenemethanol To magnesium metal shavings (0.254 g, 10.5 mmol, 1.5 eq.) in dry diethyl ether (2 mL) was added a crystal of iodine. The mixture was warmed to 35° C. and stirred for 15 min. To this mixture was added 1-bromo-4,4,4-trifluorobutane (1.30 mL, 10.5 mmol, 1.5 eq.) over 30 min. The reaction mixture continued to stir at 35° C. until all the magnesium was consumed. The resulting Grignard reagent was taken up by syringe. In separate reaction vial 2-bromo-6-methoxybenzaldehyde (1.50 g, 6.97 mmol, 1.0 eq.) was dissolved in dry tetrahydrofuran (20 mL) and cooled to 0° C. The previously prepared Grignard reagent was added dropwise to the aldehyde. The reaction mixture was stirred at room temperature for 18 h. The reaction was quenched with 1 N hydrochloric acid and diluted with ethyl acetate. The organic layer was separated, dried and concentrated. The crude material was purified by column chromatography, eluting with a gradient of 0 to 20% ethyl acetate in hexanes to afford the desired product (2.15 g).
$^1$H NMR (500 MHz, $CDCl_3$) δ 7.21-7.16 (m, 1H), 7.09 (t, 1H), 6.90-6.87 (m, 1H), 5.17-5.09 (m, 1H), 3.90 (s, 3H), 3.72 (d, 1H), 2.24-2.10 (m, 2H), 2.02-1.75 (m, 3H), 1.73-1.61 (m, 1H).

Step B: Preparation of 1-bromo-3-methoxy-2-(5,5,5-trifluoropentyl)benzene

To a stirred solution of 2-bromo-6-methoxy-α-(4,4,4-trifluorobutyl)benzenemethanol (i.e. the product of Step A, 2.15 g, 6.58 mmol, 1.0 eq.) in dry dichloromethane (22 mL) was added triethylsilane (4.20 mL, 26.3 mmol, 4.0 eq.). After stirring for 15 min. trifluoroacetic acid (2.01 mL, 26.3 mmol, 4.0 eq.) was added and the reaction was heated to 40° C. After 2 h, another 4.0 eq. of trifluoroacetic acid was added and the reaction mixture was stirred at 40° C. for another 18 h. The reaction was cooled to room temperature and concentrated onto Celite® diatomaceous earth filter aid for purification by column chromatography, eluting with a gradient of 0 to 10% ethyl acetate in hexanes to afford the desired product (1.82 g).
$^1$H NMR (500 MHz, $CDCl_3$) δ 7.20-7.12 (m, 1H), 7.07-7.00 (m, 1H), 6.81-6.78 (m, 1H), 3.81 (s, 3H), 2.85-2.78 (m, 2H), 2.20-2.07 (m, 2H), 1.69-1.55 (m, 4H)

Step C: Preparation of 3-methoxy-2-(5,5,5-trifluoropentyl)benzonitrile

A solution of 1-bromo-3-methoxy-2-(5,5,5-trifluoropentyl)benzene (i.e. the product of Step B, 1.82 g, 5.86 mmol, 1.0 eq.) in N,N-dimethylformamide (20 mL) was deoxygenated by bubbling $N_2$ through the reaction mixture for ~10 min. To this mixture was added copper(I) cyanide (1.57 g, 17.6 mmol, 3.0 eq.). The reaction was refluxed at 160° C. under nitrogen for 18 h. The reaction was cooled to ambient temperature and filtered through a pad of Celite® diatomaceous earth filter aid. The filtrate was diluted with ethyl acetate and washed several times with water, then once with brine. The organic layer was dried and concentrated in vacuo. The crude material was purified by column chromatography, eluting with 0 to 30% ethyl acetate in hexanes to afford the desired product (1.38 g).
$^1$H NMR (500 MHz, $CDCl_3$) δ 7.29-7.24 (m, 1H), 7.22-7.19 (m, 1H), 7.08-7.04 (m, 1H), 3.86 (s, 3H), 2.94-2.82 (m, 2H), 2.24-2.07 (m, 2H), 1.75-1.60 (m, 4H).

Step D: Preparation of 3-hydroxy-2-(5,5,5-trifluoropentyl)benzonitrile

A solution of 3-methoxy-2-(5,5,5-trifluoropentyl)benzonitrile (i.e. the product of Step C, 1.38 g, 5.36 mmol, 1.0 eq.) in dichloroethane (17 mL) was treated with boron tribromide (1.0 M in dichloromethane, 10.7 mL, 10.7 mmol, 2.0 eq.). The reaction mixture was heated to 60° C. for 18 h. The reaction was cooled to ambient temperature and quenched with saturated aqueous sodium bicarbonate. The organic phase was separated, dried and concentrated onto Celite® diatomaceous earth filter aid for purification by column chromatography, eluting with a gradient of 0 to 30% ethyl acetate in hexanes to afford the desired product (1.16 g).
$^1$H NMR (500 MHz, $CDCl_3$) δ 7.25-7.21 (m, 1H), 7.19-7.15 (m, 1H), 6.98-6.95 (m, 1H), 5.05-5.01 (m, 1H), 2.92-2.86 (m, 2H), 2.20-2.08 (m, 2H), 1.78-1.62 (m, 4H).

Step E: Preparation of 3-[(5-chloro-2-pyrimidinyl)oxy]-2-(5,5,5-trifluoropentyl)benzonitrile A mixture of 3-hydroxy-2-(5,5,5-trifluoropentyl)benzonitrile (i.e. the product of Step D, 1.16 g, 4.79 mmol, 1.0 eq.), 5-chloro-2-(methylsulfonyl)-pyrimidine (1.11 g, 5.75 mmol, 1.2 quiv) and potassium carbonate (0.993 g, 7.18 mmol, 1.5 eq.) in N,N-dimethylformamide (16 mL) was stirred at room temperature for 18 h. The reaction mixture was heavily diluted with ethyl acetate and washed several times with water, then once with brine. The organic phase was dried and concentrated onto Celite® diatomaceous filter aid for purification by column chromatography, eluting with a gradient of 0 to 30% ethyl acetate in hexanes to afford the desired product (1.65 g).

$^1$H NMR (500 MHz, CDCl$_3$) δ 8.52-8.48 (m, 2H), 7.61-7.56 (m, 1H), 7.42-7.36 (m, 1H), 7.35-7.31 (m, 1H), 2.87-2.78 (m, 2H), 2.16-2.00 (m, 2H), 1.74-1.64 (m, 2H), 1.63-1.54 (m, 2H).

By the procedures described herein together with methods known in the art, the following compounds of Tables 1 to 585 can be prepared. The following abbreviations are used in the Tables which follow: t means tertiary, s means secondary, n means normal, i means iso, c means cyclo, Me means methyl, Et means ethyl, Pr means propyl, Bu means butyl, i-Pr means isopropyl, Bu means butyl, c-Pr cyclopropyl, Ph means phenyl, OMe means methoxy, OEt means ethoxy, SMe means methylthio, NHMe methylamino, —CN means cyano, S(O)Me means methylsulfinyl, and S(O)$_2$Me means methylsulfonyl.

TABLE 1

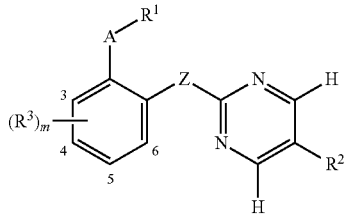

| R$^1$ | R$^1$ |
|---|---|
| butyl | 3,3,4,4,4-pentafluorobutoxy |
| tert-butyl | 2,2,3,3,3-pentafluoropropoxy |
| ethyl | 3,3,4,4-tetrafluorobutoxy |
| hexyl | 2,2,3,3-tetrafluoropropoxy |
| isobutyl | 3,3,3-trichloropropoxy |
| isopentyl | 4,4,4-trifluorobutoxy |
| methyl | 2,2,2-trifluoroethoxy |
| pentyl | 6,6,6-trifluorohexoxy |
| propyl | 4,4,4-trifluoro-2-methyl-butoxy |
| benzyl | 3,3,3-trifluoropropoxy |
| allyl | 4-bromobut-3-ynoxy |
| 3-buten-1-yl | 4-chlorobut-3-ynoxy |
| 3-methyl-2-buten-1-yl | 3-chloroprop-2-ynoxy |
| 3-methyl-3-buten-1-yl | 4,4-difluorobut-2-ynoxy |
| 4-methyl-3-penten-1-yl | 5,5,5-trifluoropent-2-ynoxy |
| 3-penten-1-yl | 5,5,5-trifluoropent-3-ynoxy |
| 3-butyn-1-yl | cyclobutylmethoxy |
| 4-methyl-2-pentyn-1-yl | cyclohexoxy |
| 3-pentyn-1-yl | cyclopentoxy |
| 2-propyn-1-yl | 2-cyclopropylethoxy |
| 5-hexyn-1-yl | cyclopropylmethoxy |
| 4-pentyn-1-yl | (2-bromo-2-chloro-cyclopropyl)methoxy |
| 3-bromopropyl | (2,2-dibromocyclopropyl)methoxy |
| 3-chlorobutyl | (2,2-dichloro-1-methyl-cyclopropyl)methoxy |
| 3-chloropropyl | (3,3-difluorocyclobutyl)methoxy |
| 4,4-difluorobutyl | 2-(2,2-difluorocyclopropyl)ethoxy |
| 2,2-difluoroethyl | (2,2-difluorocyclopropyl)methoxy |
| 3,3-difluoropropyl | 2-chloroethoxymethyl |
| 3,3,4,4,4-pentafluorobutyl | 2,3-dichloro-5-methoxy-pentyl |
| 2,2,3,3,3-pentafluoropropyl | 3,3-difluoro-5-methoxy-pentyl |
| 3,3,4,4-tetrafluorobutyl | 2-isopropoxyethyl |
| 2,2,3,3-tetrafluoropropyl | 2-methoxyethyl |
| 3,3,3-trichloropropyl | 5-methoxypentyl |
| 4,4,4-trifluorobutyl | 2-methoxypropyl |
| 2,2,2-trifluoroethyl | 1,1,2,2-tetrafluoroethoxymethyl |
| 6,6,6-trifluorohexyl | 2,2,2-trifluoroethoxymethyl |
| 4,4,4-trifluoro-2-methyl-butyl | 2-(trifluoromethoxy)ethyl |
| 3,3,3-trifluoropropyl | 2-isopropoxyethoxy |
| 4-bromo-3-buten-1-yl | 4-methoxybutoxy |
| 2-chloroallyl | 2-methoxyethoxy |

TABLE 1-continued

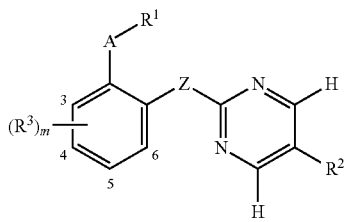

| R¹ | R¹ |
|---|---|
| 3-chloroallyl | 2-methoxypropoxy |
| 3-chloro-3-buten-1-yl | 4-cyanobutyl |
| 4-chloro-3-buten-1-yl | 3-cyano-1,2-dimethyl-propyl |
| 5,5-difluoro-3-penten-1-yl | 2-cyanoethyl |
| 4,4,4-trifluoro-2-buten-1-yl | 3-cyano-2-methyl-propyl |
| 5,5,5-trifluoro-3-methyl-2-penten-1-yl | cyanomethyl |
| 5,5,5-trifluoro-3-penten-1-yl | 5-cyanopentyl |
| 4-bromo-3-butyn-1-yl | 3-cyanopropyl |
| 3-butyn-1-yl | 4-cyanobutoxy |
| 4-chloro-3-butyn-1-yl | 3-cyano-1,2-dimethyl-propoxy |
| 3-chloro-2-propyn-1-yl | 2-cyanoethoxy |
| 4,4-difluoro-2-butyn-1-yl | cyanomethoxy |
| 5,5,5-trifluoro-1-methyl-2-pentyn-1-yl | 3-cyano-2-methyl-propoxy |
| 5,5,5-trifluoro-2-pentyn-1-yl | 5-cyanopentoxy |
| 5,5,5-trifluoro-3-pentyn-1-yl | 3-cyanopropoxy |
| 2-cyclobutylethyl | 2-(cyanomethoxy)ethyl |
| cyclohexyl | 3-(cyanomethoxy)-2-methyl-propyl |
| cyclopentylmethyl | cyanomethoxymethyl |
| 2-cyclopropylethyl | 1,2-dimethyl-3-nitro-propyl |
| 3-cyclopropylpropyl | 4-hydroxybutyl |
| (2,2-dimethylcyclopropyl)methyl | 3-hydroxy-1,2-dimethyl-propyl |
| (1-methylcyclopropyl)methyl | 2-hydroxyethyl |
| (2-methylcyclopentyl)methyl | 3-hydroxy-2-methyl-propyl |
| (2-bromo-2-chloro-cyclopropyl)methyl | hydroxymethyl |
| (2,2-dibromocyclopropyl)methyl | 5-hydroxypentyl |
| 2-(2,2-dichloro-1-methyl-cyclopropyl)ethyl | 3-hydroxypropyl |
| (2,2-dichloro-1-methyl-cyclopropyl)methyl | 2-methyl-3-nitro-propyl |
| 2-(3,3-difluorocyclobutyl)ethyl | 4-nitrobutyl |
| 2-(2,2-difluorocyclopropyl)ethyl | 2-nitroethyl |
| (2,2-difluorocyclopropyl)methyl | nitromethyl |
| butyl(methyl)amino | 5-nitropentyl |
| dimethylamino | 3-nitropropyl |
| ethyl(propyl)amino | butylthio |
| isopropyl(methyl)amino | tert-butylthio |
| isopropyl(propyl)amino | 1,3-dimethylbutylthio |
| methyl(propyl)amino | 3,3-dimethylbutylthio |
| 2-chloroethyl(2,2,2-trifluoroethyl)amino | ethylthio |
| 3-chloropropyl(methyl)amino | isopentylthio |
| methyl(2,2,2-trifluoroethyl)amino | methylthio |
| methyl(3,3,3-trifluoropropyl)amino | pentylthio |
| butylamino | propylthio |
| 3-chloropropylamino | 3-bromopropylthio |
| isopentylamino | 3-chlorobutylthio |
| propylamino | 3-chloropropylthio |
| 3,3,3-trifluoropropylamino | 2,2-difluoroethylthio |
| 1-piperidyl | 3,3,3-trichloropropylthio |
| 1-pyrrolidinyl | 4,4,4-trifluorobutylthio |
| butoxy | 2,2,2-trifluoroethylthio |
| tert-butoxy | 6,6,6-trifluorohexylthio |
| 1,3-dimethylbutoxy | 3,3,3-trifluoropropylthio |
| 3,3-dimethylbutoxy | cyclobutylmethylthio |
| ethoxy | cyclohexylthio |
| hexyl | cyclopentylthio |
| isopentyloxy | 2-cyclopropylethylthio |
| methoxy | cyclopropylmethylthio |
| propoxy | 2-chloroethylthiomethyl |
| allyloxy | 2,3-dichloro-5-methylthio-pentyl |
| 3-butenoxy | 3,3-difluoro-5-methylthio-pentyl |
| 3-methyl-2-butenoxy | 2-isopropylthioethyl |
| 3-methyl-3-butenoxy | 2-methylthioethyl |

TABLE 1-continued

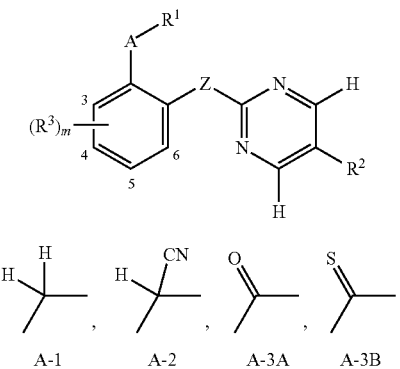

| $R^1$ | $R^1$ |
|---|---|
| 4-methyl-3-pentenoxy | 5-methylthiopentyl |
| 4-bromo-3-butenoxy | 2-methylthiopropyl |
| 2-chloroallyloxy | 1,1,2,2-tetrafluoroethylthiomethyl |
| 3-chloroallyloxy | 2,2,2-trifluoroethylthiomethyl |
| 3-chloro-3-butenoxy | 2-(trifluoromethylthio)ethyl |
| 4-chloro-3-butenoxy | bis(2-chloroethyl)aminooxy |
| 5,5-difluoro-3-pentenoxy | cyanomethoxy(methyl)amino |
| 4,4,4-trifluoro-2-butenoxy | diethylamino(methyl)amino |
| 5,5,5-trifluoro-3-methyl-2-pentenoxy | ethoxy(methyl)amino |
| 5,5,5-trifluoro-3-pentenoxy | ethoxy(2,2,2-trifluoroethyl)amino |
| 3-butynoxy | ethylamino(methyl)amino] |
| 5-hexynoxy | ethylamino(2,2,2-trifluoroethyl)amino |
| 4-methyl-2-pentynoxy | ethyl(methy)amino]-(2,2,2-trifluoroethyl)amino |
| 3-pentynoxy | ethyl(3,3,3-trifluoropropyl)amino]-methyl-amino |
| 4-pentynoxy | isobutyl(methyl)amino]oxy |
| 2-propynoxy | 2-methoxyethoxy(methyl)amino |
| 3-bromopropoxy | methyl(propyl)amino]oxy |
| 3-chlorobutoxy | methyl(2,2,2-trifluoroethoxy)amino |
| 3-chloropropoxy | methyl(2,2,2-trifluoroethyl)amino]oxy |
| 4,4-difluorobutoxy | methyl(3,3,3-trifluoropropoxy)amino |
| 2,2-difluoroethoxy | methyl-(3,3,3-trifluoropropylamino)amino |
| 3,3-difluoropropoxy | |

$R^2 = F$, $(R^3)_m = 3$-F, $Z = O$ and $A = A$-3A

The present disclosure also includes Tables 2 through 292. Each Table is constructed in the same manner as Table 1 above, except that the row heading in Table 1 (i.e. "$R^2$=F, $(R^3)_m$=3-F, Z=O and A=A-3A") is replaced with the respective row heading shown below. For example, the first entry in Table 2 is a compound of Formula 1 wherein $R^2$ is Cl, $(R^3)_m$ is 3-F, Z is O, A is A-3A and $R^1$ is butyl. Tables 3 through 292 are constructed similarly.

| Table | $R^2$ | $(R^3)_m$ | Z | A |
|---|---|---|---|---|
| 2 | Cl | 3-F | O | A-3A |
| 3 | Br | 3-F | O | A-3A |
| 4 | I | 3-F | O | A-3A |
| 5 | $CF_3$ | 3-F | O | A-3A |
| 6 | OMe | 3-F | O | A-3A |
| 7 | Me | 3-F | O | A-3A |
| 8 | F | 3-Cl | O | A-3A |
| 9 | Cl | 3-Cl | O | A-3A |
| 10 | Br | 3-Cl | O | A-3A |
| 11 | I | 3-Cl | O | A-3A |
| 12 | $CF_3$ | 3-Cl | O | A-3A |
| 13 | OMe | 3-Cl | O | A-3A |
| 14 | Me | 3-Cl | O | A-3A |
| 15 | F | 3-Br | O | A-3A |
| 16 | Cl | 3-Br | O | A-3A |
| 17 | Br | 3-Br | O | A-3A |
| 18 | I | 3-Br | O | A-3A |
| 19 | $CF_3$ | 3-Br | O | A-3A |
| 20 | OMe | 3-Br | O | A-3A |
| 21 | Me | 3-Br | O | A-3A |
| 22 | F | 3-I | O | A-3A |
| 23 | Cl | 3-I | O | A-3A |
| 24 | Br | 3-I | O | A-3A |
| 25 | I | 3-I | O | A-3A |
| 26 | $CF_3$ | 3-I | O | A-3A |
| 27 | OMe | 3-I | O | A-3A |
| 28 | Me | 3-I | O | A-3A |
| 29 | F | 3-CN | O | A-3A |
| 30 | Cl | 3-CN | O | A-3A |
| 31 | Br | 3-CN | O | A-3A |
| 32 | I | 3-CN | O | A-3A |
| 33 | $CF_3$ | 3-CN | O | A-3A |
| 34 | OMe | 3-CN | O | A-3A |
| 35 | Me | 3-CN | O | A-3A |
| 36 | F | 3-$CF_3$ | O | A-3A |
| 37 | Cl | 3-$CF_3$ | O | A-3A |
| 38 | Br | 3-$CF_3$ | O | A-3A |
| 39 | I | 3-$CF_3$ | O | A-3A |
| 40 | $CF_3$ | 3-$CF_3$ | O | A-3A |
| 41 | OMe | 3-$CF_3$ | O | A-3A |
| 42 | Me | 3-$CF_3$ | O | A-3A |
| 43 | F | 4-Cl | O | A-3A |
| 44 | Cl | 4-Cl | O | A-3A |
| 45 | Br | 4-Cl | O | A-3A |
| 46 | I | 4-Cl | O | A-3A |

| Table | R² | (R³)ₘ | Z | A |
|---|---|---|---|---|
| 47 | CF₃ | 4-Cl | O | A-3A |
| 48 | OMe | 4-Cl | O | A-3A |
| 49 | Me | 4-Cl | O | A-3A |
| 50 | F | 5-Cl | O | A-3A |
| 51 | Cl | 5-Cl | O | A-3A |
| 52 | Br | 5-Cl | O | A-3A |
| 53 | I | 5-Cl | O | A-3A |
| 54 | CF₃ | 5-Cl | O | A-3A |
| 55 | OMe | 5-Cl | O | A-3A |
| 56 | Me | 5-Cl | O | A-3A |
| 57 | F | 6-Cl | O | A-3A |
| 58 | Cl | 6-Cl | O | A-3A |
| 59 | Br | 6-Cl | O | A-3A |
| 60 | I | 6-Cl | O | A-3A |
| 61 | CF₃ | 6-Cl | O | A-3A |
| 62 | OMe | 6-Cl | O | A-3A |
| 63 | Me | 6-Cl | O | A-3A |
| 64 | F | 3-Br, 4-F | O | A-3A |
| 65 | Cl | 3-Br, 4-F | O | A-3A |
| 66 | Br | 3-Br, 4-F | O | A-3A |
| 67 | I | 3-Br, 4-F | O | A-3A |
| 68 | CF₃ | 3-Br, 4-F | O | A-3A |
| 69 | OMe | 3-Br, 4-F | O | A-3A |
| 70 | Me | 3-Br, 4-F | O | A-3A |
| 71 | F | 3-F, 4-F | O | A-3A |
| 72 | Cl | 3-F, 4-F | O | A-3A |
| 73 | Br | 3-F, 4-F | O | A-3A |
| 74 | I | 3-F, 4-F | O | A-3A |
| 75 | CF₃ | 3-F, 4-F | O | A-3A |
| 76 | OMe | 3-F, 4-F | O | A-3A |
| 77 | Me | 3-F, 4-F | O | A-3A |
| 78 | F | 3-Cl, 4-F | O | A-3A |
| 79 | Cl | 3-Cl, 4-F | O | A-3A |
| 80 | Br | 3-Cl, 4-F | O | A-3A |
| 81 | I | 3-Cl, 4-F | O | A-3A |
| 82 | CF₃ | 3-Cl, 4-F | O | A-3A |
| 83 | OMe | 3-Cl, 4-F | O | A-3A |
| 84 | Me | 3-Cl, 4-F | O | A-3A |
| 85 | F | 3-Br | S | A-3A |
| 86 | Cl | 3-Br | S | A-3A |
| 87 | Br | 3-Br | S | A-3A |
| 88 | I | 3-Br | S | A-3A |
| 89 | CF₃ | 3-Br | S | A-3A |
| 90 | OMe | 3-Br | S | A-3A |
| 91 | Me | 3-Br | S | A-3A |
| 92 | F | 3-Cl | S | A-3A |
| 93 | Cl | 3-Cl | S | A-3A |
| 94 | Br | 3-Cl | S | A-3A |
| 95 | I | 3-Cl | S | A-3A |
| 96 | CF₃ | 3-Cl | S | A-3A |
| 97 | OMe | 3-Cl | S | A-3A |
| 98 | Me | 3-Cl | S | A-3A |
| 99 | Cl | 3-F | O | A-3B |
| 100 | Br | 3-F | O | A-3B |
| 101 | I | 3-F | O | A-3B |
| 102 | CF₃ | 3-F | O | A-3B |
| 103 | OMe | 3-F | O | A-3B |
| 104 | Me | 3-F | O | A-3B |
| 105 | F | 3-Cl | O | A-3B |
| 106 | Cl | 3-Cl | O | A-3B |
| 107 | Br | 3-Cl | O | A-3B |
| 108 | I | 3-Cl | O | A-3B |
| 109 | CF₃ | 3-Cl | O | A-3B |
| 110 | OMe | 3-Cl | O | A-3B |
| 111 | Me | 3-Cl | O | A-3B |
| 112 | F | 3-Br | O | A-3B |
| 113 | Cl | 3-Br | O | A-3B |
| 114 | Br | 3-Br | O | A-3B |
| 115 | I | 3-Br | O | A-3B |
| 116 | CF₃ | 3-Br | O | A-3B |
| 117 | OMe | 3-Br | O | A-3B |
| 118 | Me | 3-Br | O | A-3B |
| 119 | F | 3-I | O | A-3B |
| 120 | Cl | 3-I | O | A-3B |
| 121 | Br | 3-I | O | A-3B |
| 122 | I | 3-I | O | A-3B |
| 123 | CF₃ | 3-I | O | A-3B |
| 124 | OMe | 3-I | O | A-3B |
| 125 | Me | 3-I | O | A-3B |
| 126 | F | 3-CN | O | A-3B |
| 127 | Cl | 3-CN | O | A-3B |
| 128 | Br | 3-CN | O | A-3B |
| 129 | I | 3-CN | O | A-3B |
| 130 | CF₃ | 3-CN | O | A-3B |
| 131 | OMe | 3-CN | O | A-3B |
| 132 | Me | 3-CN | O | A-3B |
| 133 | F | 3-CF₃ | O | A-3B |
| 134 | Cl | 3-CF₃ | O | A-3B |
| 135 | Br | 3-CF₃ | O | A-3B |
| 136 | I | 3-CF₃ | O | A-3B |
| 137 | CF₃ | 3-CF₃ | O | A-3B |
| 138 | OMe | 3-CF₃ | O | A-3B |
| 139 | Me | 3-CF₃ | O | A-3B |
| 140 | F | 4-Cl | O | A-3B |
| 141 | Cl | 4-Cl | O | A-3B |
| 142 | Br | 4-Cl | O | A-3B |
| 143 | I | 4-Cl | O | A-3B |
| 144 | CF₃ | 4-Cl | O | A-3B |
| 145 | OMe | 4-Cl | O | A-3B |
| 146 | Me | 4-Cl | O | A-3B |
| 147 | F | 5-Cl | O | A-3B |
| 148 | Cl | 5-Cl | O | A-3B |
| 149 | Br | 5-Cl | O | A-3B |
| 150 | I | 5-Cl | O | A-3B |
| 151 | CF₃ | 5-Cl | O | A-3B |
| 152 | OMe | 5-Cl | O | A-3B |
| 153 | Me | 5-Cl | O | A-3B |
| 154 | F | 6-Cl | O | A-3B |
| 155 | Cl | 6-Cl | O | A-3B |
| 156 | Br | 6-Cl | O | A-3B |
| 157 | I | 6-Cl | O | A-3B |
| 158 | CF₃ | 6-Cl | O | A-3B |
| 159 | OMe | 6-Cl | O | A-3B |
| 160 | Me | 6-Cl | O | A-3B |
| 161 | F | 3-Br, 4-F | O | A-3B |
| 162 | Cl | 3-Br, 4-F | O | A-3B |
| 163 | Br | 3-Br, 4-F | O | A-3B |
| 164 | I | 3-Br, 4-F | O | A-3B |
| 165 | CF₃ | 3-Br, 4-F | O | A-3B |
| 166 | OMe | 3-Br, 4-F | O | A-3B |
| 167 | Me | 3-Br, 4-F | O | A-3B |
| 168 | F | 3-F, 4-F | O | A-3B |
| 169 | Cl | 3-F, 4-F | O | A-3B |
| 170 | Br | 3-F, 4-F | O | A-3B |
| 171 | I | 3-F, 4-F | O | A-3B |
| 172 | CF₃ | 3-F, 4-F | O | A-3B |
| 173 | OMe | 3-F, 4-F | O | A-3B |
| 174 | Me | 3-F, 4-F | O | A-3B |
| 175 | F | 3-Cl, 4-F | O | A-3B |
| 176 | Cl | 3-Cl, 4-F | O | A-3B |
| 177 | Br | 3-Cl, 4-F | O | A-3B |
| 178 | I | 3-Cl, 4-F | O | A-3B |
| 179 | CF₃ | 3-Cl, 4-F | O | A-3B |
| 180 | OMe | 3-Cl, 4-F | O | A-3B |
| 181 | Me | 3-Cl, 4-F | O | A-3B |
| 182 | F | 3-Br | S | A-3B |
| 183 | Cl | 3-Br | S | A-3B |
| 184 | Br | 3-Br | S | A-3B |
| 185 | I | 3-Br | S | A-3B |
| 186 | CF₃ | 3-Br | S | A-3B |
| 187 | OMe | 3-Br | S | A-3B |
| 188 | Me | 3-Br | S | A-3B |
| 189 | F | 3-Cl | S | A-3B |
| 190 | Cl | 3-Cl | S | A-3B |
| 191 | Br | 3-Cl | S | A-3B |
| 192 | I | 3-Cl | S | A-3B |
| 193 | CF₃ | 3-Cl | S | A-3B |
| 194 | OMe | 3-Cl | S | A-3B |
| 195 | Me | 3-Cl | S | A-3B |
| 196 | Cl | 3-F | O | A-1 |

| Table | R² | (R³)ₘ | Z | A |
|---|---|---|---|---|
| 197 | Br | 3-F | O | A-1 |
| 198 | I | 3-F | O | A-1 |
| 199 | CF₃ | 3-F | O | A-1 |
| 200 | OMe | 3-F | O | A-1 |
| 201 | Me | 3-F | O | A-1 |
| 202 | F | 3-Cl | O | A-1 |
| 203 | Cl | 3-Cl | O | A-1 |
| 204 | Br | 3-Cl | O | A-1 |
| 205 | I | 3-Cl | O | A-1 |
| 206 | CF₃ | 3-Cl | O | A-1 |
| 207 | OMe | 3-Cl | O | A-1 |
| 208 | Me | 3-Cl | O | A-1 |
| 209 | F | 3-Br | O | A-1 |
| 210 | Cl | 3-Br | O | A-1 |
| 211 | Br | 3-Br | O | A-1 |
| 212 | I | 3-Br | O | A-1 |
| 213 | CF₃ | 3-Br | O | A-1 |
| 214 | OMe | 3-Br | O | A-1 |
| 215 | Me | 3-Br | O | A-1 |
| 216 | F | 3-I | O | A-1 |
| 217 | Cl | 3-I | O | A-1 |
| 218 | Br | 3-I | O | A-1 |
| 219 | I | 3-I | O | A-1 |
| 220 | CF₃ | 3-I | O | A-1 |
| 221 | OMe | 3-I | O | A-1 |
| 222 | Me | 3-I | O | A-1 |
| 223 | F | 3-CN | O | A-1 |
| 224 | Cl | 3-CN | O | A-1 |
| 225 | Br | 3-CN | O | A-1 |
| 226 | I | 3-CN | O | A-1 |
| 227 | CF₃ | 3-CN | O | A-1 |
| 228 | OMe | 3-CN | O | A-1 |
| 229 | Me | 3-CN | O | A-1 |
| 230 | F | 3-CF₃ | O | A-1 |
| 231 | Cl | 3-CF₃ | O | A-1 |
| 232 | Br | 3-CF₃ | O | A-1 |
| 233 | I | 3-CF₃ | O | A-1 |
| 234 | CF₃ | 3-CF₃ | O | A-1 |
| 235 | OMe | 3-CF₃ | O | A-1 |
| 236 | Me | 3-CF₃ | O | A-1 |
| 237 | F | 4-Cl | O | A-1 |
| 238 | Cl | 4-Cl | O | A-1 |
| 239 | Br | 4-Cl | O | A-1 |
| 240 | I | 4-Cl | O | A-1 |
| 241 | CF₃ | 4-Cl | O | A-1 |
| 242 | OMe | 4-Cl | O | A-1 |
| 243 | Me | 4-Cl | O | A-1 |
| 244 | F | 5-Cl | O | A-1 |
| 245 | Cl | 5-Cl | O | A-1 |
| 246 | Br | 5-Cl | O | A-1 |
| 247 | I | 5-Cl | O | A-1 |
| 248 | CF₃ | 5-Cl | O | A-1 |
| 249 | OMe | 5-Cl | O | A-1 |
| 250 | Me | 5-Cl | O | A-1 |
| 251 | F | 6-Cl | O | A-1 |
| 252 | Cl | 6-Cl | O | A-1 |
| 253 | Br | 6-Cl | O | A-1 |
| 254 | I | 6-Cl | O | A-1 |
| 255 | CF₃ | 6-Cl | O | A-1 |
| 256 | OMe | 6-Cl | O | A-1 |
| 257 | Me | 6-Cl | O | A-1 |
| 258 | F | 3-Br, 4-F | O | A-1 |
| 259 | Cl | 3-Br, 4-F | O | A-1 |
| 260 | Br | 3-Br, 4-F | O | A-1 |
| 261 | I | 3-Br, 4-F | O | A-1 |
| 262 | CF₃ | 3-Br, 4-F | O | A-1 |
| 263 | OMe | 3-Br, 4-F | O | A-1 |
| 264 | Me | 3-Br, 4-F | O | A-1 |
| 265 | F | 3-F, 4-F | O | A-1 |
| 266 | Cl | 3-F, 4-F | O | A-1 |
| 267 | Br | 3-F, 4-F | O | A-1 |
| 268 | I | 3-F, 4-F | O | A-1 |
| 269 | CF₃ | 3-F, 4-F | O | A-1 |
| 270 | OMe | 3-F, 4-F | O | A-1 |
| 271 | Me | 3-F, 4-F | O | A-1 |
| 272 | F | 3-Cl, 4-F | O | A-1 |
| 273 | Cl | 3-Cl, 4-F | O | A-1 |
| 274 | Br | 3-Cl, 4-F | O | A-1 |
| 275 | I | 3-Cl, 4-F | O | A-1 |
| 276 | CF₃ | 3-Cl, 4-F | O | A-1 |
| 277 | OMe | 3-Cl, 4-F | O | A-1 |
| 278 | Me | 3-Cl, 4-F | O | A-1 |
| 279 | F | 3-Br | S | A-1 |
| 280 | Cl | 3-Br | S | A-1 |
| 281 | Br | 3-Br | S | A-1 |
| 282 | I | 3-Br | S | A-1 |
| 283 | CF₃ | 3-Br | S | A-1 |
| 284 | OMe | 3-Br | S | A-1 |
| 285 | Me | 3-Br | S | A-1 |
| 286 | F | 3-Cl | S | A-1 |
| 287 | Cl | 3-Cl | S | A-1 |
| 288 | Br | 3-Cl | S | A-1 |
| 289 | I | 3-Cl | S | A-1 |
| 290 | CF₃ | 3-Cl | S | A-1 |
| 291 | OMe | 3-Cl | S | A-1 |
| 292 | Me | 3-Cl | S | A-1 |

TABLE 293

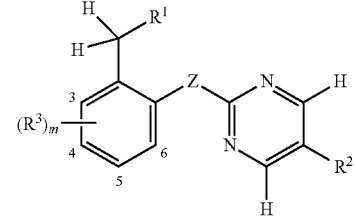

| R¹ | R¹ |
|---|---|
| butylsulfinyl | 3,3-difluoropropoxy |
| tert-butylsulfinyl | ethylsulfonyl |
| 1,3-dimethylbutylsulfinyl | isopentylsulfonyl |
| 3,3-dimethylbutylsulfinyl | methylsulfonyl |
| ethylsulfinyl | pentylsulfonyl |
| isopentylsulfinyl | propylsulfonyl |
| methylsulfinyl | 3-bromopropylsulfonyl |
| pentylsulfinyl | 3-chlorobutylsulfonyl |
| propylsulfinyl | 3-chloropropylsulfonyl |
| 3-bromopropylsulfinyl | 2,2-difluoroethylsulfonyl |
| 3-chlorobutylsulfinyl | 3,3,3-trifluoropropylsulfonyl |

TABLE 293-continued

| R¹ | R¹ |
|---|---|
| 3-chloropropylsulfinyl | 3,3,3-trichloropropylsulfonyl |
| 2,2-difluoroethylsulfinyl | 4,4,4-trifluorobutylsulfonyl |
| 3,3,3-trifluoropropylsulfinyl | 2,2,2-trifluoroethylsulfonyl |
| 3,3,3-trichloropropylsulfinyl | 6,6,6-trifluorohexylsulfonyl |
| 4,4,4-trifluorobutylsulfinyl | cyclobutylmethylsulfonyl |
| 2,2,2-trifluoroethylsulfinyl | cyclohexylsulfonyl |
| 6,6,6-trifluorohexylsulfinyl | cyclopentylsulfonyl |
| 1,3-dimethylbutylsulfinyl | 2-cyclopropylethylsulfonyl |
| 3,3-dimethylbutylsulfinyl | cyclopropylmethylsulfonyl |

$R^2 = F$, $(R^3)_m = 3\text{-}F$ and $Z = O$

The present disclosure also includes Tables 294 through 390. Each Table is constructed in the same manner as Table 293 above, except that the row heading in Table 293 (i.e. "$R^2=F$, $(R^3)_m=3\text{-}F$ and $Z=O$") is replaced with the respective row heading shown below. For example, the header row in Table 294 is "$R^2=Cl$, $(R^3)_m=3\text{-}F$ and $Z=O$" and the first entry in Table 294 is a compound of Formula 1 wherein $R^1$=butylsulfinyl, $R^2$=Cl, $(R^3)_m=3\text{-}F$ and $Z=O$. Tables 295 through 390 are constructed similarly.

Header Row

| Table | R² | (R³)ₘ | Z |
|---|---|---|---|
| 294 | Cl | 3-F | O |
| 295 | Br | 3-F | O |
| 296 | I | 3-F | O |
| 297 | CF₃ | 3-F | O |
| 298 | OMe | 3-F | O |
| 299 | Me | 3-F | O |
| 300 | F | 3-Cl | O |
| 301 | Cl | 3-Cl | O |
| 302 | Br | 3-Cl | O |
| 303 | I | 3-Cl | O |
| 304 | CF₃ | 3-Cl | O |
| 305 | OMe | 3-Cl | O |
| 306 | Me | 3-Cl | O |
| 307 | F | 3-Br | O |
| 308 | Cl | 3-Br | O |
| 309 | Br | 3-Br | O |
| 310 | I | 3-Br | O |
| 311 | CF₃ | 3-Br | O |
| 312 | OMe | 3-Br | O |
| 313 | Me | 3-Br | O |
| 314 | F | 3-I | O |
| 315 | Cl | 3-I | O |
| 316 | Br | 3-I | O |
| 317 | I | 3-I | O |
| 318 | CF₃ | 3-I | O |
| 319 | OMe | 3-I | O |
| 320 | Me | 3-I | O |
| 321 | F | 3-CN | O |
| 322 | Cl | 3-CN | O |
| 323 | Br | 3-CN | O |
| 324 | I | 3-CN | O |
| 325 | CF₃ | 3-CN | O |
| 326 | OMe | 3-CN | O |
| 327 | Me | 3-CN | O |
| 328 | F | 3-CF₃ | O |
| 329 | Cl | 3-CF₃ | O |
| 330 | Br | 3-CF₃ | O |
| 331 | I | 3-CF₃ | O |
| 332 | CF₃ | 3-CF₃ | O |
| 333 | OMe | 3-CF₃ | O |
| 334 | Me | 3-CF₃ | O |
| 335 | F | 4-Cl | O |
| 336 | Cl | 4-Cl | O |
| 337 | Br | 4-Cl | O |
| 338 | I | 4-Cl | O |
| 339 | CF₃ | 4-Cl | O |
| 340 | OMe | 4-Cl | O |
| 341 | Me | 4-Cl | O |
| 342 | F | 5-Cl | O |
| 343 | Cl | 5-Cl | O |
| 344 | Br | 5-Cl | O |
| 345 | I | 5-Cl | O |
| 346 | CF₃ | 5-Cl | O |
| 347 | OMe | 5-Cl | O |
| 348 | Me | 5-Cl | O |
| 349 | F | 6-Cl | O |
| 350 | Cl | 6-Cl | O |
| 351 | Br | 6-Cl | O |
| 352 | I | 6-Cl | O |
| 353 | CF₃ | 6-Cl | O |
| 354 | OMe | 6-Cl | O |
| 355 | Me | 6-Cl | O |
| 356 | F | 3-Br, 4-F | O |
| 357 | Cl | 3-Br, 4-F | O |
| 358 | Br | 3-Br, 4-F | O |
| 359 | I | 3-Br, 4-F | O |
| 360 | CF₃ | 3-Br, 4-F | O |
| 361 | OMe | 3-Br, 4-F | O |
| 362 | Me | 3-Br, 4-F | O |
| 363 | F | 3-F, 4-F | O |
| 364 | Cl | 3-F, 4-F | O |
| 365 | Br | 3-F, 4-F | O |
| 366 | I | 3-F, 4-F | O |
| 367 | CF₃ | 3-F, 4-F | O |
| 368 | OMe | 3-F, 4-F | O |
| 369 | Me | 3-F, 4-F | O |
| 370 | F | 3-Cl, 4-F | O |
| 371 | Cl | 3-Cl, 4-F | O |
| 372 | Br | 3-Cl, 4-F | O |
| 373 | I | 3-Cl, 4-F | O |
| 374 | CF₃ | 3-Cl, 4-F | O |
| 375 | OMe | 3-Cl, 4-F | O |
| 376 | Me | 3-Cl, 4-F | O |
| 377 | F | 3-Br | S |
| 378 | Cl | 3-Br | S |
| 379 | Br | 3-Br | S |
| 380 | I | 3-Br | S |
| 381 | CF₃ | 3-Br | S |
| 382 | OMe | 3-Br | S |
| 383 | Me | 3-Br | S |
| 384 | F | 3-Cl | S |
| 385 | Cl | 3-Cl | S |
| 386 | Br | 3-Cl | S |
| 387 | I | 3-Cl | S |
| 388 | CF₃ | 3-Cl | S |
| 389 | OMe | 3-Cl | S |
| 390 | Me | 3-Cl | S |

TABLE 391

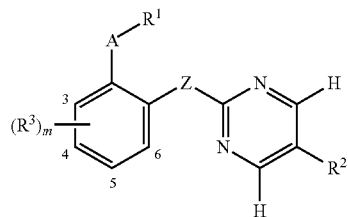

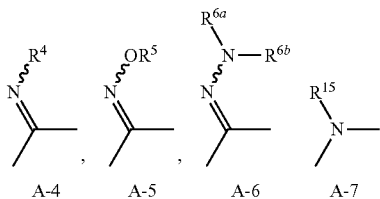

A-4, A-5, A-6, A-7

| A | A |
|---|---|
| A = A-4; R⁴ = 3-bromopropyl | A = A-5; R⁵ = 4-chloro-3-butyn-1-yl |
| A = A-4; R⁴ = tert-butyl) | A = A-5; R⁵ = 3-chloro-2-propyn-1-yl |
| A = A-4; R⁴ = 3-chlorobutyl | A = A-5; R⁵ = 4,4-difluoro-2-butyn-1-yl |
| A = A-4; R⁴ = 3-chloropropyl | A = A-5; R⁵ = 5,5,5-trifluoro-1-methyl-2-pentyn-1-yl |
| A = A-4; R⁴ = 4,4-difluorobutyl | A = A-5; R⁵ = 5,5,5-trifluoro-2-pentyn-1-yl |
| A = A-4; R⁴ = 2,2-difluoroethyl | A = A-5; R⁵ = 5,5,5-trifluoro-3-pentyn-1-yl |
| A = A-4; R⁴ = 3,3-difluoropropyl | A = A-5; R⁵ = 2-cyclobutylethyl |
| A = A-4; R⁴ = ethyl | A = A-5; R⁵ = cyclohexyl |
| A = A-4; R⁴ = hexyl | A = A-5; R⁵ = cyclopentylmethyl |
| A = A-4; R⁴ = isobutyl | A = A-5; R⁵ = 2-cyclopropylethyl |
| A = A-4; R⁴ = isopentyl | A = A-5; R⁵ = 3-cyclopropylpropyl |
| A = A-4; R⁴ = methyl | A = A-5; R⁵ = (2,2-dimethylcyclopropyl)methyl |
| A = A-4; R⁴ = 3,3,4,4,4-pentafluorobutyl | A = A-5; R⁵ = (1-methylcyclopropyl)methyl |
| A = A-4; R⁴ = 2,2,3,3,3-pentafluoropropyl | A = A-5; R⁵ = (2-methylcyclopentyl)methyl |
| A = A-4; R⁴ = pentyl | A = A-5; R⁵ = (2-bromo-2-chloro-cyclopropyl)methyl |
| A = A-4; R⁴ = propyl | A = A-5; R⁵ = (2,2-dibromocyclopropyl)methyl |
| A = A-4; R⁴ = 3,3,4,4-tetrafluorobutyl | A = A-5; R⁵ = 2-(2,2-dichloro-1-methyl-cyclopropyl)ethyl |
| A = A-4; R⁴ = 2,2,3,3-tetrafluoropropyl | A = A-5; R⁵ = (2,2-dichloro-1-methyl-cyclopropyl)methyl |
| A = A-4; R⁴ = 3,3,3-trichloropropyl | A = A-5; R⁵ = 2-(3,3-difluorocyclobutyl)ethyl |
| A = A-4; R⁴ = 4,4,4-trifluorobutyl | A = A-5; R⁵ = 2-(2,2-difluorocyclopropyl)ethyl |
| A = A-4; R⁴ = 2,2,2-trifluoroethyl | A = A-5; R⁵ = (2,2-difluorocyclopropyl)methyl |
| A = A-4; R⁴ = 6,6,6-trifluorohexyl | A = A-5; R⁵ = 2-chloroethoxymethyl |
| A = A-4; R⁴ = 4,4,4-trifluoro-2-methyl-butyl | A = A-5; R⁵ = 2,3-dichloro-5-methoxy-pentyl |
| A = A-4; R⁴ = 3,3,3-trifluoropropyl | A = A-5; R⁵ = 3,3-difluoro-5-methoxy-pentyl |
| A = A-4; R⁴ = 3-bromopropyl | A = A-5; R⁵ = 2-isopropoxyethyl |
| A = A-5; R⁵ = butyl | A = A-5; R⁵ = 2-methoxyethyl |
| A=A-5; R⁵ = tert-butyl | A = A-5; R⁵ = 5-methoxypentyl |
| A = A-5; R⁵ = ethyl | A = A-5; R⁵ = 2-methoxypropyl |
| A = A-5; R⁵ = hexyl | A = A-5; R⁵ = 1,1,2,2-tetrafluoroethoxymethyl |
| A = A-5; R⁵ = isobutyl | A = A-5; R⁵ = 2,2,2-trifluoroethoxymethyl |
| A = A-5; R⁵ = isopentyl | A = A-5; R⁵ = 2-(trifluoromethoxy)ethyl |
| A = A-5; R⁵ = pentyl | A = A-5; R⁵ = 4-cyanobutyl |
| A = A-5; R⁵ = propyl | A = A-5; R⁵ = 3-cyano-1,2-dimethyl-propyl |
| A = A-5; R⁵ = benzyl) | A = A-5; R⁵ = 2-cyanoethyl |
| A = A-5; R⁵ = allyl | A = A-5; R⁵ = 3-cyano-2-methyl-propyl |
| A = A-5; R⁵ = 3-buten-1-yl | A = A-5; R⁵ = cyanomethyl |
| A = A-5; R⁵ = 3-methy-2-1buten-1-yl | A = A-5; R⁵ = 5-cyanopentyl |
| A = A-5; R⁵ = 3-methyl-3-buten-1-yl | A = A-5; R⁵ = 3-cyanopropyl |
| A = A-5; R⁵ = 4-methyl-3-penten-1-yl | A = A-5; R⁵ = 2-(cyanomethoxy)ethyl |
| A = A-5; R⁵ = 3-penten-1-yl | A = A-5; R⁵ = 3-(cyanomethoxy)-2-methyl-propyl |
| A = A-5; R⁵ = 3-butyn-1-yl | A = A-5; R⁵ = cyanomethoxymethyl |
| A = A-5; R⁵ = 4-methyl-2-pentyn-1-yl | A = A-5; R⁵ = 1,2-dimethyl-3-nitro-propyl |
| A = A-5; R⁵ = 3-pentyn-1-yl | A = A-5; R⁵ = 4-hydroxybutyl |
| A = A-5; R⁵ = 2-propyn-1-yl | A = A-5; R⁵ = 3-hydroxy-1,2-dimethyl-propyl |
| A = A-5; R⁵ = 5-hexyn-1-yl | A = A-5; R⁵ = 3-hydroxy-2-methyl-propyl |
| A = A-5; R⁵ = 4-pentyn-1-yl | A = A-5; R⁵ = hydroxymethyl |
| A = A-5; R⁵ = 3-bromopropyl | A = A-5; R⁵ = 5-hydroxypentyl |
| A = A-5; R⁵ = 3-chlorobutyl | A = A-5; R⁵ = 3-hydroxypropyl |
| A = A-5; R⁵ = 3-chloropropyl | A = A-5; R⁵ = 2-methyl-3-nitro-propyl |
| A = A-5; R⁵ = 4,4-difluorobutyl | A = A-5; R⁵ = 4-nitrobutyl |
| A = A-5; R⁵ = 2,2-difluoroethyl | A = A-5; R⁵ = 2-nitroethyl |
| A = A-5; R⁵ = 3,3-difluoropropyl | A = A-5; R⁵ = nitromethyl |
| A = A-5; R⁵ = 3,3,4,4-pentafluorobutyl | A = A-5; R⁵ = 5-nitropentyl |
| A = A-5; R⁵ = 2,2,3,3,3-pentafluoropropyl | A = A-5; R⁵ = 3-nitropropyl |
| A = A-5; R⁵ = 3,3,4,4-tetrafluorobutyl | A = A-5; R⁵ = 2-chloroethylthiomethyl |
| A = A-5; R⁵ = 2,2,3,3-tetrafluoropropyl | A = A-5; R⁵ = 2,3-dichloro-5-methylthio-pentyl |

TABLE 391-continued

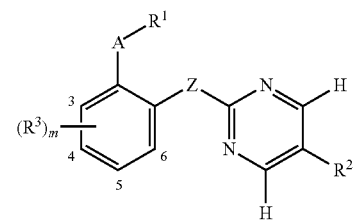

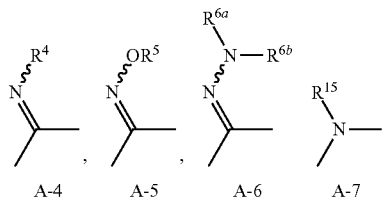

| A |
|---|
| A = A-5; $R^5$ = 3,3,3-trichloropropyl |
| A = A-5; $R^5$ = 4,4,4-trifluorobutyl |
| A = A-5; $R^5$ = 2,2,2-trifluoroethyl |
| A = A-5; $R^5$ = 6,6,6-trifluorohexyl |
| A = A-5; $R^5$ = 4,4,4-trifluoro-2-methyl-butyl |
| A = A-5; $R^5$ = 3,3,3-trifluoropropyl |
| A = A-5; $R^5$ = 4-bromo-3-buten-1-yl |
| A = A-5; $R^5$ = 2-chloroallyl |
| A = A-5; $R^5$ = 3-chloroallyl |
| A = A-5; $R^5$ = 3-chloro-3-buten-1-yl |
| A = A-5; $R^5$ = 4-chloro-3-buten-1-yl |
| A = A-5; $R^5$ = 5,5-difluoro-3-penten-1-yl |
| A = A-5; $R^5$ = 4,4,4-trifluoro-2-buten-1-yl |
| A = A-5; $R^5$ = 5,5,5-trifluoro-3-methyl-2-penten-1-yl |
| A = A-5; $R^5$ = 5,5,5-trifluoro-3-penten-1-yl |
| A = A-5; $R^5$ = 4-bromo-3-butyn-1-yl |
| A = A-5; $R^5$ = 3-butyn-1-yl |
| A = A-7; $R^{15}$ = isopentyl |
| A = A-7; $R^{15}$ = pentyl |
| A = A-7; $R^{15}$ = propyl |
| A = A-7; $R^{15}$ = H |

| A |
|---|
| A = A-5; $R^5$ = 3,3-difluoro-5-methylthio-pentyl |
| A = A-5; $R^5$ = 2-isopropylthioethyl |
| A = A-5; $R^5$ = 2-methylthioethyl |
| A = A-5; $R^5$ = 5-methylthiopentyl |
| A = A-5; $R^5$ = 2-methylthiopropyl |
| A = A-5; $R^5$ = 1,1,2,2-tetrafluoroethylthiomethyl |
| A = A-5; $R^5$ = 2,2,2-trifluoroethylthiomethyl |
| A = A-5; $R^5$ = 2-(trifluoromethylthio)ethyl |
| A = A-6; $R^{6a}$ = Me); $R^{6b}$ = butyl |
| A = A-6; $R^{6a}$ = Me; $R^{6b}$ = tert-butyl |
| A = A-6; $R^{6a}$ = Me; $R^{6b}$ = ethyl |
| A = A-6; $R^{6a}$ = Me; $R^{6b}$ = Isobutyl |
| A = A-6; $R^{6a}$ = Me; $R^{6b}$ = propyl |
| A = A-6; $R^{6a}$ = ethyl)( ; $R^{6b}$ = ethyl |
| A = A-6; $R^{6a}$ = Me; $R^{6b}$ = 3,3,3-trifluoropropyl |
| A = A-6; $R^{6a}$ = Me; $R^{6b}$ = 2,2,3,3,3-pentafluoropropyl |
| A = A-6; $R^{6a}$ = 3,3,3-trifluoropropyl; $R^{6b}$ = 3,3,3-trifluoropropyl |
| A = A-7; $R^{15}$ = ethyl |
| A = A-7; $R^{15}$ = hexyl |
| A = A-7; $R^{15}$ = isobutyl |
| A = A-7; $R^{15}$ = methyl |

$R^2$ = F, $(R^3)_m$ = 3-F and Z = O

The present disclosure also includes Tables 392 through 585. Each Table is constructed in the same manner as Table 391 above, except that the row heading in Table 391 (i.e. "$R^2$=F, $(R^3)_m$=3-F and Z=O") is replaced with the respective row heading shown below. For example, the header row in Table 392 is "$R^2$=Cl, $(R^3)_m$=3-F and Z=O" and the first entry in Table 392 is a compound of Formula 1 wherein $R^1$=3-bromopropyl, $R^2$=Cl, $(R^3)_m$=3-F and Z=O. Tables 392 through 585 are constructed similarly.

| Header Row | | | |
|---|---|---|---|
| Table | $R^2$ | $(R^3)_m$ | Z |
| 392 | Cl | 3-F | O |
| 393 | Br | 3-F | O |
| 394 | I | 3-F | O |
| 395 | $CF_3$ | 3-F | O |
| 396 | OMe | 3-F | O |
| 397 | Me | 3-F | O |
| 398 | F | 3-Cl | O |
| 399 | Cl | 3-Cl | O |
| 400 | Br | 3-Cl | O |
| 401 | I | 3-Cl | O |
| 402 | $CF_3$ | 3-Cl | O |
| 403 | OMe | 3-Cl | O |
| 404 | Me | 3-Cl | O |
| 405 | F | 3-Br | O |
| 406 | Cl | 3-Br | O |
| 407 | Br | 3-Br | O |
| 408 | I | 3-Br | O |
| 409 | $CF_3$ | 3-Br | O |
| 410 | OMe | 3-Br | O |
| 411 | Me | 3-Br | O |
| 412 | F | 3-I | O |
| 413 | Cl | 3-I | O |
| 414 | Br | 3-I | O |
| 415 | I | 3-I | O |
| 416 | $CF_3$ | 3-I | O |
| 417 | OMe | 3-I | O |
| 418 | Me | 3-I | O |
| 419 | F | 3-CN | O |
| 420 | Cl | 3-CN | O |
| 421 | Br | 3-CN | O |
| 422 | I | 3-CN | O |
| 423 | $CF_3$ | 3-CN | O |
| 424 | OMe | 3-CN | O |
| 425 | Me | 3-CN | O |
| 426 | F | 3-$CF_3$ | O |
| 427 | Cl | 3-$CF_3$ | O |
| 428 | Br | 3-$CF_3$ | O |
| 429 | I | 3-$CF_3$ | O |
| 430 | $CF_3$ | 3-$CF_3$ | O |

-continued

| Table | R² | (R³)ₘ | Z |
|---|---|---|---|
| 431 | OMe | 3-CF₃ | O |
| 432 | Me | 3-CF₃ | O |
| 433 | F | 4-Cl | O |
| 434 | Cl | 4-Cl | O |
| 435 | Br | 4-Cl | O |
| 436 | I | 4-Cl | O |
| 437 | CF₃ | 4-Cl | O |
| 438 | OMe | 4-Cl | O |
| 439 | Me | 4-Cl | O |
| 440 | F | 5-Cl | O |
| 441 | Cl | 5-Cl | O |
| 442 | Br | 5-Cl | O |
| 443 | I | 5-Cl | O |
| 444 | CF₃ | 5-Cl | O |
| 445 | OMe | 5-Cl | O |
| 446 | Me | 5-Cl | O |
| 447 | F | 6-Cl | O |
| 448 | Cl | 6-Cl | O |
| 449 | Br | 6-Cl | O |
| 450 | I | 6-Cl | O |
| 451 | CF₃ | 6-Cl | O |
| 452 | OMe | 6-Cl | O |
| 453 | Me | 6-Cl | O |
| 454 | F | 3-Br, 4-F | O |
| 455 | Cl | 3-Br, 4-F | O |
| 456 | Br | 3-Br, 4-F | O |
| 457 | I | 3-Br, 4-F | O |
| 458 | CF₃ | 3-Br, 4-F | O |
| 459 | OMe | 3-Br, 4-F | O |
| 460 | Me | 3-Br, 4-F | O |
| 461 | F | 3-F, 4-F | O |
| 462 | Cl | 3-F, 4-F | O |
| 463 | Br | 3-F, 4-F | O |
| 464 | I | 3-F, 4-F | O |
| 465 | CF₃ | 3-F, 4-F | O |
| 466 | OMe | 3-F, 4-F | O |
| 467 | Me | 3-F, 4-F | O |
| 468 | F | 3-Cl, 4-F | O |
| 469 | Cl | 3-Cl, 4-F | O |
| 470 | Br | 3-Cl, 4-F | O |
| 471 | I | 3-Cl, 4-F | O |
| 472 | CF₃ | 3-Cl, 4-F | O |
| 473 | OMe | 3-Cl, 4-F | O |
| 474 | Me | 3-Cl, 4-F | O |
| 475 | F | 3-Br | S |
| 476 | Cl | 3-Br | S |
| 477 | Br | 3-Br | S |
| 478 | I | 3-Br | S |
| 479 | CF₃ | 3-Br | S |
| 480 | OMe | 3-Br | S |
| 481 | Me | 3-Br | S |
| 482 | F | 3-Cl | S |
| 483 | Cl | 3-Cl | S |
| 484 | Br | 3-Cl | S |
| 485 | I | 3-Cl | S |
| 486 | CF₃ | 3-Cl | S |
| 487 | OMe | 3-Cl | S |
| 488 | Me | 3-Cl | S |
| 489 | Cl | 3-F | O |
| 490 | Br | 3-F | O |
| 491 | I | 3-F | O |
| 492 | CF₃ | 3-F | O |
| 493 | OMe | 3-F | O |
| 494 | Me | 3-F | O |
| 495 | F | 3-Cl | O |
| 496 | Cl | 3-Cl | O |
| 497 | Br | 3-Cl | O |
| 498 | I | 3-Cl | O |
| 499 | CF₃ | 3-Cl | O |
| 500 | OMe | 3-Cl | O |
| 501 | Me | 3-Cl | O |
| 502 | F | 3-Br | O |
| 503 | Cl | 3-Br | O |
| 504 | Br | 3-Br | O |
| 505 | I | 3-Br | O |
| 506 | CF₃ | 3-Br | O |
| 507 | OMe | 3-Br | O |
| 508 | Me | 3-Br | O |
| 509 | F | 3-I | O |
| 510 | Cl | 3-I | O |
| 511 | Br | 3-I | O |
| 512 | I | 3-I | O |
| 513 | CF₃ | 3-I | O |
| 514 | OMe | 3-I | O |
| 515 | Me | 3-I | O |
| 516 | F | 3-CN | O |
| 517 | Cl | 3-CN | O |
| 518 | Br | 3-CN | O |
| 519 | I | 3-CN | O |
| 520 | CF₃ | 3-CN | O |
| 521 | OMe | 3-CN | O |
| 522 | Me | 3-CN | O |
| 523 | F | 3-CF₃ | O |
| 524 | Cl | 3-CF₃ | O |
| 525 | Br | 3-CF₃ | O |
| 526 | I | 3-CF₃ | O |
| 527 | CF₃ | 3-CF₃ | O |
| 528 | OMe | 3-CF₃ | O |
| 529 | Me | 3-CF₃ | O |
| 530 | F | 4-Cl | O |
| 531 | Cl | 4-Cl | O |
| 532 | Br | 4-Cl | O |
| 533 | I | 4-Cl | O |
| 534 | CF₃ | 4-Cl | O |
| 535 | OMe | 4-Cl | O |
| 536 | Me | 4-Cl | O |
| 537 | F | 5-Cl | O |
| 538 | Cl | 5-Cl | O |
| 539 | Br | 5-Cl | O |
| 540 | I | 5-Cl | O |
| 541 | CF₃ | 5-Cl | O |
| 542 | OMe | 5-Cl | O |
| 543 | Me | 5-Cl | O |
| 544 | F | 6-Cl | O |
| 545 | Cl | 6-Cl | O |
| 546 | Br | 6-Cl | O |
| 547 | I | 6-Cl | O |
| 548 | CF₃ | 6-Cl | O |
| 549 | OMe | 6-Cl | O |
| 550 | Me | 6-Cl | O |
| 551 | F | 3-Br, 4-F | O |
| 552 | Cl | 3-Br, 4-F | O |
| 553 | Br | 3-Br, 4-F | O |
| 554 | I | 3-Br, 4-F | O |
| 555 | CF₃ | 3-Br, 4-F | O |
| 556 | OMe | 3-Br, 4-F | O |
| 557 | Me | 3-Br, 4-F | O |
| 558 | F | 3-F, 4-F | O |
| 559 | Cl | 3-F, 4-F | O |
| 560 | Br | 3-F, 4-F | O |
| 561 | I | 3-F, 4-F | O |
| 562 | CF₃ | 3-F, 4-F | O |
| 563 | OMe | 3-F, 4-F | O |
| 564 | Me | 3-F, 4-F | O |
| 565 | F | 3-Cl, 4-F | O |
| 566 | Cl | 3-Cl, 4-F | O |
| 567 | Br | 3-Cl, 4-F | O |
| 568 | I | 3-Cl, 4-F | O |
| 569 | CF₃ | 3-Cl, 4-F | O |
| 570 | OMe | 3-Cl, 4-F | O |
| 571 | Me | 3-Cl, 4-F | O |
| 572 | F | 3-Br | S |
| 573 | Cl | 3-Br | S |
| 574 | Br | 3-Br | S |
| 575 | I | 3-Br | S |
| 576 | CF₃ | 3-Br | S |
| 577 | OMe | 3-Br | S |
| 578 | Me | 3-Br | S |
| 579 | F | 3-Cl | S |
| 580 | Cl | 3-Cl | S |

| Table | R² | (R³)ₘ | Z |
|---|---|---|---|
| 581 | Br | 3-Cl | S |
| 582 | I | 3-Cl | S |
| 583 | CF₃ | 3-Cl | S |
| 584 | OMe | 3-Cl | S |
| 585 | Me | 3-Cl | S |

The present disclosure also includes Tables 586 through 684. Each Table is constructed in the same manner as Table 1 above, except that the row heading in Table 1 (i.e. "R²=F, (R³)ₘ=3-F, Z=O and A=A-4") is replaced with the respective row heading shown below. For example, the first entry in Table 586 is a compound of Formula 1 wherein R² is Cl, (R³)ₘ is 3-F, Z is O, A is A-3A and R¹ is butyl. Tables 587 through 684 are constructed similarly.

| Table | R² | (R³)ₘ | Z | A |
|---|---|---|---|---|
| 586 | F | 3-F | O | A-4 |
| 587 | F | 3-F | O | A-1 |
| 588 | F | 3-F | O | A-2 |
| 589 | Cl | 3-F | O | A-2 |
| 590 | Br | 3-F | O | A-2 |
| 591 | I | 3-F | O | A-2 |
| 592 | CF₃ | 3-F | O | A-2 |
| 593 | OMe | 3-F | O | A-2 |
| 594 | Me | 3-F | O | A-2 |
| 595 | F | 3-Cl | O | A-2 |
| 596 | Cl | 3-Cl | O | A-2 |
| 597 | Br | 3-Cl | O | A-2 |
| 598 | I | 3-Cl | O | A-2 |
| 599 | CF₃ | 3-Cl | O | A-2 |
| 600 | OMe | 3-Cl | O | A-2 |
| 601 | Me | 3-Cl | O | A-2 |
| 602 | F | 3-Br | O | A-2 |
| 603 | Cl | 3-Br | O | A-2 |
| 604 | Br | 3-Br | O | A-2 |
| 605 | I | 3-Br | O | A-2 |
| 606 | CF₃ | 3-Br | O | A-2 |
| 607 | OMe | 3-Br | O | A-2 |
| 608 | Me | 3-Br | O | A-2 |
| 609 | F | 3-I | O | A-2 |
| 610 | Cl | 3-I | O | A-2 |
| 611 | Br | 3-I | O | A-2 |
| 612 | I | 3-I | O | A-2 |
| 613 | CF₃ | 3-I | O | A-2 |
| 614 | OMe | 3-I | O | A-2 |
| 615 | Me | 3-I | O | A-2 |
| 616 | F | 3-CN | O | A-2 |
| 617 | Cl | 3-CN | O | A-2 |
| 618 | Br | 3-CN | O | A-2 |
| 619 | I | 3-CN | O | A-2 |
| 620 | CF₃ | 3-CN | O | A-2 |
| 621 | OMe | 3-CN | O | A-2 |
| 622 | Me | 3-CN | O | A-2 |
| 623 | F | 3-CF₃ | O | A-2 |
| 624 | Cl | 3-CF₃ | O | A-2 |
| 625 | Br | 3-CF₃ | O | A-2 |
| 626 | I | 3-CF₃ | O | A-2 |
| 627 | CF₃ | 3-CF₃ | O | A-2 |
| 628 | OMe | 3-CF₃ | O | A-2 |
| 629 | Me | 3-CF₃ | O | A-2 |
| 630 | F | 4-Cl | O | A-2 |
| 631 | Cl | 4-Cl | O | A-2 |
| 632 | Br | 4-Cl | O | A-2 |
| 633 | I | 4-Cl | O | A-2 |
| 634 | CF₃ | 4-Cl | O | A-2 |
| 635 | OMe | 4-Cl | O | A-2 |
| 636 | Me | 4-Cl | O | A-2 |
| 637 | F | 5-Cl | O | A-2 |
| 638 | Cl | 5-Cl | O | A-2 |
| 639 | Br | 5-Cl | O | A-2 |
| 640 | I | 5-Cl | O | A-2 |
| 641 | CF₃ | 5-Cl | O | A-2 |
| 642 | OMe | 5-Cl | O | A-2 |
| 643 | Me | 5-Cl | O | A-2 |
| 644 | F | 6-Cl | O | A-2 |
| 645 | Cl | 6-Cl | O | A-2 |
| 646 | Br | 6-Cl | O | A-2 |
| 647 | I | 6-Cl | O | A-2 |
| 648 | CF₃ | 6-Cl | O | A-2 |
| 649 | OMe | 6-Cl | O | A-2 |
| 650 | Me | 6-Cl | O | A-2 |
| 651 | F | 3-Br, 4-F | O | A-2 |
| 652 | Cl | 3-Br, 4-F | O | A-2 |
| 653 | Br | 3-Br, 4-F | O | A-2 |
| 654 | I | 3-Br, 4-F | O | A-2 |
| 655 | CF₃ | 3-Br, 4-F | O | A-2 |
| 656 | OMe | 3-Br, 4-F | O | A-2 |
| 657 | Me | 3-Br, 4-F | O | A-2 |
| 658 | F | 3-F, 4-F | O | A-2 |
| 659 | Cl | 3-F, 4-F | O | A-2 |
| 660 | Br | 3-F, 4-F | O | A-2 |
| 661 | I | 3-F, 4-F | O | A-2 |
| 662 | CF₃ | 3-F, 4-F | O | A-2 |
| 663 | OMe | 3-F, 4-F | O | A-2 |
| 664 | Me | 3-F, 4-F | O | A-2 |
| 665 | F | 3-Cl, 4-F | O | A-2 |
| 666 | Cl | 3-Cl, 4-F | O | A-2 |
| 667 | Br | 3-Cl, 4-F | O | A-2 |
| 668 | I | 3-Cl, 4-F | O | A-2 |
| 669 | CF₃ | 3-Cl, 4-F | O | A-2 |
| 670 | OMe | 3-Cl, 4-F | O | A-2 |
| 671 | Me | 3-Cl, 4-F | O | A-2 |
| 672 | F | 3-Br | S | A-2 |
| 673 | Cl | 3-Br | S | A-2 |
| 674 | Br | 3-Br | S | A-2 |
| 675 | I | 3-Br | S | A-2 |
| 676 | CF₃ | 3-Br | S | A-2 |
| 677 | OMe | 3-Br | S | A-2 |
| 678 | Me | 3-Br | S | A-2 |
| 679 | F | 3-Cl | S | A-2 |
| 680 | Cl | 3-Cl | S | A-2 |
| 681 | Br | 3-Cl | S | A-2 |
| 682 | I | 3-Cl | S | A-2 |
| 683 | CF₃ | 3-Cl | S | A-2 |
| 684 | OMe | 3-Cl | S | A-2 |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates;

phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Compound 1 | 98.5% |
| silica aerogel | 0.5% |
| synthetic amorphous fine silica | 1.0% |

Example B

| Wettable Powder | |
|---|---|
| Compound 1 | 65.0% |
| dodecylphenol polyethylene glycol ether | 2.0% |
| sodium ligninsulfonate | 4.0% |

-continued

Wettable Powder

| | |
|---|---|
| sodium silicoaluminate | 6.0% |
| montmorillonite (calcined) | 23.0% |

Example C

Granule

| | |
|---|---|
| Compound 1 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 1 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Suspension Concentrate

| | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

Emulsion in Water

| | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

Oil Dispersion

| | |
|---|---|
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except "Compound 1" is replaced with "Compound 2", "Compound 3", "Compound 4", "Compound 5", "Compound 6", "Compound 7", "Compound 8", "Compound 9", "Compound 10", "Compound 11", "Compound 12", "Compound 13", "Compound 14", "Compound 15", "Compound 16", "Compound 17", "Compound 18", "Compound 19", "Compound 20", "Compound 21", "Compound 22", "Compound 23", "Compound 24", "Compound 25", "Compound 26", "Compound 27", "Compound 28", "Compound 29", "Compound 30", "Compound 31", "Compound 32", "Compound 33", "Compound 34", "Compound 35", "Compound 36", "Compound 37", "Compound 38", "Compound 39", "Compound 40", "Compound 41", "Compound 42", "Compound 43", "Compound 44", "Compound 45", "Compound 46", "Compound 47", "Compound 48", "Compound 49", "Compound 50", "Compound 51", "Compound 52", "Compound 53", "Compound 54", "Compound 55", "Compound 56", "Compound 57", "Compound 58", "Compound 59", "Compound 60", "Compound 61", "Compound 62", "Compound 63", "Compound 64", "Compound 65", "Compound 66", "Compound 67", "Compound 68", "Compound 69", "Compound 70", "Compound 71", "Compound 72", "Compound 73", "Compound 74", "Compound 75", "Compound 76", "Compound 77", "Compound 78", "Compound 79", "Compound 80", "Compound 81", "Compound 82", "Compound 83", "Compound 84", "Compound 85", "Compound 86", "Compound 87", "Compound 88", "Compound 89", "Compound 90", "Compound 91", "Compound 92", "Compound 93", "Compound 94", "Compound 95", "Compound 96", "Compound 97", "Compound 98", "Compound 99", "Compound 100", "Compound 101", "Compound 102", "Compound 103", "Compound 104", "Compound 104", "Compound 106", "Compound 107", "Compound 108", "Compound 109", "Compound 110", "Compound 111", "Compound 112", "Compound 113", "Compound 114", "Compound 115", "Compound 116", "Compound 117", "Compound 118", "Compound 119", "Compound 120", "Compound 121", "Compound 122", "Compound 123", "Compound 124", "Compound 125", "Compound 126", "Compound 127", "Compound 128", "Compound 129", "Compound 130", "Compound 131", "Compound 132", "Compound 133", "Compound 134", "Compound 135", "Compound 136", "Compound 137", "Compound 138", "Compound 139", "Compound 140", "Compound 141", "Compound 142", "Compound 143", "Compound 144", "Compound 145" or "Compound 146".

Test results indicate that the compounds of the present invention are highly active preemergent and/or postemergent herbicides and/or plant growth regulants. The compounds of the inention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, T1 through T37, are used in Exhibit C for traits. A "-" means the entry is not available; "tol." means "tolerance" and "res." means resistance.

| Trait | Description |
| --- | --- |
| T1 | Glyphosate tol. |
| T2 | High lauric acid oil |
| T3 | Glufosinate tol. |
| T4 | Phytate breakdown |
| T5 | Oxynil tol. |
| T6 | Disease res. |
| T7 | Insect res. |
| T9 | Modified flower color |
| T11 | ALS Herbicide tol. |
| T12 | Dicamba tol. |
| T13 | Anti-allergy |
| T14 | Salt tol. |
| T15 | Cold tol. |
| T16 | Imidazolinone herb. tol. |
| T17 | Modified alpha-amylase |
| T18 | Pollination control |
| T19 | 2,4-D tol. |
| T20 | Increased lysine |
| T21 | Drought tol. |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tol. |

| Trait | Description |
|---|---|
| T31 | Modified oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Modified product |

Exhibit C

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | acl (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T1 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |

| Crop | Event Name | Event Code | Trait(s) | Gene(s) |
|---|---|---|---|---|
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | Fl117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |

| Crop | Event Name | Event Code | Trait(s) | Gene(s) |
|---|---|---|---|---|
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Although most typically, compounds of the invention are used to control undesired vegetation, contact of desired vegetation in the treated locus with compounds of the invention may result in super-additive or synergistic effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

An embodiment of the present invention is a method for controlling the growth of undesired vegetation in genetically modified plants that exhibit traits of glyphosate tolerance, glufosinate tolerance, ALS herbicide tolerance, dicamba tolerance, imidazolinone herbicide tolerance, 2,4-D tolerance, HPPD tolerance and mesotrione tolerance, comprising contacting the vegetation or its environment with a herbicidally effective amount of a compound of Formula 1.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, triallate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3 (2H)-pyridazinone), 5-[[(2,6-difluorophenyl)methoxy]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methyl sulfonyl)-N-(1-methyl-1H-tetrazol-5-yl)-4-(trifluoromethyl)benzamide and 2-methyl-N-(4-methyl-1,2,5-oxadiazol-3-yl)-3-(methyl sulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U. K., 2003 and *The BioPesticide Manual*, 2nd Edition, L. G. Copping, Ed., British Crop Protection Council, Farnham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl) sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of the invention cans also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group 2,4-D, acetochlor, alachlor, atrazine, bromoxynil, bentazon, bicyclopyrone, carfentrazone-ethyl, cloransulam-methyl, dicamba, dimethenamid-p, florasulam, flufenacet, flumioxazin, flupyrsulfuron-methyl, fluroxypyr-meptyl, glyphosate, halauxifen-methyl, isoxaflutole, MCPA, mesotrione, metolachlor, metsulfuron-methyl, nicosulfuron, pyrasulfotole, pyroxasulfone, pyroxsulam, rimsulfuron, saflufenacil, tembotrione, thifensulfuron-methyl, topramazone and tribenuron.

Table A1 lists specific combinations of a Component (a) with Component (b) illustrative of the mixtures, compositions and methods of the present invention. Compound 13 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 13 in Index Table A) with 2,4-D is typically applied in a weight ratio between 1:192-6:1. The remaining lines of Table A1 are to be construed similarly.

TABLE A1

| Component (a) (Compound 13) | Component (b) | Typical Weight Ratio | More Typical Weight Ratio | Most Typical Weight Ratio |
|---|---|---|---|---|
| 13 | 2,4-D | 1:192-6:1 | 1:64-2:1 | 1:24-1:3 |
| 13 | Acetochlor | 1:768-2:1 | 1:256-1:2 | 1:96-1:11 |
| 13 | Acifluorfen | 1:96-12:1 | 1:32-4:1 | 1:12-1:2 |
| 13 | Aclonifen | 1:857-2:1 | 1:285-1:3 | 1:107-1:12 |
| 13 | Alachlor | 1:768-2:1 | 1:256-1:2 | 1:96-1:11 |
| 13 | Ametryn | 1:384-3:1 | 1:128-1:1 | 1:48-1:6 |
| 13 | Amicarbazone | 1:192-6:1 | 1:64-2:1 | 1:24-1:3 |
| 13 | Amidosulfuron | 1:6-168:1 | 1:2-56:1 | 1:1-11:1 |
| 13 | Aminocyclopyrachlor | 1:48-24:1 | 1:16-8:1 | 1:6-2:1 |
| 13 | Aminopyralid | 1:20-56:1 | 1:6-19:1 | 1:2-4:1 |
| 13 | Amitrole | 1:768-2:1 | 1:256-1:2 | 1:96-1:11 |
| 13 | Anilofos | 1:96-12:1 | 1:32-4:1 | 1:12-1:2 |
| 13 | Asulam | 1:960-2:1 | 1:320-1:3 | 1:120-1:14 |
| 13 | Atrazine | 1:192-6:1 | 1:64-2:1 | 1:24-1:3 |
| 13 | Azimsulfuron | 1:6-168:1 | 1:2-56:1 | 1:1-11:1 |
| 13 | Beflubutamid | 1:342-4:1 | 1:114-2:1 | 1:42-1:5 |
| 13 | Benfuresate | 1:617-2:1 | 1:205-1:2 | 1:77-1:9 |
| 13 | Bensulfuron-methyl | 1:25-45:1 | 1:8-15:1 | 1:3-3:1 |
| 13 | Bentazone | 1:192-6:1 | 1:64-2:1 | 1:24-1:3 |
| 13 | Benzobicyclon | 1:85-14:1 | 1:28-5:1 | 1:10-1:2 |
| 13 | Benzofenap | 1:257-5:1 | 1:85-2:1 | 1:32-1:4 |
| 13 | Bicyclopyrone | 1:42-27:1 | 1:14-9:1 | 1:5-2:1 |
| 13 | Bifenox | 1:257-5:1 | 1:85-2:1 | 1:32-1:4 |
| 13 | Bispyribac-sodium | 1:10-112:1 | 1:3-38:1 | 1:1-7:1 |
| 13 | Bromacil | 1:384-3:1 | 1:128-1:1 | 1:48-1:6 |
| 13 | Bromobutide | 1:384-3:1 | 1:128-1:1 | 1:48-1:6 |
| 13 | Bromoxynil | 1:96-12:1 | 1:32-4:1 | 1:12-1:2 |
| 13 | Butachlor | 1:768-2:1 | 1:256-1:2 | 1:96-1:11 |
| 13 | Butafenacil | 1:42-27:1 | 1:14-9:1 | 1:5-2:1 |
| 13 | Butylate | 1:1542-1:2 | 1:514-1:5 | 1:192-1:22 |
| 13 | Carfenstrole | 1:192-6:1 | 1:64-2:1 | 1:24-1:3 |
| 13 | Carfentrazone-ethyl | 1:128-9:1 | 1:42-3:1 | 1:16-1:2 |
| 13 | Chlorimuron-ethyl | 1:8-135:1 | 1:2-45:1 | 1:1-9:1 |
| 13 | Chlorotoluron | 1:768-2:1 | 1:256-1:2 | 1:96-1:11 |
| 13 | Chlorsulfuron | 1:6-168:1 | 1:2-56:1 | 1:1-11:1 |
| 13 | Cincosulfuron | 1:17-68:1 | 1:5-23:1 | 1:2-5:1 |
| 13 | Cinidon-ethyl | 1:384-3:1 | 1:128-1:1 | 1:48-1:6 |
| 13 | Cinmethylin | 1:34-34:1 | 1:11-12:1 | 1:4-3:1 |
| 13 | Clacyfos | 1:34-34:1 | 1:11-12:1 | 1:4-3:1 |
| 13 | Clethodim | 1:48-24:1 | 1:16-8:1 | 1:6-2:1 |
| 13 | Clodinafop-propargyl | 1:20-56:1 | 1:6-19:1 | 1:2-4:1 |
| 13 | Clomazone | 1:384-3:1 | 1:128-1:1 | 1:48-1:6 |
| 13 | Clomeprop | 1:171-7:1 | 1:57-3:1 | 1:21-1:3 |
| 13 | Clopyralid | 1:192-6:1 | 1:64-2:1 | 1:24-1:3 |
| 13 | Cloransulam-methyl | 1:12-96:1 | 1:4-32:1 | 1:1-6:1 |

TABLE A1-continued

| Component (a) (Compound 13) | Component (b) | Typical Weight Ratio | More Typical Weight Ratio | Most Typical Weight Ratio |
|---|---|---|---|---|
| 13 | Cumyluron | 1:384-3:1 | 1:128-1:1 | 1:48-1:6 |
| 13 | Cyanazine | 1:384-3:1 | 1:128-1:1 | 1:48-1:6 |
| 13 | Cyclopyrimorate | 1:17-68:1 | 1:5-23:1 | 1:2-5:1 |
| 13 | Cyclosulfamuron | 1:17-68:1 | 1:5-23:1 | 1:2-5:1 |
| 13 | Cycloxydim | 1:96-12:1 | 1:32-4:1 | 1:12-1:2 |
| 13 | Cyhalofop | 1:25-45:1 | 1:8-15:1 | 1:3-3:1 |
| 13 | Daimuron | 1:192-6:1 | 1:64-2:1 | 1:24-1:3 |
| 13 | Desmedipham | 1:322-4:1 | 1:107-2:1 | 1:40-1:5 |
| 13 | Dicamba | 1:192-6:1 | 1:64-2:1 | 1:24-1:3 |
| 13 | Dichlobenil | 1:1371-1:2 | 1:457-1:4 | 1:171-1:20 |
| 13 | Dichlorprop | 1:925-2:1 | 1:308-1:3 | 1:115-1:13 |
| 13 | Diclofop-methyl | 1:384-3:1 | 1:128-1:1 | 1:48-1:6 |
| 13 | Diclosulam | 1:10-112:1 | 1:3-38:1 | 1:1-7:1 |
| 13 | Difenzoquat | 1:288-4:1 | 1:96-2:1 | 1:36-1:4 |
| 13 | Diflufenican | 1:857-2:1 | 1:285-1:3 | 1:107-1:12 |
| 13 | Diflufenzopyr | 1:12-96:1 | 1:4-32:1 | 1:1-6:1 |
| 13 | Dimethachlor | 1:768-2:1 | 1:256-1:2 | 1:96-1:11 |
| 13 | Dimethametryn | 1:192-6:1 | 1:64-2:1 | 1:24-1:3 |
| 13 | Dimethenamid-P | 1:384-3:1 | 1:128-1:1 | 1:48-1:6 |
| 13 | Dithiopyr | 1:192-6:1 | 1:64-2:1 | 1:24-1:3 |
| 13 | Diuron | 1:384-3:1 | 1:128-1:1 | 1:48-1:6 |
| 13 | EPTC | 1:768-2:1 | 1:256-1:2 | 1:96-1:11 |
| 13 | Esprocarb | 1:1371-1:2 | 1:457-1:4 | 1:171-1:20 |
| 13 | Ethalfluralin | 1:384-3:1 | 1:128-1:1 | 1:48-1:6 |
| 13 | Ethametsulfuron-methyl | 1:17-68:1 | 1:5-23:1 | 1:2-5:1 |
| 13 | Ethoxyfen | 1:8-135:1 | 1:2-45:1 | 1:1-9:1 |
| 13 | Ethoxysulfuron | 1:20-56:1 | 1:6-19:1 | 1:2-4:1 |
| 13 | Etobenzanid | 1:257-5:1 | 1:85-2:1 | 1:32-1:4 |
| 13 | Fenoxaprop-ethyl | 1:120-10:1 | 1:40-4:1 | 1:15-1:2 |
| 13 | Fenoxasulfone | 1:85-14:1 | 1:28-5:1 | 1:10-1:2 |
| 13 | Fenquinotrione | 1:17-68:1 | 1:5-23:1 | 1:2-5:1 |
| 13 | Fentrazamide | 1:17-68:1 | 1:5-23:1 | 1:2-5:1 |
| 13 | Flazasulfuron | 1:17-68:1 | 1:5-23:1 | 1:2-5:1 |
| 13 | Florasulam | 1:2-420:1 | 1:1-140:1 | 2:1-27:1 |
| 13 | Fluazifop-butyl | 1:192-6:1 | 1:64-2:1 | 1:24-1:3 |
| 13 | Flucarbazone | 1:8-135:1 | 1:2-45:1 | 1:1-9:1 |
| 13 | Flucetosulfuron | 1:8-135:1 | 1:2-45:1 | 1:1-9:1 |
| 13 | Flufenacet | 1:257-5:1 | 1:85-2:1 | 1:32-1:4 |
| 13 | Flumetsulam | 1:24-48:1 | 1:8-16:1 | 1:3-3:1 |
| 13 | Flumiclorac-pentyl | 1:10-112:1 | 1:3-38:1 | 1:1-7:1 |
| 13 | Flumioxazin | 1:25-45:1 | 1:8-15:1 | 1:3-3:1 |
| 13 | Fluometuron | 1:384-3:1 | 1:128-1:1 | 1:48-1:6 |
| 13 | Flupyrsulfuron-methyl | 1:3-336:1 | 1:1-112:1 | 2:1-21:1 |
| 13 | Fluridone | 1:384-3:1 | 1:128-1:1 | 1:48-1:6 |
| 13 | Fluroxypyr | 1:96-12:1 | 1:32-4:1 | 1:12-1:2 |
| 13 | Flurtamone | 1:857-2:1 | 1:285-1:3 | 1:107-1:12 |
| 13 | Fluthiacet-methyl | 1:48-42:1 | 1:16-14:1 | 1:3-3:1 |
| 13 | Fomesafen | 1:96-12:1 | 1:32-4:1 | 1:12-1:2 |
| 13 | Foramsulfuron | 1:13-84:1 | 1:4-28:1 | 1:1-6:1 |
| 13 | Glufosinate | 1:288-4:1 | 1:96-2:1 | 1:36-1:4 |
| 13 | Glyphosate | 1:288-4:1 | 1:96-2:1 | 1:36-1:4 |
| 13 | Halosulfuron-methyl | 1:17-68:1 | 1:5-23:1 | 1:2-5:1 |
| 13 | Halauxifen | 1:20-56:1 | 1:6-19:1 | 1:2-4:1 |
| 13 | Halauxifen methyl | 1:20-56:1 | 1:6-19:1 | 1:2-4:1 |
| 13 | Haloxyfop-methyl | 1:34-34:1 | 1:11-12:1 | 1:4-3:1 |
| 13 | Hexazinone | 1:192-6:1 | 1:64-2:1 | 1:24-1:3 |
| 13 | Hydantocidin | 1:1100-16:1 | 1:385-8:1 | 1:144-4:1 |
| 13 | Imazamox | 1:13-84:1 | 1:4-28:1 | 1:1-6:1 |
| 13 | Imazapic | 1:20-56:1 | 1:6-19:1 | 1:2-4:1 |
| 13 | Imazapyr | 1:85-14:1 | 1:28-5:1 | 1:10-1:2 |
| 13 | Imazaquin | 1:34-34:1 | 1:11-12:1 | 1:4-3:1 |
| 13 | Imazethabenz-methyl | 1:171-7:1 | 1:57-3:1 | 1:21-1:3 |
| 13 | Imazethapyr | 1:24-48:1 | 1:8-16:1 | 1:3-3:1 |
| 13 | Imazosulfuron | 1:27-42:1 | 1:9-14:1 | 1:3-3:1 |
| 13 | Indanofan | 1:342-4:1 | 1:114-2:1 | 1:42-1:5 |
| 13 | Indaziflam | 1:25-45:1 | 1:8-15:1 | 1:3-3:1 |
| 13 | Iodosulfuron-methyl | 1:3-336:1 | 1:1-112:1 | 2:1-21:1 |
| 13 | Ioxynil | 1:192-6:1 | 1:64-2:1 | 1:24-1:3 |
| 13 | Ipfencarbazone | 1:85-14:1 | 1:28-5:1 | 1:10-1:2 |
| 13 | Isoproturon | 1:384-3:1 | 1:128-1:1 | 1:48-1:6 |
| 13 | Isoxaben | 1:288-4:1 | 1:96-2:1 | 1:36-1:4 |
| 13 | Isoxaflutole | 1:60-20:1 | 1:20-7:1 | 1:7-2:1 |
| 13 | Lactofen | 1:42-27:1 | 1:14-9:1 | 1:5-2:1 |
| 13 | Lenacil | 1:384-3:1 | 1:128-1:1 | 1:48-1:6 |
| 13 | Linuron | 1:384-3:1 | 1:128-1:1 | 1:48-1:6 |
| 13 | MCPA | 1:192-6:1 | 1:64-2:1 | 1:24-1:3 |
| 13 | MCPB | 1:288-4:1 | 1:96-2:1 | 1:36-1:4 |

TABLE A1-continued

| Component (a) (Compound 13) | Component (b) | Typical Weight Ratio | More Typical Weight Ratio | Most Typical Weight Ratio |
|---|---|---|---|---|
| 13 | Mecoprop | 1:768-2:1 | 1:256-1:2 | 1:96-1:11 |
| 13 | Mefenacet | 1:384-3:1 | 1:128-1:1 | 1:48-1:6 |
| 13 | Mefluidide | 1:192-6:1 | 1:64-2:1 | 1:24-1:3 |
| 13 | Mesosulfuron-methyl | 1:5-224:1 | 1:1-75:1 | 1:1-14:1 |
| 13 | Mesotrione | 1:42-27:1 | 1:14-9:1 | 1:5-2:1 |
| 13 | Metamifop | 1:42-27:1 | 1:14-9:1 | 1:5-2:1 |
| 13 | Metazachlor | 1:384-3:1 | 1:128-1:1 | 1:48-1:6 |
| 13 | Metazosulfuron | 1:25-45:1 | 1:8-15:1 | 1:3-3:1 |
| 13 | Methabenzthiazuron | 1:768-2:1 | 1:256-1:2 | 1:96-1:11 |
| 13 | Metolachlor | 1:768-2:1 | 1:256-1:2 | 1:96-1:11 |
| 13 | Metosulam | 1:8-135:1 | 1:2-45:1 | 1:1-9:1 |
| 13 | Metribuzin | 1:192-6:1 | 1:64-2:1 | 1:24-1:3 |
| 13 | Metsulfuron-methyl | 1:2-560:1 | 1:1-187:1 | 3:1-35:1 |
| 13 | Molinate | 1:1028-2:1 | 1:342-1:3 | 1:128-1:15 |
| 13 | Napropamide | 1:384-3:1 | 1:128-1:1 | 1:48-1:6 |
| 13 | Napropamide-M | 1:192-6:1 | 1:64-2:1 | 1:24-1:3 |
| 13 | Naptalam | 1:192-6:1 | 1:64-2:1 | 1:24-1:3 |
| 13 | Nicosulfuron | 1:12-96:1 | 1:4-32:1 | 1:1-6:1 |
| 13 | Norflurazon | 1:1152-1:1 | 1:384-1:3 | 1:144-1:16 |
| 13 | Orbencarb | 1:1371-1:2 | 1:457-1:4 | 1:171-1:20 |
| 13 | Orthosulfamuron | 1:20-56:1 | 1:6-19:1 | 1:2-4:1 |
| 13 | Oryzalin | 1:514-3:1 | 1:171-1:2 | 1:64-1:8 |
| 13 | Oxadiargyl | 1:384-3:1 | 1:128-1:1 | 1:48-1:6 |
| 13 | Oxadiazon | 1:548-3:1 | 1:182-1:2 | 1:68-1:8 |
| 13 | Oxasulfuron | 1:27-42:1 | 1:9-14:1 | 1:3-3:1 |
| 13 | Oxaziclomefone | 1:42-27:1 | 1:14-9:1 | 1:5-2:1 |
| 13 | Oxyfluorfen | 1:384-3:1 | 1:128-1:1 | 1:48-1:6 |
| 13 | Paraquat | 1:192-6:1 | 1:64-2:1 | 1:24-1:3 |
| 13 | Pendimethalin | 1:384-3:1 | 1:128-1:1 | 1:48-1:6 |
| 13 | Penoxsulam | 1:10-112:1 | 1:3-38:1 | 1:1-7:1 |
| 13 | Penthoxamid | 1:384-3:1 | 1:128-1:1 | 1:48-1:6 |
| 13 | Pentoxazone | 1:102-12:1 | 1:34-4:1 | 1:12-1:2 |
| 13 | Phenmedipham | 1:102-12:1 | 1:34-4:1 | 1:12-1:2 |
| 13 | Picloram | 1:96-12:1 | 1:32-4:1 | 1:12-1:2 |
| 13 | Picolinafen | 1:34-34:1 | 1:11-12:1 | 1:4-3:1 |
| 13 | Pinoxaden | 1:25-45:1 | 1:8-15:1 | 1:3-3:1 |
| 13 | Pretilachlor | 1:192-6:1 | 1:64-2:1 | 1:24-1:3 |
| 13 | Primisulfuron-methyl | 1:8-135:1 | 1:2-45:1 | 1:1-9:1 |
| 13 | Prodiamine | 1:384-3:1 | 1:128-1:1 | 1:48-1:6 |
| 13 | Profoxydim | 1:42-27:1 | 1:14-9:1 | 1:5-2:1 |
| 13 | Prometryn | 1:384-3:1 | 1:128-1:1 | 1:48-1:6 |
| 13 | Propachlor | 1:1152-1:1 | 1:384-1:3 | 1:144-1:16 |
| 13 | Propanil | 1:384-3:1 | 1:128-1:1 | 1:48-1:6 |
| 13 | Propaquizafop | 1:48-24:1 | 1:16-8:1 | 1:6-2:1 |
| 13 | Propoxycarbazone | 1:17-68:1 | 1:5-23:1 | 1:2-5:1 |
| 13 | Propyrisulfuron | 1:17-68:1 | 1:5-23:1 | 1:2-5:1 |
| 13 | Propyzamide | 1:384-3:1 | 1:128-1:1 | 1:48-1:6 |
| 13 | Prosulfocarb | 1:1200-1:2 | 1:400-1:4 | 1:150-1:17 |
| 13 | Prosulfuron | 1:6-168:1 | 1:2-56:1 | 1:1-11:1 |
| 13 | Pyraclonil | 1:42-27:1 | 1:14-9:1 | 1:5-2:1 |
| 13 | Pyraflufen-ethyl | 1:5-224:1 | 1:1-75:1 | 1:1-14:1 |
| 13 | Pyrasulfotole | 1:13-84:1 | 1:4-28:1 | 1:1-6:1 |
| 13 | Pyrazolynate | 1:857-2:1 | 1:285-1:3 | 1:107-1:12 |
| 13 | Pyrazosulfuron-ethyl | 1:10-112:1 | 1:3-38:1 | 1:1-7:1 |
| 13 | Pyrazoxyfen | 1:5-224:1 | 1:1-75:1 | 1:1-14:1 |
| 13 | Pyribenzoxim | 1:10-112:1 | 1:3-38:1 | 1:1-7:1 |
| 13 | Pyributicarb | 1:384-3:1 | 1:128-1:1 | 1:48-1:6 |
| 13 | Pyridate | 1:288-4:1 | 1:96-2:1 | 1:36-1:4 |
| 13 | Pyriftalid | 1:10-112:1 | 1:3-38:1 | 1:1-7:1 |
| 13 | Pyriminobac-methyl | 1:20-56:1 | 1:6-19:1 | 1:2-4:1 |
| 13 | Pyrimisulfan | 1:17-68:1 | 1:5-23:1 | 1:2-5:1 |
| 13 | Pyrithiobac | 1:24-48:1 | 1:8-16:1 | 1:3-3:1 |
| 13 | Pyroxasulfone | 1:85-14:1 | 1:28-5:1 | 1:10-1:2 |
| 13 | Pyroxsulam | 1:5-224:1 | 1:1-75:1 | 1:1-14:1 |
| 13 | Quinclorac | 1:192-6:1 | 1:64-2:1 | 1:24-1:3 |
| 13 | Quizalofop-ethyl | 1:42-27:1 | 1:14-9:1 | 1:5-2:1 |
| 13 | Rimsulfuron | 1:13-84:1 | 1:4-28:1 | 1:1-6:1 |
| 13 | Saflufenacil | 1:25-45:1 | 1:8-15:1 | 1:3-3:1 |
| 13 | Sethoxydim | 1:96-12:1 | 1:32-4:1 | 1:12-1:2 |
| 13 | Simazine | 1:384-3:1 | 1:128-1:1 | 1:48-1:6 |
| 13 | Sulcotrione | 1:120-10:1 | 1:40-4:1 | 1:15-1:2 |
| 13 | Sulfentrazone | 1:147-8:1 | 1:49-3:1 | 1:18-1:3 |
| 13 | Sulfometuron-methyl | 1:34-34:1 | 1:11-12:1 | 1:4-3:1 |
| 13 | Sulfosulfuron | 1:8-135:1 | 1:2-45:1 | 1:1-9:1 |
| 13 | Tebuthiuron | 1:384-3:1 | 1:128-1:1 | 1:48-1:6 |
| 13 | Tefuryltrione | 1:42-27:1 | 1:14-9:1 | 1:5-2:1 |
| 13 | Tembotrione | 1:31-37:1 | 1:10-13:1 | 1:3-3:1 |

TABLE A1-continued

| Component (a) (Compound 13) | Component (b) | Typical Weight Ratio | More Typical Weight Ratio | Most Typical Weight Ratio |
|---|---|---|---|---|
| 13 | Tepraloxydim | 1:25-45:1 | 1:8-15:1 | 1:3-3:1 |
| 13 | Terbacil | 1:288-4:1 | 1:96-2:1 | 1:36-1:4 |
| 13 | Terbuthylazine | 1:857-2:1 | 1:285-1:3 | 1:107-1:12 |
| 13 | Terbutryn | 1:192-6:1 | 1:64-2:1 | 1:24-1:3 |
| 13 | Thenylchlor | 1:85-14:1 | 1:28-5:1 | 1:10-1:2 |
| 13 | Thiazopyr | 1:384-3:1 | 1:128-1:1 | 1:48-1:6 |
| 13 | Thiencarbazone | 1:3-336:1 | 1:1-112:1 | 2:1-21:1 |
| 13 | Thifensulfuron-methyl | 1:5-224:1 | 1:1-75:1 | 1:1-14:1 |
| 13 | Tiafenacil | 1:17-68:1 | 1:5-23:1 | 1:2-5:1 |
| 13 | Thiobencarb | 1:768-2:1 | 1:256-1:2 | 1:96-1:11 |
| 13 | Tolpyralate | 1:31-37:1 | 1:10-13:1 | 1:3-3:1 |
| 13 | Topramzone | 1:6-168:1 | 1:2-56:1 | 1:1-11:1 |
| 13 | Tralkoxydim | 1:68-17:1 | 1:22-6:1 | 1:8-2:1 |
| 13 | Triafamone | 1:2-420:1 | 1:1-140:1 | 2:1-27:1 |
| 13 | Triallate | 1:768-2:1 | 1:256-1:2 | 1:96-1:11 |
| 13 | Triasulfuron | 1:5-224:1 | 1:1-75:1 | 1:1-14:1 |
| 13 | Triaziflam | 1:171-7:1 | 1:57-3:1 | 1:21-1:3 |
| 13 | Tribenuron-methyl | 1:3-336:1 | 1:1-112:1 | 2:1-21:1 |
| 13 | Triclopyr | 1:192-6:1 | 1:64-2:1 | 1:24-1:3 |
| 13 | Trifloxysulfuron | 1:2-420:1 | 1:1-140:1 | 2:1-27:1 |
| 13 | Trifludimoxazin | 1:25-45:1 | 1:8-15:1 | 1:3-3:1 |
| 13 | Trifluralin | 1:288-4:1 | 1:96-2:1 | 1:36-1:4 |
| 13 | Triflusulfuron-methyl | 1:17-68:1 | 1:5-23:1 | 1:2-5:1 |
| 13 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 15 in the Component (a) column is identified in Index Table A. Thus, for example, in Table A2 the entries below the "Component (a)" column heading all recite "Compound 15" (i.e. Compound 15 identified in Index Table A), and the first line below the column headings in Table A2 specifically discloses a mixture of Compound 15 with 2,4-D. Tables A3 through A146 are constructed similarly.

| Table Number | Component (a) Column Entries |
|---|---|
| A2 | Compound 15 |
| A3 | Compound 16 |
| A4 | Compound 21 |
| A5 | Compound 22 |
| A6 | Compound 23 |
| A7 | Compound 24 |
| A8 | Compound 27 |
| A9 | Compound 1 |
| A10 | Compound 2 |
| A11 | Compound 3 |
| A12 | Compound 4 |
| A13 | Compound 5 |
| A14 | Compound 6 |
| A15 | Compound 7 |
| A16 | Compound 8 |
| A17 | Compound 9 |
| A18 | Compound 10 |
| A19 | Compound 11 |
| A20 | Compound 12 |
| A21 | Compound 14 |
| A22 | Compound 17 |
| A23 | Compound 18 |
| A24 | Compound 19 |
| A25 | Compound 20 |
| A26 | Compound 25 |
| A27 | Compound 26 |
| A28 | Compound 28 |
| A29 | Compound 29 |
| A30 | Compound 30 |
| A31 | Compound 31 |
| A32 | Compound 32 |
| A33 | Compound 33 |
| A34 | Compound 34 |
| A35 | Compound 35 |
| A36 | Compound 36 |
| A37 | Compound 37 |
| A38 | Compound 38 |
| A39 | Compound 39 |
| A40 | Compound 40 |
| A41 | Compound 41 |
| A42 | Compound 42 |
| A43 | Compound 43 |
| A44 | Compound 44 |
| A45 | Compound 45 |
| A46 | Compound 46 |
| A47 | Compound 47 |
| A48 | Compound 48 |
| A49 | Compound 49 |
| A50 | Compound 50 |
| A51 | Compound 51 |
| A52 | Compound 52 |
| A53 | Compound 53 |
| A54 | Compound 54 |
| A55 | Compound 55 |
| A56 | Compound 56 |
| A57 | Compound 57 |
| A58 | Compound 58 |
| A59 | Compound 59 |
| A60 | Compound 60 |
| A61 | Compound 61 |

| Table Number | Component (a) Column Entries |
|---|---|
| A62 | Compound 62 |
| A63 | Compound 63 |
| A64 | Compound 64 |
| A65 | Compound 65 |
| A66 | Compound 66 |
| A67 | Compound 67 |
| A68 | Compound 68 |
| A69 | Compound 69 |
| A70 | Compound 70 |
| A71 | Compound 71 |
| A72 | Compound 72 |
| A73 | Compound 73 |
| A74 | Compound 74 |
| A75 | Compound 75 |
| A76 | Compound 76 |
| A77 | Compound 77 |
| A78 | Compound 78 |
| A79 | Compound 79 |
| A80 | Compound 80 |
| A81 | Compound 81 |
| A82 | Compound 82 |
| A83 | Compound 83 |
| A84 | Compound 84 |
| A85 | Compound 85 |
| A86 | Compound 86 |
| A87 | Compound 87 |
| A88 | Compound 88 |
| A89 | Compound 89 |
| A90 | Compound 90 |
| A91 | Compound 91 |
| A92 | Compound 92 |
| A93 | Compound 93 |
| A94 | Compound 94 |
| A95 | Compound 95 |
| A96 | Compound 96 |
| A97 | Compound 97 |
| A98 | Compound 98 |
| A99 | Compound 99 |
| A100 | Compound 100 |
| A101 | Compound 101 |
| A102 | Compound 102 |
| A103 | Compound 103 |
| A104 | Compound 104 |
| A105 | Compound 104 |
| A106 | Compound 106 |
| A107 | Compound 107 |
| A108 | Compound 108 |
| A109 | Compound 109 |
| A110 | Compound 110 |
| A111 | Compound 111 |
| A112 | Compound 112 |
| A113 | Compound 113 |
| A114 | Compound 114 |
| A115 | Compound 115 |
| A116 | Compound 116 |
| A117 | Compound 117 |
| A118 | Compound 118 |
| A119 | Compound 119 |
| A120 | Compound 120 |
| A121 | Compound 121 |
| A122 | Compound 122 |
| A123 | Compound 123 |
| A124 | Compound 124 |
| A125 | Compound 125 |
| A126 | Compound 126 |
| A127 | Compound 127 |
| A128 | Compound 128 |
| A129 | Compound 129 |
| A130 | Compound 130 |
| A131 | Compound 131 |
| A132 | Compound 132 |
| A133 | Compound 133 |
| A134 | Compound 134 |
| A135 | Compound 135 |
| A136 | Compound 136 |
| A137 | Compound 137 |
| A138 | Compound 138 |
| A139 | Compound 139 |
| A140 | Compound 140 |
| A141 | Compound 141 |
| A142 | Compound 142 |
| A143 | Compound 143 |
| A144 | Compound 144 |
| A145 | Compound 145 |
| A146 | Compound 146 |

The compounds of the present invention are useful for the control of weed species that are resistant to herbicides with the AHAS-inhibitor or (b2) [chemical compound that inhibits acetohydroxy acid synthase (AHAS), also known as acetolactate synthase (ALS)] mode of action.

The following Tests demonstrate the control efficacy of the compounds of this invention against specific weeds. The weed control afforded by the compounds is not limited, however, to these species. See Index Tables A-C for compound descriptions. The following abbreviations are used in the Index Tables which follow: t is tertiary, s is secondary, n is normal, i is iso, c is cyclo, Me is methyl, Et is ethyl, Pr is propyl, i-Pr is isopropyl, Bu is butyl, c-Pr is cyclopropyl, t-Bu is tert-butyl, Ph is phenyl, OMe is methoxy, OEt is ethoxy, SMe is methylthio, TFP is trifluoropropyl (i.e. —$CH_2CH_2CF_3$), Bn is benzyl and —CN is cyano. The abbreviation "Cmpd. No." stands for "Compound Number". The abbreviation "Ex." stands for "Example" and is followed by a number indicating in which example the compound is prepared. Mass spectra are reported with an estimated precision within +0.5 Da as the molecular weight of the highest isotopic abundance parent ion (M+1) formed by addition of $H^+$ (molecular weight of 1) to the molecule. The presence of molecular ions containing one or more higher atomic weight isotopes of lower abundance (e.g., $^{37}Cl$, $^{81}Br$) is not reported. The alternate molecular ion peaks (e.g., M+2 or M+4) that occur with compounds containing multiple halogens are not reported. The reported M+1 peaks were observed by mass spectrometry using atmospheric pressure chemical ionization ($AP^+$) or electrospray ionization (ESI).

INDEX TABLE A

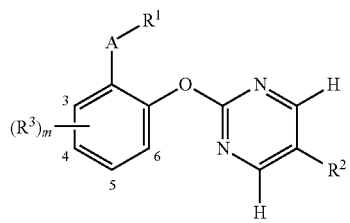

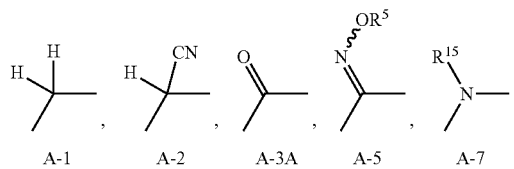

| Cmpd. No. | A | R¹ | R² | R³ | M.S.(AP+) or m.p. |
|---|---|---|---|---|---|
| 1 | A-3A | OCH$_2$CH(CH$_3$)$_2$ | Cl | 3-Br | * |
| 2 | A-3A | OCH$_2$C(Cl)=CH$_2$ | Cl | 3-Br | * |
| 3 | A-3A | OCH$_2$C(CH$_3$)=CH$_2$ | Cl | 3-Br | * |
| 4 | A-3A | OCH$_2$CF$_2$CF$_3$ | Br | 3-F | 447 |
| 5 | A-3A | OCH$_2$CF$_2$CF$_3$ | Cl | 3-F | 401 |
| 6 | A-3A | OCH$_2$(cyclo-pentyl) | Cl | 3-Br | 411 |
| 7 | A-3A | OCH$_2$CH$_2$CN | Cl | 3-Br | 382 |
| 8 | A-3A | OCH$_2$(cyclo-butyl) | Cl | 3-Br | 397 |
| 9 | A-3A | OCH$_2$(cyclo-propyl) | Cl | 3-Br | 393 |
| 10 | A-3A | OCH$_2$(2,2-di-F-cyclo-propyl) | Cl | 3-Br | 419 |
| 11 | A-3A | OCH$_2$CH=C(CH$_3$)$_2$ | Cl | 3-Br | 397 |
| 12 | A-3A | CH$_3$ | Cl | 3-Br | * |
| 13 | A-3A | OCH$_2$CH$_2$CH$_3$ | Cl | 3-Br | * |
| 14 | A-3A | OC(CH$_3$)$_3$ | Cl | 3-Br | * |
| 15 | A-3A | OCH$_2$CH$_2$CF$_3$ | Cl | 3-Cl | 381 |
| 16 | A-3A | OCH(CH$_3$)CH$_2$CF$_3$ | Cl | 3-Br | 439 |
| 17 | A-3A | OCH$_2$CH$_2$CF$_3$ | Cl | (m = 0) | 347 |
| 18 | A-3A | N(CH$_3$)CH$_2$CH(CH$_3$)(CF$_3$) | Cl | 3-Br | 452 |
| 19 | A-3A | N(CH$_3$)CH$_2$CH$_2$CF$_3$ | Cl | 3-Br | 438 |
| 20 | A-3A | OCH$_2$CH$_2$CH$_2$CF$_3$ | Cl | 3-Br | * |
| 21 (Ex. 2) | A-3A | OCH$_2$CH$_2$CH=CH$_2$ | Cl | 3-Br | * |
| 22 | A-3A | OCH$_2$CH=CH$_2$ | Cl | 3-Br | 369 |
| 23 | A-3A | OCH$_2$CF$_2$CF$_3$ | Cl | 3-Br | 461 |
| 24 | A-3A | N(CH$_3$)OCH$_2$CF$_3$ | Br | 3-Br | 484 |
| 25 | A-3A | N(CH$_3$)OCH$_2$CF$_3$ | Cl | 3-Br | 440 |
| 26 (Ex. 3) | A-3A | OCH$_2$CH$_2$CF$_3$ | Cl | 3-Br | 425 |
| 27 | A-3A | NHCH$_2$CF$_3$ | Br | (m = 0) | * |
| 28 (Ex. 1) | A-3A | NHCH$_2$CF$_3$ | Cl | (m = 0) | * |
| 29 | A-3A | CH$_2$Cl | Cl | (m = 0) | 283 (65-70) |
| 30 | A-3A | OCH$_2$CH$_2$CF$_3$ | Cl | 3-CN | 372 |
| 31 | A-3A | OCH$_2$CF$_3$ | CN | 3-Br | * |
| 32 | A-3A | OCH$_2$CF$_3$ | Cl | 3-CN | 358 |
| 33 | A-3A | OCH$_2$CH$_2$CF$_3$ | Br | 3-Br | 467 |
| 34 | A-3A | OCH$_2$CF$_3$ | Br | 3-Br | 455 |
| 35 | A-3A | OCH$_2$CF$_3$ | Cl | 3-Br | 411 |
| 36 | A-3A | OCH(CH$_2$Cl)$_2$ | Cl | 3-Br | 439 |
| 37 | A-3A | OCH$_2$CH(CH$_3$)CH=CH$_2$ | Cl | 3-Br | 397 |
| 38 | A-3A | OCH$_2$CH$_2$C≡CH | Cl | 3-Br | 381 |
| 39 | A-3A | OCH$_2$CN | Cl | 3-CN | 315 |
| 40 | A-3A | OCH$_2$CN | Cl | 3-Br | * |
| 41 | A-3A | OCH$_2$CH$_2$CF$_3$ | Br | 3-F | 409 |
| 42 | A-3A | OCH$_2$CH$_2$CF$_3$ | Cl | 3-F | 365 |
| 43 | A-3A | OC(CH$_3$)$_3$ | Cl | 3-F | 325 |
| 44 | A-3A | O(cyclo-pentyl) | Cl | 3-Br | 397 |
| 45 | A-3A | OCH$_2$CCl$_3$ | Cl | 3-Br | 459 |
| 46 | A-3A | OCH$_2$CH$_2$Cl | Cl | 3-Br | 391 |
| 47 | A-3A | OCH$_2$CF$_3$ | Br | 3-F | 396 |
| 48 | A-3A | OCH$_2$CF$_3$ | Cl | 3-F | 351 |
| 49 | A-3A | OCH$_2$CN | Cl | 3-F | 308 (80-83) |
| 50 | A-3A | E-OCH$_2$CH=CHCF$_3$ | Cl | 3-Br | 437 |
| 51 | A-3A | CH$_3$ | Cl | 3-OMe | 279 |
| 52 | A-3A | CH$_3$ | Cl | (m = 0) | 249 |
| 55 | A-5; R⁵ is Me | CH$_3$ | Cl | (m = 0) | 278 |
| 56 | A-5; R⁵ is i-Pr | CH$_3$ | Cl | (m = 0) | 306 |
| 57 | A-5; R⁵ is i-Pr | H | Cl | (m = 0) | 292 |
| 58 | A-5; R⁵ is Bn | CH$_3$ | Cl | (m = 0) | 354 |
| 59 | A-5; R⁵ is t-Bu | CH$_3$ | Cl | (m = 0) | 320 |

INDEX TABLE A-continued

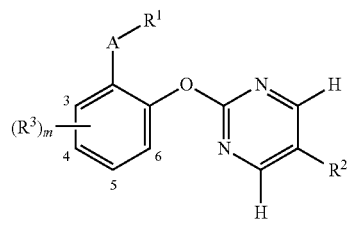

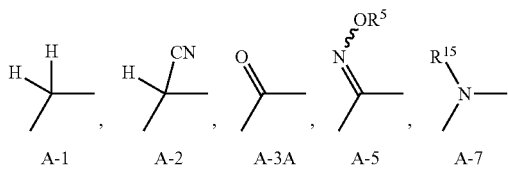

| Cmpd. No. | A | R¹ | R² | R³ | M.S.(AP+) or m.p. |
|---|---|---|---|---|---|
| 60 | A-5; R⁵ is H | CH₃ | Cl | (m = 0) | 264 |
| 61 | A-3A | OCH₂C(Br)=CH₂ | Cl | 3-Br | 87-91 |
| 62 | A-1 | OCH₂CF₃ | Cl | 3-Br | 63-66 |
| 63 | A-1 | OCH₂CF₂CF₃ | Cl | 3-Br | 49-53 |
| 64 | A-3A | OCH₂CH₂CF₃ | Cl | 4-CN | 117-120 |
| 65 | A-3A | OCH₂CH₂CH₂CF₃ | Cl | 3-CF₃ | 429 |
| 66 | A-1 | OCH₂CH₂CF₃ | Cl | 3-Br | 63-67 |
| 67 | A-3A | CH₂CH₂CH₃ | Cl | 3-CN | 85-88 |
| 68 | A-3A | CH₂CH₂CH₂CH₃ | Cl | 3-CN | 98-102 |
| 69 | A-5; R⁵ is i-Pr | CH₃ | Cl | 3-CN | 80-84 |
| 70 | A-3A | SCH₂CH₂CH₃ | Cl | 3-Br | 387 |
| 71 | A-3A | SCH₂CH₂CF₃ | Cl | 3-Br | 121-125 |
| 72 | A-1 | CH₂CH₂CF₃ | Cl | 3-CN | 342 |
| 73 | A-1 | (CH₂)₃CF₃ | Cl | 3-CN | 356 |
| 74 | A-1 | O(CH₂)₃CF₃ | Cl | 3-Br | 425 |
| 75 | A-3A | CH₂CH₂CH₃ | Cl | 3-Br | 88-92 |
| 76 | A-5; R⁵ is i-Pr | CH₃ | Cl | 3-F | 62-66 |
| 77 | A-3A | (CH₂)₃CF₃ | Cl | 3-Br | 423 |
| 78 | A-3A | O(c-Bu) | Cl | 3-Br | 100-103 |
| 79 | A-3A | (CH₂)₃CH₃ | Cl | 3-Br | 77-81 |
| 80 | A-1 | O(CH₂)₂CF₃ | Cl | 3-CN | 358 |
| 81 | A-1 | O(CH₂)₃CF₃ | Cl | 3-CN | 372 |
| 82 | A-3A | (CH₂)₄CF₃ | Cl | 3-Br | 437 |
| 83 | A-3A | SCH₂CH₃ | Cl | 3-Br | 373 |
| 84 | A-3A | OCH(CH₃)CH₂CH₃ | Cl | 3-Br | 385 |
| 85 | A-3A | SCH₂CF₃ | Cl | 3-Br | 90-93 |
| 86 | A-1 | (CH₂)₂CH₃ | Cl | 3-CN | 288 |
| 87 | A-1 | (CH₂)₃CH₃ | Cl | 3-CN | 302 |
| 88 | A-3A | O(CH₂)₂CF₃ | Cl | 4-Cl | 87-90 |
| 89 | A-1 | (CH₂)₂CF₃ | Cl | 3-Br | 395 |
| 90 | A-3A | OCH₂CH₂C(=CH₂)CH₃ | Cl | 3-Br | 397 |
| 91 | A-3A | SCH₂CH=CH₂ | Cl | 3-Br | 385 |
| 92 | A-3A | (CH₂)₂CF₃ | Cl | 3-Br | 409 |
| 93 | A-3A | NH(CH₂)₂CF₃ | Cl | 3-Br | 424 |
| 94 | A-3A | O(CH₂)₂CF₃ | Cl | 4-Br | 88-91 |
| 95 | A-5; R⁵ is Et | CH₃ | Cl | 3-Br | 370 |
| 96 | A-3A | O(CH₂)₂C(CH₃)₃ | Cl | 3-Br | 413 |
| 97 | A-3A | OCH₂CHClCH₂Cl | Cl | 3-Br | 439 |
| 98 | A-5; R⁵ is TFP | CH₃ | Cl | 3-Br | * |
| 99 | A-3A | O(CH₂)₂CF₃ | Cl | 3-CH₃ | 51-53 |
| 100 | A-3A | O(CH₂)₃CH₃ | Cl | 3-Br | 385 |
| 101 | A-3A | O(CH₂)₄CH₃ | Cl | 3-Br | 399 |
| 102 | A-3A | OCH₂CH₂CH₂Br | Cl | 3-Br | 449 |
| 103 | A-3A | OCH₂CF₂CHF₂ | Cl | 3-Br | 443 |
| 104 | A-5; R⁵ is i-Pr | CH₃ | Cl | 3-Cl | 340 |
| 105 | A-5; R⁵ is i-Pr | CH₃ | Cl | 3-Br | 384 |
| 106 | A-1 | OCH₂CH₃ | Cl | 3-Br | 343 |
| 107 (Ex. 4) | A-3A | (CH₂)₂CF₃ | Cl | 3-Cl | ** |
| 108 | A-3A | OCH₂C≡CH | Cl | 3-Br | 108-112 |
| 109 | A-3A | (CH₂)₄CF₃ | Cl | 3-CN | 384 |
| 110 | A-3A | CH₂CH₂CF₂CF₃ | Cl | 3-Br | 459 |
| 111 | A-3A | CH₂CH₂CF₂CF₃ | Cl | 3-CN | 406 |
| 112 | A-3A | O(CH₂)₂CF₃ | Cl | 3-OCH₃ | 109-113 |
| 113 | A-3A | O(CH₂)₂CF₃ | Cl | 3-CF₃ | 415 |
| 114 | A-2 | (CH₂)₃CH₃ | Cl | 3-Br | 380 |
| 115 | A-3A | O(CH₂)₂CF₃ | Cl | 3-O-i-Pr | 405 |
| 116 | A-3A | O(CH₂)₂CF₃ | Cl | 3-OCH₂CH₃ | 391 |

INDEX TABLE A-continued

| Cmpd. No. | A | R¹ | R² | R³ | M.S.(AP+) or m.p. |
|---|---|---|---|---|---|
| 117 | A-3A | O(CH₂)₂CF₃ | Cl | 3-OCH₂CF₃ | 445 |
| 118 | A-2 | (CH₂)₂CH₃ | Cl | 3-Br | 366 |
| 119 | A-3A | cis-OCH₂CCl=CCl | Cl | 3-Br | 114-117 |
| 120 | A-3A | trans-OCH₂CCl=CCl | Cl | 3-Br | 84-88 |
| 121 | A-1 | (CH₂)₄CF₃ | Cl | 3-Br | 423 |
| 122 | A-1 | (CH₂)₂CF₃ | Cl | 3-Cl | 351 |
| 123 | A-3A | O(CH₂)₂c-Pr | Cl | 3-Br | 397 |
| 124 | A-1 | (CH₂)₄CF₃ | Cl | 3-Cl | 379 |
| 125 | A-3A | (CH₂)₃CF₃ | Cl | 3-CF₃ | 413 |
| 126 | A-7; R¹⁵ is Me | (CH₂)₃CF₃ | Cl | 3-CN | 371 |
| 127 | A-3A | cis-OCH₂C=C(CH₃)Cl | Cl | 3-Br | 59-63 |
| 128 | A-3A | trans-OCH₂C=C(CH₃)Cl | Cl | 3-Br | 82-86 |
| 129 | A-2 | (CH₂)₃CH₃ | Cl | (m = 0) | 302 |
| 130 | A-3A | (CH₂)₃CH₃ | Cl | 3-CF₃ | 359 |
| 131 | A-1 | OCH₂CF₃ | Cl | 3-CN | 344 |
| 132 | A-1 | OCH₂CF₂CF₃ | Cl | 3-CN | 70-73 |
| 133 | A-3A | (CH₂)₃CF₃ | Cl | 3-CN | 94-96 |
| 134 | A-1 | (CH₂)₃CF₃ | Cl | 3-CH₂CH₃ | 359 |
| 135 | A-1 | (CH₂)₃CF₃ | Cl | 3-c-Pr | 371 |
| 136 | A-3A | (CH₂)₂CH₃ | Cl | 3-CF₃ | 345 |
| 137 | A-1 | (CH₂)₃CF₃ | Cl | 3-Cl | 365 |
| 138 | A-1 | (CH₂)₃CF₃ | Cl | 3-Br | 409 |
| 139 | A-3A | H | Cl | 3-Cl | * |
| 140 | A-2 | H | Cl | (m = 0) | * |
| 141 (Ex. 5) | A-2 | (CH₂)₄CH₃ | Cl | (m = 0) | ** |
| 142 | A-3A | (CH₂)₂CF₃ | Cl | 3-CN | 354 |
| 143 | A-3A | (CH₂)₃CF₃ | Cl | 3-Cl | 379 |
| 144 | A-2 | (CH₂)₃CF₃ | Cl | (m = 0) | 356 |
| 145 | A-2 | (CH₂)₄CF₃ | Cl | (m = 0) | 370 |
| 146 | A-7; R¹⁵ is H | (CH₂)₃CF₃ | Cl | 3-CN | 358 |

*See Index Table C for ¹H NMR data. **See Synthesis Example for ¹H NMR data. E indicates E stereochemistry of double bond

INDEX TABLE B

| INCode | Cmpd | Structure | M.S.(AP+) or m.p. |
|---|---|---|---|
| TLU08 | 53 | 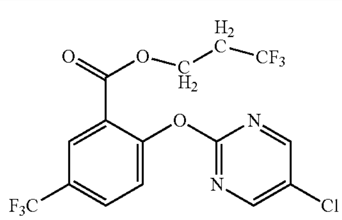 [SMILES: O=C(OCCC(F)(F)F)c1cc(C(F)(F)F)ccc1Oc1ncc(Cl)cn1] | 415 (80-83) |
| TKV38 | 54 | | 361 (78-81) |

INDEX TABLE C

| Cmpd | $^1$H NMR (CDCl$_3$ solution unless indicated otherwise) |
|---|---|
| 1 | 8.48 (s, 2H), 7.53 (dd, 1H), 7.35 (t, 1H), 7.18 (dd, 1H), 4.02 (d, 2H), 1.98-1.83 (m, 1H), 0.89 (d, 6H). |
| 2 | 8.48 (m, 2H), 7.55 (dd, 1H), 7.38 (t, 1H), 7.26 (s, 1H), 7.20 (dd, 1H), 5.55-5.46 (m, 1H), 5.38 (m, 1H), 4.80-4.78 (m, 2H). |
| 3 | 8.47 (s, 2H), 7.54 (dd, 1H), 7.36 (t, 1H), 7.19 (dd, 1H), 4.99-4.93 (m, 1H), 4.91-4.89 (m, 1H), 4.63 (s, 2H), 1.71 (s, 3H). |
| 12 | 8.48 (s, 2H), 7.51 (dd, 1H), 7.32 (t, 1H), 7.15 (dd, 1H), 2.55 (s, 3H). |
| 13 | 8.49 (s, 2H), 7.53 (dd, 1H), 7.35 (t, 1H), 7.18 (dd, 1H), 4.20 (t, 2H), 1.58-1.67 (m, 2H), 0.82-0.93 (m, 3H). |
| 14 | 8.49 (s, 2H), 7.51 (dd, 0.95 Hz, 1H), 7.32 (t, 1H), 7.16 (dd, 1H), 1.43 (s, 9 H). |
| 20 | 8.49 (s, 2H), 7.54 (dd, 1H), 7.37 (t, 1H), 7.20 (dd, 1H), 4.31 (t, 2H), 2.20-2.04 (m, 2H), 1.93-1.85 (m, 2H). |
| 21 | 8.48 (s, 2H), 7.53 (dd, 1H), 7.35 (t, 1H), 7.17 (dd, 1H), 5.75-5.67 (m, 1H), 5.09-5.05 (m, 1H), 5.03-5.00 (m, 1H), 4.29 (t, 2H), 2.39-2.34 (m, 2H). |
| 27 | 8.37 (s, 2H), 7.64 (d, 1H), 7.46 (t, 1H), 7.32 (t, 1H), 7.19 (bs, 1H), 7.00 (d, 1H), 4.75 (q, 2H). |
| 28 | 8.30 (s, 2H), 7.65 (d, 1H), 7.48 (t, 1H), 7.31 (t, 1H), 7.21 (bs, 1H), 7.00 (d, 1H), 4.75 (q, 2H). |
| 31 | 8.81 (s, 2H), 7.63 (dd, 1H), 7.45 (t, 1H), 7.22 (dd, 1H), 4.58 (q, 2H). |
| 40 | 8.50 (s, 2H), 7.57 (dd, 1H), 7.43 (t, 1H), 7.24 (dd, 1H), 4.87 (s, 2H). |
| 99 | 500 MHz) 8.47 (s, 2H) 7.53-7.56 (m, 1H) 7.29-7.33 (m, 1H) 7.14-7.18 (m, 1H) 4.19 (t, 2H) 2.26-2.36 (m, 2H) 2.09 (s, 3H). |
| 139 | 10.39 (s, 1H), 8.49 (s, 2H), 7.62-7.56 (m, 1H), 7.47-7.42 (m, 1H), 7.22-7.17 (m, 1H). |
| 140 | (500 MHz) 8.49 (s, 2H), 7.54-7.58 (m, 1H), 7.40-7.45 (m, 1H), 7.30-7.36 (m, 1H), 7.16-7.20 (m, 1H), 3.72 (s, 2H). |

$^1$H NMR data are in ppm downfield from tetramethylsilane.
Couplings are designated by (s)—singlet, (d)—doublet, (t)—triplet, (m)—multiplet, (dd)—doublet of doublets, (dt)—doublet of triplets, (br s)—broad singlet Biological Examples of the Invention Test A Seeds of plant species selected from barnyardgrass (*Echinochloa crus-galli*), kochia (*Kochia scoparia*), ragweed (common ragweed, *Ambrosia elatior*), Italian ryegrass (*Lolium multiflorum*), large (Lg) crabgrass (*Digitaria sanguinalis*), giant foxtail (*Setaria faberii*), morningglory (*Ipomoea* spp.), pigweed (*Amaranthus retroflexus*), velvetleaf (*Abutilon theophrasti*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant.

At the same time, plants selected from these crop and weed species and also blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| | Compounds | | | | | |
|---|---|---|---|---|---|---|
| 1000 g ai/ha | 12 | 55 | 56 | 57 | 58 | 59 |
| Postemergence | | | | | | |
| Barnyardgrass | 80 | 0 | 50 | 20 | 40 | 0 |
| Blackgrass | 50 | — | — | — | — | — |
| Corn | 20 | 0 | 30 | 20 | 30 | 20 |
| Crabgrass, Large | — | 0 | 40 | 30 | 80 | 10 |
| Foxtail, Giant | 70 | 10 | 70 | 20 | 60 | 10 |
| Galium | 80 | — | — | — | — | — |
| Kochia | 80 | — | — | — | — | — |
| Morningglory | — | — | — | 10 | 30 | 0 |
| Pigweed | 100 | 0 | 60 | 40 | 100 | 30 |
| Ragweed | 60 | — | — | — | — | — |
| Ryegrass, Italian | 50 | — | — | — | — | — |
| Velvetleaf | — | 10 | 100 | — | 90 | — |
| Wheat | 0 | 0 | 10 | 20 | 20 | 30 |

| | Compounds | | | | | | | | | | | | | |
|---|---|---|---|---|---|---|---|---|---|---|---|---|---|---|
| 500 g ai/ha | 6 | 7 | 8 | 9 | 10 | 11 | 13 | 14 | 15 | 16 | 17 | 18 | 20 | 21 |
| Postemergence | | | | | | | | | | | | | | |
| Barnyardgrass | 40 | 90 | 40 | 90 | 100 | 20 | 100 | 40 | 100 | 90 | 0 | 0 | 100 | 100 |
| Blackgrass | 30 | 80 | 20 | 80 | 90 | 20 | 70 | 70 | 100 | 90 | 0 | 0 | 50 | 80 |
| Corn | 10 | 70 | 20 | 50 | 60 | 10 | 90 | 10 | 90 | 60 | 20 | 0 | 40 | 60 |
| Crabgrass, Large | — | — | — | — | — | — | — | — | — | — | — | — | — | — |

TABLE A-continued

| | | | | | | | | | | | | | | |
|---|---|---|---|---|---|---|---|---|---|---|---|---|---|---|
| Foxtail, Giant | 50 | 100 | 60 | 90 | 100 | 20 | 100 | 60 | 100 | 90 | 0 | 0 | 100 | 100 |
| Galium | 90 | 100 | 90 | 100 | 100 | 20 | 100 | 100 | 100 | 100 | 0 | 0 | 90 | 90 |
| Kochia | 90 | 100 | 80 | 90 | 100 | 40 | 100 | 70 | 100 | 100 | 0 | 10 | 100 | 100 |
| Morningglory | — | — | — | — | — | — | — | — | — | — | — | — | — | — |
| Pigweed | 90 | 100 | 90 | 100 | 100 | 60 | 100 | 100 | 100 | 100 | 40 | 20 | 100 | 100 |
| Ragweed | 30 | 90 | 40 | 10 | 50 | 0 | 20 | 0 | 40 | 30 | 0 | 0 | 40 | 40 |
| Ryegrass, Italian | 40 | 70 | 30 | 50 | 60 | 0 | 100 | 70 | 90 | 30 | 0 | 0 | 40 | 90 |
| Velvetleaf | — | — | — | — | — | — | — | — | — | — | — | — | — | — |
| Wheat | 10 | 20 | 0 | 50 | 40 | 0 | 30 | 40 | 100 | 20 | 0 | 0 | 20 | 40 |

| | Compounds | | | | | | | | | | | | | |
|---|---|---|---|---|---|---|---|---|---|---|---|---|---|---|
| 500 g ai/ha | 22 | 23 | 24 | 25 | 26 | 27 | 28 | 30 | 31 | 32 | 33 | 34 | 35 | 39 |

| | Postemergence | | | | | | | | | | | | | |
|---|---|---|---|---|---|---|---|---|---|---|---|---|---|---|
| Barnyardgrass | 100 | 50 | 10 | 10 | 100 | 0 | 20 | 20 | 0 | 0 | 100 | 20 | 80 | 0 |
| Blackgrass | 90 | 50 | 0 | 30 | 100 | — | — | 30 | 0 | 0 | 90 | 70 | 80 | 0 |
| Corn | 50 | 20 | 0 | 20 | 100 | 0 | 0 | 70 | 0 | 0 | 90 | 30 | 30 | 0 |
| Crabgrass, Large | — | — | — | — | — | 0 | 0 | — | — | — | — | — | — | — |
| Foxtail, Giant | 100 | 80 | 0 | 10 | 100 | 0 | 0 | 100 | 0 | 0 | 100 | 80 | 100 | 0 |
| Galium | 90 | 100 | 20 | 50 | 100 | — | — | 100 | 0 | 0 | 100 | 100 | 100 | 0 |
| Kochia | 100 | 100 | 0 | 50 | 100 | — | — | 100 | 0 | 0 | 100 | 90 | 100 | 0 |
| Morningglory | — | — | — | — | — | 0 | 0 | — | — | — | — | — | — | — |
| Pigweed | 100 | 100 | 10 | 60 | 100 | 0 | 20 | 100 | 0 | 30 | 100 | 100 | 100 | 0 |
| Ragweed | 30 | 10 | 0 | 20 | 60 | — | — | 0 | 0 | 0 | 40 | 0 | 0 | 0 |
| Ryegrass, Italian | 60 | 70 | 0 | 0 | 80 | — | — | 0 | 0 | 0 | 80 | 0 | 40 | 0 |
| Velvetleaf | — | — | — | — | — | 0 | 30 | — | — | — | — | — | — | — |
| Wheat | 30 | 10 | 0 | 10 | 90 | 0 | 0 | 30 | 0 | 0 | 60 | 0 | 20 | 0 |

| | Compounds | | | | | | | | | | | | | |
|---|---|---|---|---|---|---|---|---|---|---|---|---|---|---|
| 500 g ai/ha | 40 | 41 | 42 | 47 | 48 | 49 | 61 | 64 | 65 | 72 | 73 | 75 | 78 | 79 |

| | Postemergence | | | | | | | | | | | | | |
|---|---|---|---|---|---|---|---|---|---|---|---|---|---|---|
| Barnyardgrass | 20 | 0 | 0 | 0 | 30 | 0 | 100 | 0 | 70 | 100 | 100 | 100 | 100 | 100 |
| Blackgrass | 20 | 0 | 0 | 0 | 20 | 0 | 100 | 0 | 40 | 50 | 100 | 60 | 60 | 90 |
| Corn | 20 | 0 | 30 | 0 | 0 | 0 | 40 | 0 | 20 | 60 | 60 | 90 | 60 | 90 |
| Crabgrass, Large | — | — | — | — | — | — | — | — | — | — | — | — | — | — |
| Foxtail, Giant | 40 | 0 | 0 | 0 | 20 | 0 | 100 | 0 | 90 | 100 | 100 | 100 | 80 | 80 |
| Galium | 40 | 0 | 0 | 0 | 10 | 0 | 100 | 0 | 70 | 100 | 100 | 100 | 100 | 100 |
| Kochia | 100 | 60 | 60 | 0 | 0 | 0 | — | 0 | — | 100 | 100 | 100 | 100 | 100 |
| Morningglory | — | — | — | — | — | — | — | — | — | — | — | — | — | — |
| Pigweed | 100 | 90 | 90 | 0 | 40 | 0 | 100 | 0 | 100 | 100 | 100 | 100 | 90 | 100 |
| Ragweed | 0 | 10 | 0 | 0 | 0 | 0 | 30 | 0 | 30 | 30 | 40 | 30 | 40 |
| Ryegrass, Italian | 0 | 0 | 0 | 0 | 0 | 0 | 80 | 0 | 0 | 40 | 100 | 70 | 30 | 90 |
| Velvetleaf | — | — | — | — | — | — | — | — | — | — | — | — | — | — |
| Wheat | 20 | 0 | 0 | 0 | 0 | 0 | 30 | 0 | 0 | 40 | 90 | 70 | 30 | 30 |

| | Compounds | | | | | | | | |
|---|---|---|---|---|---|---|---|---|---|
| 500 g ai/ha | 83 | 84 | 85 | 91 | 106 | 125 | 130 | 136 | 139 |

| | Postemergence | | | | | | | | |
|---|---|---|---|---|---|---|---|---|---|
| Barnyardgrass | 90 | 40 | 20 | 100 | 100 | 90 | 100 | 80 | 0 |
| Blackgrass | 40 | 0 | 0 | 30 | 20 | 90 | 90 | 100 | 0 |
| Corn | 30 | 40 | 40 | 50 | 10 | 30 | 50 | 50 | 0 |
| Crabgrass, Large | — | — | — | — | — | — | — | — | — |
| Foxtail, Giant | 80 | 60 | 60 | 100 | 70 | 90 | 90 | 90 | 0 |
| Galium | 20 | 40 | 90 | 90 | 10 | 100 | 100 | 100 | 0 |
| Kochia | 90 | 70 | 80 | 100 | — | 100 | 100 | 100 | 0 |
| Morningglory | — | — | — | — | — | — | — | — | — |
| Pigweed | 70 | 70 | 70 | 100 | 20 | 100 | 100 | 100 | 0 |
| Ragweed | 0 | 0 | 0 | 20 | 0 | 40 | 60 | 60 | 0 |
| Ryegrass, Italian | 0 | 0 | 0 | 30 | 0 | 90 | 90 | 70 | 20 |
| Velvetleaf | — | — | — | — | — | — | — | — | — |
| Wheat | 0 | 20 | 20 | 30 | 0 | 30 | 30 | 20 | 0 |

| | Compounds | | | | | | | | | | | | | |
|---|---|---|---|---|---|---|---|---|---|---|---|---|---|---|
| 125 g ai/ha | 1 | 2 | 3 | 4 | 5 | 6 | 7 | 8 | 9 | 10 | 11 | 13 | 15 | 16 |

| | Postemergence | | | | | | | | | | | | | |
|---|---|---|---|---|---|---|---|---|---|---|---|---|---|---|
| Barnyardgrass | 30 | 40 | 60 | 0 | 0 | 10 | 30 | 10 | 20 | 20 | 10 | 80 | 90 | 10 |
| Blackgrass | 20 | 30 | 30 | 0 | 0 | 10 | 30 | 0 | 30 | 20 | 0 | 30 | 90 | 20 |
| Corn | 20 | 20 | 30 | 0 | 0 | 0 | 10 | 0 | 20 | 10 | 0 | 30 | 50 | 20 |
| Foxtail, Giant | 60 | 60 | 80 | 0 | 0 | 10 | 50 | 30 | 20 | 30 | 20 | 80 | 90 | 20 |

TABLE A-continued

| | | | | | | | | | | | | | | |
|---|---|---|---|---|---|---|---|---|---|---|---|---|---|---|
| Galium | 70 | 90 | 70 | 0 | 0 | 60 | 100 | 60 | 70 | 100 | 10 | 100 | 100 | 90 |
| Kochia | 30 | 90 | 40 | 0 | 0 | 40 | 100 | 40 | 50 | 90 | 0 | 100 | 100 | 80 |
| Pigweed | 70 | 80 | 100 | 0 | 0 | 60 | 100 | 50 | 100 | 90 | 10 | 90 | 100 | 90 |
| Ragweed | 10 | 0 | 0 | 0 | 0 | 10 | 40 | 10 | 0 | 10 | 0 | 0 | 20 | 10 |
| Ryegrass, Italian | 0 | 20 | 30 | 0 | 0 | 0 | 20 | 0 | 0 | 10 | 0 | 0 | 60 | 10 |
| Wheat | 0 | 0 | 0 | 0 | 0 | 0 | 0 | 0 | 10 | 0 | 0 | 20 | 20 | 20 |

| | Compounds | | | | | | | | | | | | | |
|---|---|---|---|---|---|---|---|---|---|---|---|---|---|---|
| 125 g ai/ha | 17 | 18 | 19 | 20 | 21 | 22 | 23 | 24 | 25 | 26 | 30 | 31 | 32 | 33 |
| | Postemergence | | | | | | | | | | | | | |
| Barnyardgrass | 0 | 0 | 0 | 30 | 70 | 60 | 10 | 0 | 0 | 100 | 0 | 0 | 0 | 80 |
| Blackgrass | 0 | 0 | 0 | 30 | 60 | 60 | 10 | 0 | 0 | 100 | 10 | 0 | 0 | 60 |
| Corn | 0 | 0 | 0 | 30 | 30 | 30 | 10 | 0 | 0 | 60 | 30 | 0 | 0 | 30 |
| Foxtail, Giant | 0 | 0 | 0 | 50 | 70 | 80 | 30 | 0 | 0 | 100 | 60 | 0 | 0 | 100 |
| Galium | 0 | 0 | 0 | 10 | 80 | 30 | 90 | 10 | 20 | 100 | 60 | 0 | 0 | 100 |
| Kochia | 0 | 0 | 0 | 90 | 90 | 90 | 80 | 0 | 10 | 100 | 100 | 0 | 0 | 100 |
| Pigweed | 20 | 10 | 10 | 100 | 80 | 100 | 100 | 0 | 30 | 100 | 100 | 0 | 20 | 100 |
| Ragweed | 0 | 0 | 0 | 0 | 0 | 0 | 0 | 0 | 10 | 30 | 0 | 0 | 0 | 30 |
| Ryegrass, Italian | 0 | 0 | 0 | 0 | 0 | 0 | 10 | 0 | 0 | 70 | 0 | 0 | 0 | 30 |
| Wheat | 0 | 0 | 0 | 0 | 0 | 0 | 0 | 0 | 0 | 40 | 0 | 0 | 0 | 20 |

| | Compounds | | | | | | | | | | | | | |
|---|---|---|---|---|---|---|---|---|---|---|---|---|---|---|
| 125 g ai/ha | 34 | 35 | 36 | 37 | 38 | 39 | 40 | 41 | 42 | 43 | 44 | 45 | 46 | 47 |
| | Postemergence | | | | | | | | | | | | | |
| Barnyardgrass | 0 | 10 | 0 | 30 | 60 | 0 | 0 | 0 | 0 | 10 | 0 | 20 | 30 | 0 |
| Blackgrass | 10 | 40 | 0 | 30 | 0 | 0 | 10 | 0 | 0 | 0 | 0 | 0 | 0 | 0 |
| Corn | 30 | 20 | 0 | 10 | 10 | 0 | 20 | 0 | 20 | 0 | 0 | 20 | 10 | 0 |
| Foxtail, Giant | 20 | 40 | 0 | 40 | 90 | 0 | 10 | 0 | 0 | 0 | 0 | 20 | 40 | 0 |
| Galium | 50 | 60 | 0 | 40 | 80 | 0 | 30 | 0 | 0 | 40 | 0 | 100 | 70 | 0 |
| Kochia | 60 | 90 | 0 | 40 | 60 | 0 | 70 | 20 | 30 | 10 | 0 | 50 | 90 | 0 |
| Pigweed | 100 | 100 | 60 | 80 | 100 | 0 | 70 | 90 | 80 | 40 | 0 | 100 | 100 | 0 |
| Ragweed | 0 | 0 | 0 | 0 | 10 | 0 | 0 | 0 | 0 | 0 | 0 | 10 | 0 | 0 |
| Ryegrass, Italian | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 48 | 49 | 50 | 51 | 53 | 54 | 61 | 62 | 63 | 64 | 65 | 66 | 67 | 68 |
| | Postemergence | | | | | | | | | | | | | |
| Barnyardgrass | 0 | 0 | 20 | 0 | 0 | 0 | 100 | 40 | 10 | 0 | 30 | 100 | 0 | 30 |
| Blackgrass | 0 | 0 | 20 | 0 | 0 | 0 | 30 | 40 | 0 | 0 | 20 | 100 | 0 | 30 |
| Corn | 0 | 0 | 10 | 0 | 0 | 0 | 20 | 30 | 30 | 0 | 10 | 70 | 0 | 20 |
| Foxtail, Giant | 0 | 0 | 70 | 0 | 0 | 0 | 60 | 40 | 30 | 0 | 40 | 100 | 0 | 30 |
| Galium | 0 | 0 | 90 | 10 | 0 | 0 | 60 | 80 | 30 | 0 | 20 | 100 | 0 | 60 |
| Kochia | 0 | 0 | 90 | 0 | 0 | 0 | — | 100 | 50 | 0 | — | 50 | 0 | 40 |
| Pigweed | 20 | 0 | 100 | 0 | 0 | 0 | 40 | 90 | 60 | 0 | 90 | 100 | 0 | 90 |
| Ragweed | 0 | 0 | 0 | 0 | 0 | 0 | 10 | 0 | 0 | 0 | 10 | 20 | 0 | 20 |
| Ryegrass, Italian | 0 | 0 | 20 | 0 | 0 | 0 | 20 | 0 | 0 | 0 | 0 | 50 | 0 | 0 |
| Wheat | 0 | 0 | 0 | 0 | 0 | 0 | 0 | 0 | 0 | 0 | 0 | 30 | 0 | 0 |

| | Compounds | | | | | | | | | | | | | |
|---|---|---|---|---|---|---|---|---|---|---|---|---|---|---|
| 125 g ai/ha | 69 | 70 | 71 | 72 | 73 | 74 | 75 | 76 | 77 | 78 | 79 | 80 | 81 | 82 |
| | Postemergence | | | | | | | | | | | | | |
| Barnyardgrass | 70 | 30 | 40 | 80 | 90 | 40 | 90 | 0 | 90 | 60 | 90 | 90 | 50 | 100 |
| Blackgrass | 30 | 20 | 30 | 30 | 50 | 30 | 40 | 0 | 50 | 20 | 50 | 90 | 40 | 40 |
| Corn | 20 | 10 | 20 | 50 | 30 | 20 | 80 | 0 | 30 | 40 | 80 | 60 | 40 | 30 |
| Foxtail, Giant | 30 | 30 | 40 | 70 | 100 | 70 | 90 | 0 | 90 | 50 | 90 | 90 | 70 | 100 |
| Galium | 60 | 70 | 90 | 80 | 100 | 80 | 80 | 90 | 100 | 70 | 90 | 90 | 80 | 100 |
| Kochia | 40 | 70 | 50 | 100 | 100 | 40 | 100 | 0 | 100 | 70 | 100 | 70 | 50 | 100 |
| Pigweed | 80 | 20 | 70 | 100 | 100 | 100 | 100 | 30 | 100 | 80 | 100 | 100 | 100 | 100 |
| Ragweed | 0 | 20 | 20 | 10 | 20 | 10 | 30 | 0 | 0 | 0 | 30 | 30 | 10 | 40 |
| Ryegrass, Italian | 0 | 20 | 20 | 10 | 80 | 20 | 40 | 0 | 60 | 0 | 90 | 50 | 10 | 60 |
| Wheat | 0 | 0 | 0 | 10 | 20 | 10 | 20 | 0 | 10 | 20 | 20 | 40 | 0 | 30 |

TABLE A-continued

| 125 g ai/ha | Compounds | | | | | | | | | | | | | |
|---|---|---|---|---|---|---|---|---|---|---|---|---|---|---|
| | 83 | 84 | 85 | 86 | 87 | 88 | 89 | 90 | 91 | 92 | 93 | 94 | 95 | 96 |
| Postemergence | | | | | | | | | | | | | | |
| Barnyardgrass | 0 | 0 | 0 | 40 | 100 | 0 | 90 | 30 | 30 | 100 | 0 | 0 | 30 | 10 |
| Blackgrass | 0 | 0 | 0 | 20 | 70 | 0 | 60 | 0 | 20 | 50 | 0 | 0 | 10 | 10 |
| Corn | 20 | 10 | 10 | 30 | 50 | 0 | 20 | 10 | 20 | 40 | 0 | 0 | 10 | 20 |
| Foxtail, Giant | 0 | 0 | 0 | 30 | 90 | 0 | 50 | 60 | 30 | 100 | 0 | 0 | 60 | 10 |
| Galium | 30 | 30 | 30 | 70 | 70 | 0 | 80 | 20 | 70 | 100 | 0 | 0 | 40 | 20 |
| Kochia | 30 | 30 | 30 | 100 | 100 | 0 | 90 | 50 | 60 | 100 | 0 | 0 | 0 | 0 |
| Pigweed | 30 | 30 | 30 | 40 | 60 | 0 | 90 | 50 | 100 | 100 | 0 | 0 | 20 | 10 |
| Ragweed | 0 | 0 | 0 | 0 | 0 | 0 | 10 | 0 | 0 | 20 | 0 | 0 | 0 | 0 |
| Ryegrass, Italian | 0 | 0 | 0 | 20 | 30 | 0 | 30 | 0 | 0 | 50 | 0 | 0 | 0 | 0 |
| Wheat | 0 | 0 | 0 | 40 | 30 | 0 | 20 | 0 | 20 | 20 | 0 | 0 | 0 | 0 |

| 125 g ai/ha | Compounds | | | | | | | | | | | | | |
|---|---|---|---|---|---|---|---|---|---|---|---|---|---|---|
| | 97 | 98 | 99 | 100 | 101 | 102 | 103 | 104 | 105 | 106 | 107 | 108 | 109 | 110 |
| Postemergence | | | | | | | | | | | | | | |
| Barnyardgrass | 20 | 10 | 80 | 50 | 20 | 0 | 30 | 0 | 0 | 40 | 90 | 10 | 0 | 60 |
| Blackgrass | 20 | 10 | 80 | 40 | 0 | 0 | 10 | 20 | 10 | 0 | 90 | 10 | 0 | 50 |
| Corn | 10 | 10 | 50 | 10 | 0 | 0 | 20 | 10 | 0 | 0 | 60 | 20 | 20 | 50 |
| Foxtail, Giant | 60 | 20 | 90 | 70 | 20 | 0 | 70 | 10 | 0 | 10 | 90 | 10 | 0 | 90 |
| Galium | 100 | 50 | 70 | 70 | 40 | 0 | 100 | 30 | 20 | 0 | 90 | 40 | 30 | 100 |
| Kochia | 40 | 0 | 40 | 80 | 20 | 0 | 100 | 10 | 10 | — | 90 | 40 | 20 | 100 |
| Pigweed | 50 | 90 | 40 | 70 | 60 | 0 | 100 | 40 | 30 | 10 | 100 | 50 | 60 | 100 |
| Ragweed | 20 | 10 | 30 | 0 | 0 | 0 | 0 | 0 | 0 | 0 | 30 | 0 | 20 | 0 |
| Ryegrass, Italian | 30 | 0 | 50 | 20 | 10 | 0 | 0 | 0 | 0 | 0 | 80 | 0 | 0 | 20 |
| Wheat | 0 | 10 | 30 | 0 | 0 | 0 | 0 | 0 | 0 | 0 | 30 | 0 | 0 | 20 |

| 125 g ai/ha | Compounds | | | | | | | | | | | | | |
|---|---|---|---|---|---|---|---|---|---|---|---|---|---|---|
| | 111 | 112 | 113 | 114 | 115 | 116 | 117 | 118 | 119 | 120 | 121 | 122 | 123 | 124 |
| Postemergence | | | | | | | | | | | | | | |
| Barnyardgrass | 0 | 10 | 40 | 10 | 0 | 10 | 10 | 10 | 0 | 0 | 40 | 50 | 50 | 60 |
| Blackgrass | 0 | 30 | 40 | 10 | 20 | 0 | 10 | 0 | 0 | 0 | 30 | 60 | 50 | 60 |
| Corn | 0 | 0 | 20 | 20 | 10 | 10 | 10 | 10 | 20 | 0 | 10 | 20 | 10 | 20 |
| Foxtail, Giant | 0 | 30 | 50 | 20 | 0 | 20 | 10 | 10 | 0 | 0 | 70 | 40 | 50 | 70 |
| Galium | 0 | 80 | 80 | 80 | 20 | 60 | 100 | 30 | 90 | 30 | 80 | 60 | 100 | 90 |
| Kochia | 0 | 30 | 100 | 80 | 0 | 10 | 50 | 60 | 30 | 0 | 80 | 80 | 90 | 80 |
| Pigweed | 0 | 70 | 100 | 100 | 40 | 50 | 70 | 60 | 100 | 20 | 100 | 100 | 100 | 100 |
| Ragweed | 0 | 40 | 20 | 20 | 0 | 0 | 20 | 10 | 10 | 0 | 50 | 10 | 10 | 20 |
| Ryegrass, Italian | 0 | 0 | 30 | 10 | 0 | 0 | 0 | 0 | 0 | 0 | 20 | 20 | 20 | 20 |
| Wheat | 0 | 0 | 20 | 10 | 0 | 0 | 0 | 0 | 0 | 0 | 10 | 0 | 0 | 10 |

| 125 g ai/ha | Compounds | | | | | | | | | | | | | |
|---|---|---|---|---|---|---|---|---|---|---|---|---|---|---|
| | 125 | 126 | 127 | 128 | 129 | 130 | 131 | 132 | 133 | 134 | 135 | 136 | 137 | 138 |
| Postemergence | | | | | | | | | | | | | | |
| Barnyardgrass | 30 | 0 | 30 | 20 | 100 | 90 | 10 | 50 | 30 | 20 | 10 | 30 | 60 | 90 |
| Blackgrass | 30 | 0 | 20 | 20 | 80 | 50 | 0 | 30 | 0 | 20 | 20 | 50 | 30 | 90 |
| Corn | 10 | 0 | 20 | 10 | 20 | 20 | 30 | 30 | 20 | 10 | 20 | 20 | 10 | 60 |
| Foxtail, Giant | 50 | 0 | 50 | 20 | 100 | 40 | 20 | 50 | 30 | 20 | 20 | 30 | 60 | 90 |
| Galium | 100 | 0 | 90 | 80 | 90 | 100 | 50 | 60 | 50 | 40 | 80 | 40 | 100 | 100 |
| Kochia | 100 | 0 | 60 | 60 | 100 | 100 | 90 | 70 | 20 | 60 | 60 | 80 | 100 | 100 |
| Pigweed | 100 | 10 | 30 | 50 | 70 | 100 | 80 | 90 | 50 | 80 | 90 | 100 | 100 | 100 |
| Ragweed | 30 | 0 | 0 | 0 | 0 | 30 | 0 | 0 | 0 | 10 | 10 | 20 | 40 | 60 |
| Ryegrass, Italian | 20 | 0 | 0 | 0 | 60 | 20 | 20 | 0 | 0 | 10 | 10 | 10 | 30 | 100 |
| Wheat | 20 | 0 | 10 | 10 | 10 | 30 | 20 | 20 | 0 | 10 | 0 | 10 | 10 | 40 |

| 125 g ai/ha | Compounds | | | | | | | |
|---|---|---|---|---|---|---|---|---|
| | 139 | 140 | 141 | 142 | 143 | 144 | 145 | 146 |
| Postemergence | | | | | | | | |
| Barnyardgrass | 0 | 0 | 20 | 0 | 70 | 90 | 80 | 90 |
| Blackgrass | 0 | 0 | 10 | 0 | 80 | 90 | 60 | 90 |
| Corn | 0 | 0 | 20 | 10 | 30 | 80 | 50 | 80 |
| Foxtail, Giant | 0 | 0 | 40 | 0 | 70 | 90 | 70 | 90 |
| Galium | 0 | 0 | 60 | 20 | 100 | 100 | 80 | 100 |
| Kochia | 0 | 30 | 60 | 10 | 100 | 100 | 90 | 100 |

TABLE A-continued

|  |  |  |  |  |  |  |  |  |
|---|---|---|---|---|---|---|---|---|
| Pigweed | 0 | 20 | 70 | 20 | 100 | 100 | 100 | 70 |
| Ragweed | 0 | 0 | 20 | 20 | 50 | 10 | 20 | 30 |
| Ryegrass, Italian | 0 | 0 | 10 | 0 | 80 | 80 | 40 | 70 |
| Wheat | 0 | 0 | 0 | 0 | 20 | 60 | 30 | 20 |

| | Compounds | | | | | | | | | | | | | |
|---|---|---|---|---|---|---|---|---|---|---|---|---|---|---|
| 31 g ai/ha | 1 | 2 | 3 | 4 | 5 | 19 | 36 | 37 | 38 | 43 | 44 | 45 | 46 | 50 |
| | Postemergence | | | | | | | | | | | | | |
| Barnyardgrass | 20 | 30 | 20 | 0 | 0 | 0 | 0 | 0 | 10 | 0 | 0 | 20 | 0 | 0 |
| Blackgrass | 0 | 0 | 0 | 0 | 0 | 0 | 0 | 0 | 0 | 0 | 0 | 0 | 0 | 0 |
| Corn | 0 | 10 | 0 | 0 | 0 | 0 | 0 | 0 | 0 | 0 | 0 | 0 | 0 | 10 |
| Foxtail, Giant | 30 | 30 | 30 | 0 | 0 | 0 | 0 | 0 | 40 | 0 | 0 | 20 | 0 | 20 |
| Galium | 50 | 60 | 40 | 0 | 0 | 0 | 0 | 10 | 50 | 20 | 0 | 50 | 50 | 60 |
| Kochia | 20 | 50 | 0 | 0 | 0 | 0 | 0 | 0 | 30 | 0 | 0 | 20 | 30 | 60 |
| Pigweed | 40 | 60 | 70 | 0 | 0 | 10 | 0 | 20 | 80 | 10 | 0 | 80 | 60 | 80 |
| Ragweed | 0 | 0 | 0 | 0 | 0 | 0 | 0 | 0 | 0 | 0 | 0 | 10 | 0 | 0 |
| Ryegrass, Italian | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 51 | 53 | 54 | 62 | 63 | 66 | 67 | 68 | 69 | 70 | 71 | 74 | 76 | 77 |
| | Postemergence | | | | | | | | | | | | | |
| Barnyardgrass | 0 | 0 | 0 | 20 | 0 | 40 | 0 | 10 | 10 | 0 | 0 | 10 | 0 | 30 |
| Blackgrass | 0 | 0 | 0 | 0 | 0 | 10 | 0 | 10 | 10 | 0 | 10 | 10 | 0 | 20 |
| Corn | 0 | 0 | 0 | 0 | 10 | 20 | 0 | 10 | 0 | 10 | 10 | 10 | 0 | 10 |
| Foxtail, Giant | 0 | 0 | 0 | 0 | 0 | 30 | 0 | 20 | 20 | 0 | 10 | 20 | 0 | 30 |
| Galium | 0 | 0 | 0 | 30 | 0 | 30 | 0 | 20 | 40 | 30 | 30 | 20 | 0 | 90 |
| Kochia | 0 | 0 | 0 | 60 | 20 | 20 | 0 | 20 | 20 | 20 | 10 | 20 | 0 | 100 |
| Pigweed | 0 | 0 | 0 | 50 | 20 | 40 | 0 | 20 | 40 | 10 | 30 | 60 | 0 | 100 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 20 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 80 | 81 | 82 | 86 | 87 | 88 | 89 | 90 | 92 | 93 | 94 | 95 | 96 | 97 |
| | Postemergence | | | | | | | | | | | | | |
| Barnyardgrass | 30 | 10 | 30 | 20 | 40 | 0 | 30 | 0 | 40 | 0 | 0 | 0 | 0 | 10 |
| Blackgrass | 30 | 10 | 40 | 0 | 10 | 0 | 20 | 0 | 10 | 0 | 0 | 0 | 0 | 0 |
| Corn | 10 | 10 | 20 | 30 | 40 | 0 | 10 | 0 | 10 | 0 | 0 | 0 | 0 | 10 |
| Foxtail, Giant | 30 | 20 | 30 | 10 | 40 | 0 | 20 | 10 | 50 | 0 | 0 | 0 | 0 | 10 |
| Galium | 60 | 30 | 90 | 30 | 30 | 0 | 30 | 0 | 90 | 0 | 0 | 10 | 0 | 100 |
| Kochia | 50 | 30 | 80 | 90 | 100 | 0 | 80 | 30 | 100 | 0 | 0 | 0 | 0 | — |
| Pigweed | 80 | 50 | 100 | 30 | 40 | 0 | 90 | 10 | 100 | 0 | 0 | 10 | 0 | 20 |
| Ragweed | 10 | 0 | 40 | 0 | 0 | 0 | 10 | 0 | 0 | 0 | 0 | 0 | 0 | 10 |
| Ryegrass, Italian | 0 | 0 | 40 | 0 | 0 | 0 | 10 | 0 | 0 | 0 | 0 | 0 | 0 | 20 |
| Wheat | 0 | 0 | 10 | 30 | 20 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 98 | 99 | 100 | 101 | 102 | 103 | 104 | 105 | 107 | 108 | 109 | 110 | 111 | 112 |
| | Postemergence | | | | | | | | | | | | | |
| Barnyardgrass | 0 | 30 | 10 | 10 | 0 | 0 | 0 | 0 | 40 | 0 | 0 | 30 | 0 | 0 |
| Blackgrass | 0 | 30 | 0 | 0 | 0 | 0 | 0 | 0 | 50 | 0 | 0 | 0 | 0 | 0 |
| Corn | 0 | 0 | 10 | 0 | 0 | 20 | 0 | 0 | 30 | 10 | 10 | 20 | 0 | 0 |
| Foxtail, Giant | 0 | 50 | 20 | 0 | 0 | 10 | 0 | 0 | 70 | 0 | 0 | 30 | 0 | 0 |
| Galium | 10 | 20 | 20 | 10 | 0 | 70 | 10 | 10 | 90 | 20 | 0 | 70 | 0 | 60 |
| Kochia | 0 | 20 | 60 | 0 | 0 | 70 | 0 | 0 | 90 | 20 | 0 | 100 | 0 | 0 |
| Pigweed | 30 | 10 | 30 | 20 | 0 | 90 | 10 | 10 | 100 | 20 | 20 | 90 | 0 | 40 |
| Ragweed | 0 | 10 | 0 | 0 | 0 | 0 | 0 | 0 | 20 | 0 | 0 | 0 | 0 | 20 |
| Ryegrass, Italian | 0 | 0 | 0 | 0 | 0 | 0 | 0 | 0 | 20 | 0 | 0 | 0 | 0 | 0 |
| Wheat | 0 | 0 | 0 | 0 | 0 | 0 | 0 | 0 | 0 | 0 | 0 | 0 | 0 | 0 |

TABLE A-continued

| 31 g ai/ha | Compounds | | | | | | | | | | | | | |
|---|---|---|---|---|---|---|---|---|---|---|---|---|---|---|
| | 113 | 114 | 115 | 116 | 117 | 118 | 119 | 120 | 121 | 122 | 123 | 124 | 126 | 127 |
| | Postemergence | | | | | | | | | | | | | |
| Barnyardgrass | 10 | 0 | 0 | 0 | 0 | 0 | 0 | 0 | 20 | 10 | 10 | 10 | 0 | 10 |
| Blackgrass | 0 | 0 | 0 | 0 | 0 | 0 | 0 | 0 | 20 | 20 | 10 | 20 | 0 | 10 |
| Corn | 10 | 10 | 0 | 0 | 10 | 0 | 10 | 0 | 10 | 10 | 10 | 10 | 0 | 10 |
| Foxtail, Giant | 10 | 0 | 0 | 0 | 0 | 0 | 0 | 0 | 10 | 10 | 20 | 30 | 0 | 10 |
| Galium | 40 | 50 | 20 | 30 | 60 | 10 | 10 | 0 | 70 | 30 | 90 | 70 | 0 | 60 |
| Kochia | 80 | 20 | 0 | 0 | 20 | 30 | 30 | 0 | 20 | 80 | 50 | 50 | 0 | 10 |
| Pigweed | 90 | 50 | 10 | 40 | 30 | 40 | 70 | 0 | 80 | 70 | 70 | 70 | 0 | 20 |
| Ragweed | 0 | 0 | 0 | 0 | 0 | 0 | 0 | 0 | 20 | 0 | 0 | 10 | 0 | 0 |
| Ryegrass, Italian | 0 | 0 | 0 | 0 | 0 | 0 | 0 | 0 | 10 | 0 | 0 | 0 | 0 | 0 |
| Wheat | 0 | 0 | 0 | 0 | 0 | 0 | 0 | 0 | 10 | 0 | 0 | 10 | 0 | 0 |

| 31 g ai/ha | Compounds | | | | | | | | | | | | | |
|---|---|---|---|---|---|---|---|---|---|---|---|---|---|---|
| | 128 | 129 | 131 | 132 | 133 | 134 | 135 | 137 | 138 | 140 | 141 | 142 | 143 | 144 |
| | Postemergence | | | | | | | | | | | | | |
| Barnyardgrass | 0 | 20 | 0 | 30 | 10 | 0 | 0 | 20 | 90 | 0 | 10 | 0 | 20 | 40 |
| Blackgrass | 0 | 20 | 0 | 0 | 0 | 10 | 0 | 10 | 40 | 0 | 0 | 0 | 30 | 50 |
| Corn | 10 | 20 | 20 | 20 | 0 | 10 | 10 | 10 | 30 | 0 | 10 | 0 | 10 | 20 |
| Foxtail, Giant | 10 | 20 | 0 | 30 | 10 | 10 | 10 | 10 | 90 | 0 | 20 | 0 | 30 | 60 |
| Galium | 20 | 30 | 20 | 20 | 30 | 10 | 50 | 40 | 70 | 0 | 40 | 0 | 90 | 40 |
| Kochia | 10 | 40 | 40 | 40 | 0 | 20 | 10 | 90 | 90 | 0 | 50 | 0 | 90 | 90 |
| Pigweed | 20 | 20 | 50 | 60 | 30 | 40 | 40 | 80 | 100 | 0 | 40 | 0 | 100 | 90 |
| Ragweed | 0 | 0 | 0 | 0 | 0 | 0 | 0 | 10 | 30 | 0 | 0 | 0 | 20 | 10 |
| Ryegrass, Italian | 0 | 0 | 0 | 0 | 0 | 0 | 0 | 10 | 30 | 0 | 0 | 0 | 20 | 30 |
| Wheat | 0 | 0 | 0 | 0 | 0 | 0 | 0 | 0 | 20 | 0 | 0 | 0 | 10 | 10 |

| 31 g ai/ha | Compounds | | 1000 g ai/ha | Compounds | | | | |
|---|---|---|---|---|---|---|---|---|
| | 145 | 146 | | 12 | 55 | 56 | 57 | 58 | 59 |
| | Postemergence | | | Preemergence | | | | | |
| Barnyardgrass | 30 | 30 | Barnyardgrass | 80 | 0 | 90 | 50 | 90 | 20 |
| Blackgrass | 40 | 30 | Corn | — | 0 | 0 | 0 | 20 | 0 |
| Corn | 30 | 20 | Crabgrass, Large | — | 0 | 100 | 100 | 100 | 80 |
| Foxtail, Giant | 50 | 30 | Foxtail, Giant | 100 | 0 | 100 | 90 | 100 | 30 |
| Galium | 40 | 70 | Kochia | 0 | — | — | — | — | — |
| Kochia | 70 | 70 | Morningglory | — | — | — | 0 | 0 | 0 |
| Pigweed | 90 | 60 | Pigweed | 100 | 0 | 100 | 60 | 50 | 30 |
| Ragweed | 10 | 0 | Ragweed | 80 | — | — | — | — | — |
| Ryegrass, Italian | 10 | 0 | Ryegrass, Italian | 40 | — | — | — | — | — |
| Wheat | 10 | 20 | Velvetleaf | — | 0 | 90 | 20 | 20 | 0 |
| | | | Wheat | — | 0 | 0 | 0 | 20 | 0 |

| 500 g ai/ha | Compounds | | | | | | | | | | | | | |
|---|---|---|---|---|---|---|---|---|---|---|---|---|---|---|
| | 6 | 7 | 8 | 9 | 10 | 11 | 13 | 14 | 15 | 16 | 17 | 18 | 20 | 21 |
| | Preemergence | | | | | | | | | | | | | |
| Barnyardgrass | 60 | 100 | 100 | 90 | 100 | 30 | 100 | 60 | 100 | 100 | 0 | 0 | 100 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 100 | 100 | 100 | 100 | 100 | 100 | 100 | 100 | 100 | 0 | 0 | 100 | 100 |
| Kochia | 0 | 100 | 0 | 100 | 100 | 0 | 100 | 70 | 100 | 80 | 0 | 10 | 100 | 100 |
| Morningglory | — | — | — | — | — | — | — | — | — | — | — | — | — | — |
| Pigweed | 70 | 100 | 60 | 100 | 100 | 20 | 100 | 100 | 100 | 100 | 10 | 40 | 100 | 100 |
| Ragweed | 0 | 50 | 0 | 0 | 0 | 0 | 0 | 10 | 10 | 0 | 0 | 0 | 0 | 0 |
| Ryegrass, Italian | 70 | 30 | 30 | 30 | 30 | 0 | 90 | 20 | 90 | 20 | 0 | 0 | 90 | 90 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| | 22 | 23 | 24 | 25 | 26 | 27 | 28 | 30 | 31 | 32 | 33 | 34 | 35 | 39 |
| | Preemergence | | | | | | | | | | | | | |
| Barnyardgrass | 100 | 70 | 30 | 30 | 100 | 0 | 20 | 0 | 0 | 0 | 100 | 90 | 90 | 0 |
| Corn | — | — | — | — | — | 0 | 0 | — | — | — | — | — | — | — |
| Crabgrass, Large | — | — | — | — | — | 0 | 50 | — | — | — | — | — | — | — |
| Foxtail, Giant | 100 | 100 | 20 | 60 | 100 | 0 | 20 | 100 | 0 | 0 | 100 | 100 | 100 | 0 |

TABLE A-continued

| | | | | | | | | | | | | | | |
|---|---|---|---|---|---|---|---|---|---|---|---|---|---|---|
| Kochia | 100 | 50 | 0 | 50 | 100 | — | — | 100 | 0 | 0 | 100 | 40 | 80 | 0 |
| Morningglory | — | — | — | — | — | 0 | 0 | — | — | — | — | — | — | — |
| Pigweed | 100 | 100 | 90 | 80 | 100 | 0 | 80 | 100 | 0 | 30 | 100 | 100 | 100 | 0 |
| Ragweed | 0 | 10 | 0 | 0 | 20 | — | — | 0 | 0 | 0 | 20 | 0 | 0 | 0 |
| Ryegrass, Italian | 90 | 40 | 0 | 0 | 100 | — | — | 0 | 0 | 0 | 100 | 0 | 30 | 0 |
| Velvetleaf | — | — | — | — | — | 0 | 20 | — | — | — | — | — | — | — |
| Wheat | — | — | — | — | — | 0 | 0 | — | — | — | — | — | — | — |

| | Compounds | | | | | | | | | | | | |
|---|---|---|---|---|---|---|---|---|---|---|---|---|---|
| 500 g ai/ha | 40 | 41 | 42 | 47 | 48 | 49 | 61 | 64 | 65 | 72 | 73 | 75 | 78 | 79 |
| | Preemergence | | | | | | | | | | | | |
| Barnyardgrass | 50 | 0 | 0 | 0 | 10 | 0 | 100 | 0 | 100 | 100 | 100 | 100 | 100 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 0 | 0 | 0 | 10 | 0 | 100 | 0 | 100 | 100 | 100 | 100 | 100 | 100 |
| Kochia | 90 | 30 | 0 | 0 | 0 | 0 | 100 | 0 | 90 | 100 | 100 | 100 | 60 | 100 |
| Morningglory | — | — | — | — | — | — | — | — | — | — | — | — | — | — |
| Pigweed | 100 | 40 | 30 | 0 | 0 | 0 | 100 | 0 | 100 | 100 | 100 | 100 | 100 | 100 |
| Ragweed | 0 | 80 | 0 | 0 | 0 | 0 | 20 | 0 | 80 | 10 | 50 | 10 | 0 | 90 |
| Ryegrass, Italian | 0 | 0 | 0 | 0 | 0 | 0 | 80 | 0 | 30 | 30 | 90 | 100 | 20 | 100 |
| Velvetleaf | — | — | — | — | — | — | — | — | — | — | — | — | — | — |
| Wheat | — | — | — | — | — | — | — | — | — | — | — | — | — | — |

| | Compounds | | | | | | | | |
|---|---|---|---|---|---|---|---|---|---|
| 500 g ai/ha | 83 | 84 | 85 | 91 | 106 | 125 | 130 | 136 | 139 |
| | Preemergence | | | | | | | | |
| Barnyardgrass | 90 | 90 | 10 | 100 | 100 | 100 | 100 | 100 | 0 |
| Corn | — | — | — | — | — | — | — | — | — |
| Crabgrass, Large | — | — | — | — | — | — | — | — | — |
| Foxtail, Giant | 100 | 100 | 70 | 100 | 100 | 100 | 100 | 100 | 0 |
| Kochia | 0 | 0 | 0 | 100 | 90 | 100 | 100 | 100 | 0 |
| Morningglory | — | — | — | — | — | — | — | — | — |
| Pigweed | 90 | 100 | 60 | 100 | 70 | 100 | 100 | 100 | 0 |
| Ragweed | 0 | 0 | 0 | 0 | 0 | 40 | 90 | 80 | 0 |
| Ryegrass, Italian | 0 | 0 | 0 | 80 | 10 | 100 | 100 | 100 | 0 |
| Velvetleaf | — | — | — | — | — | — | — | — | — |
| Wheat | — | — | — | — | — | — | — | — | — |

| | Compounds | | | | | | | | | | | | |
|---|---|---|---|---|---|---|---|---|---|---|---|---|---|
| 125 g ai/ha | 1 | 2 | 3 | 4 | 5 | 6 | 7 | 8 | 9 | 10 | 11 | 13 | 15 | 16 |
| | Preemergence | | | | | | | | | | | | |
| Barnyardgrass | 30 | 50 | 80 | 0 | 0 | 10 | 50 | 30 | 40 | 40 | 0 | 100 | 100 | 30 |
| Foxtail, Giant | 70 | 100 | 100 | 0 | 0 | 60 | 90 | 100 | 100 | 100 | 40 | 100 | 100 | 90 |
| Kochia | 40 | 70 | 40 | 0 | 0 | 0 | 50 | 0 | 70 | 90 | 0 | 90 | 100 | 90 |
| Pigweed | 70 | 90 | 100 | 0 | 0 | 10 | 100 | 10 | 100 | 100 | 0 | 100 | 100 | 90 |
| Ragweed | 0 | 0 | 0 | 0 | 0 | 0 | — | 0 | 0 | 0 | 0 | 0 | 0 | 0 |
| Ryegrass, Italian | 0 | 10 | 30 | 0 | 0 | 0 | 0 | 0 | 10 | 10 | 0 | 10 | 40 | 0 |

| | Compounds | | | | | | | | | | | | |
|---|---|---|---|---|---|---|---|---|---|---|---|---|---|
| 125 g ai/ha | 17 | 18 | 19 | 20 | 21 | 22 | 23 | 24 | 25 | 26 | 30 | 31 | 32 | 33 |
| | Preemergence | | | | | | | | | | | | |
| Barnyardgrass | 0 | 0 | 0 | 100 | 100 | 40 | 20 | 0 | 0 | 100 | 0 | 0 | 0 | 100 |
| Foxtail, Giant | 0 | 0 | 0 | 100 | 100 | 100 | 70 | 0 | 10 | 100 | 100 | 0 | 0 | 100 |
| Kochia | 0 | 0 | 20 | 30 | 40 | 30 | 0 | 0 | 0 | 100 | 90 | 0 | 0 | 60 |
| Pigweed | 0 | 10 | 20 | 100 | 100 | 100 | 100 | 0 | 40 | 100 | 100 | 0 | 30 | 100 |
| Ragweed | 0 | 0 | 0 | 0 | 0 | 0 | 0 | 0 | 0 | 20 | 0 | 0 | 0 | 0 |
| Ryegrass, Italian | 0 | 0 | 0 | 30 | 30 | 30 | 0 | 0 | 0 | 70 | 0 | 0 | 0 | 40 |

| | Compounds | | | | | | | | | | | | |
|---|---|---|---|---|---|---|---|---|---|---|---|---|---|
| 125 g ai/ha | 34 | 35 | 36 | 37 | 38 | 39 | 40 | 41 | 42 | 43 | 44 | 45 | 46 | 47 |
| | Preemergence | | | | | | | | | | | | |
| Barnyardgrass | 0 | 70 | 0 | 30 | 90 | 0 | 0 | 0 | 0 | 40 | 0 | 0 | 20 | 0 |
| Foxtail, Giant | 70 | 100 | 0 | 70 | 100 | 0 | 20 | 0 | 0 | 60 | 40 | 10 | 100 | 0 |
| Kochia | 20 | 30 | 0 | 0 | 40 | 0 | 60 | 30 | 0 | 100 | 0 | 0 | 70 | 0 |
| Pigweed | 40 | 100 | 0 | 0 | 100 | 0 | 40 | 30 | 0 | 90 | 0 | 70 | 100 | 0 |

TABLE A-continued

| | | | | | | | | | | | | | | |
|---|---|---|---|---|---|---|---|---|---|---|---|---|---|---|
| Ragweed | 0 | 0 | 0 | 0 | 0 | 0 | 0 | 50 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |

| Compounds | | | | | | | | | | | | | | |
|---|---|---|---|---|---|---|---|---|---|---|---|---|---|---|
| 125 g ai/ha | 48 | 49 | 50 | 51 | 53 | 54 | 61 | 62 | 63 | 64 | 65 | 66 | 67 | 68 |

Preemergence

| | | | | | | | | | | | | | | |
|---|---|---|---|---|---|---|---|---|---|---|---|---|---|---|
| Barnyardgrass | 0 | 0 | 10 | 0 | 0 | 0 | 50 | 70 | 100 | 0 | 30 | 100 | 0 | 70 |
| Foxtail, Giant | 0 | 0 | 100 | 0 | 0 | 0 | 100 | 100 | 90 | 0 | 100 | 100 | 0 | 80 |
| Kochia | 0 | 0 | 0 | 0 | 0 | 0 | 90 | 70 | 0 | 0 | 60 | 40 | 0 | 30 |
| Pigweed | 0 | 0 | 90 | 0 | 0 | 0 | 100 | 90 | 90 | 0 | 100 | 100 | 0 | 80 |
| Ragweed | 0 | 0 | 0 | 0 | 0 | 0 | 0 | 0 | 0 | 0 | 0 | 100 | 0 | 0 |
| Ryegrass, Italian | 0 | 0 | 0 | 0 | 0 | 0 | 30 | 10 | 0 | 0 | 10 | 30 | 0 | 0 |

| Compounds | | | | | | | | | | | | | | |
|---|---|---|---|---|---|---|---|---|---|---|---|---|---|---|
| 125 g ai/ha | 69 | 70 | 71 | 72 | 73 | 74 | 75 | 76 | 77 | 78 | 79 | 80 | 81 | 82 |

Preemergence

| | | | | | | | | | | | | | | |
|---|---|---|---|---|---|---|---|---|---|---|---|---|---|---|
| Barnyardgrass | 90 | 20 | 10 | 90 | 100 | 60 | 100 | 70 | 100 | 60 | 100 | 100 | 90 | 100 |
| Foxtail, Giant | 70 | 60 | 100 | 90 | 100 | 100 | 100 | 70 | 100 | 90 | 100 | 100 | 100 | 100 |
| Kochia | 30 | 0 | 0 | 90 | 100 | 100 | 80 | 0 | 100 | 20 | 80 | 100 | 90 | 80 |
| Pigweed | 100 | 0 | 40 | 100 | 100 | 90 | 100 | 50 | 100 | 80 | 100 | 100 | 100 | 100 |
| Ragweed | 0 | 0 | 0 | 0 | 10 | 0 | 0 | 0 | 0 | 0 | 30 | 20 | 0 | 60 |
| Ryegrass, Italian | 0 | 0 | 0 | 10 | 50 | 20 | 80 | 0 | 70 | 0 | 90 | 50 | 20 | 80 |

| Compounds | | | | | | | | | | | | | | |
|---|---|---|---|---|---|---|---|---|---|---|---|---|---|---|
| 125 g ai/ha | 83 | 84 | 85 | 86 | 87 | 88 | 89 | 90 | 91 | 92 | 93 | 94 | 95 | 96 |

Preemergence

| | | | | | | | | | | | | | | |
|---|---|---|---|---|---|---|---|---|---|---|---|---|---|---|
| Barnyardgrass | 30 | 0 | 0 | 90 | 100 | 0 | 90 | 40 | 90 | 100 | 0 | 0 | 70 | 0 |
| Foxtail, Giant | 90 | 0 | 0 | 50 | 100 | 0 | 50 | 70 | 70 | 100 | 0 | 0 | 50 | 0 |
| Kochia | 0 | 0 | 0 | 100 | 90 | 0 | 50 | 0 | 20 | 90 | 0 | 0 | 0 | 0 |
| Pigweed | 30 | 0 | 0 | 100 | 100 | 0 | 100 | 0 | 40 | 100 | 0 | 0 | 40 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 20 | 20 | 0 | 20 | 0 | 0 | 80 | 0 | 0 | 0 | 0 |

| Compounds | | | | | | | | | | | | | | |
|---|---|---|---|---|---|---|---|---|---|---|---|---|---|---|
| 125 g ai/ha | 97 | 98 | 99 | 100 | 101 | 102 | 103 | 104 | 105 | 106 | 107 | 108 | 109 | 110 |

Preemergence

| | | | | | | | | | | | | | | |
|---|---|---|---|---|---|---|---|---|---|---|---|---|---|---|
| Barnyardgrass | 10 | 30 | 100 | 100 | 10 | 0 | 50 | 30 | 30 | 0 | 100 | 30 | 20 | 100 |
| Foxtail, Giant | 70 | 40 | 100 | 100 | 40 | 0 | 60 | 40 | 20 | 80 | 100 | 80 | 40 | 100 |
| Kochia | 0 | 0 | 80 | 0 | 0 | 0 | 70 | 0 | 0 | 30 | 100 | 10 | 0 | 100 |
| Pigweed | 20 | 0 | 90 | 60 | 0 | 0 | 100 | 40 | 20 | 30 | 100 | 70 | 60 | 100 |
| Ragweed | 0 | 0 | 10 | 0 | 0 | 0 | 0 | 0 | 0 | 0 | 20 | 0 | 0 | 0 |
| Ryegrass, Italian | 0 | 0 | 30 | 0 | 0 | 0 | 0 | 0 | 0 | 0 | 80 | 0 | 0 | 70 |

| Compounds | | | | | | | | | | | | | | |
|---|---|---|---|---|---|---|---|---|---|---|---|---|---|---|
| 125 g ai/ha | 111 | 112 | 113 | 114 | 115 | 116 | 117 | 118 | 119 | 120 | 121 | 122 | 123 | 124 |

Preemergence

| | | | | | | | | | | | | | | |
|---|---|---|---|---|---|---|---|---|---|---|---|---|---|---|
| Barnyardgrass | 0 | 80 | 90 | 20 | 0 | 0 | 0 | 0 | 20 | 0 | 30 | 90 | 70 | 80 |
| Foxtail, Giant | 0 | 70 | 100 | 90 | 0 | 30 | 20 | 20 | 90 | 0 | 100 | 40 | 100 | 100 |
| Kochia | 0 | 50 | 60 | 10 | 0 | 0 | 0 | 0 | 0 | 0 | 0 | 70 | 10 | 10 |
| Pigweed | 0 | 100 | 100 | 30 | 0 | 70 | 30 | 50 | 100 | 0 | 0 | 90 | 80 | 100 |
| Ragweed | 0 | 0 | 0 | 80 | 0 | 0 | 0 | 50 | 0 | 0 | 0 | 0 | 0 | 0 |
| Ryegrass, Italian | 0 | 0 | 40 | 0 | 0 | 0 | 0 | 0 | 0 | 0 | 0 | 30 | 20 | 20 |

| Compounds | | | | | | | | | | | | | | |
|---|---|---|---|---|---|---|---|---|---|---|---|---|---|---|
| 125 g ai/ha | 125 | 126 | 127 | 128 | 129 | 130 | 131 | 132 | 133 | 134 | 135 | 136 | 137 | 138 |

Preemergence

| | | | | | | | | | | | | | | |
|---|---|---|---|---|---|---|---|---|---|---|---|---|---|---|
| Barnyardgrass | 100 | 0 | 60 | 50 | 100 | 100 | 100 | 100 | 30 | 80 | 40 | 100 | 90 | 100 |
| Foxtail, Giant | 100 | 0 | 100 | 100 | 100 | 100 | 90 | 100 | 90 | 90 | 50 | 100 | 100 | 100 |
| Kochia | 100 | 0 | 30 | 0 | 100 | 100 | 100 | 60 | 10 | 10 | 0 | 100 | 70 | 100 |

TABLE A-continued

| | | | | | | | | | | | | | | |
|---|---|---|---|---|---|---|---|---|---|---|---|---|---|---|
| Pigweed | 100 | 0 | 70 | 30 | 100 | 100 | 100 | 100 | 100 | 50 | 20 | 100 | 100 | 100 |
| Ragweed | 20 | 0 | 0 | 0 | 0 | 20 | 0 | 0 | 0 | 0 | 0 | 0 | 80 | 0 | 0 |
| Ryegrass, Italian | 70 | 0 | 10 | 10 | 60 | 80 | 20 | 30 | 0 | 20 | 10 | 20 | 20 | 100 |

| | Compounds | | | | | | | | Compounds | |
|---|---|---|---|---|---|---|---|---|---|---|
| 125 g ai/ha | 139 | 140 | 141 | 142 | 143 | 144 | 145 | 146 | 31 g ai/ha | 145 | 146 |

Preemergence

| | | | | | | | | | | | |
|---|---|---|---|---|---|---|---|---|---|---|---|
| Barnyardgrass | 0 | 0 | 60 | 0 | 100 | 100 | 80 | 100 | Barnyardgrass | 40 | 20 |
| Foxtail, Giant | 0 | 0 | 100 | 0 | 100 | 100 | 100 | 100 | Foxtail, Giant | 90 | 80 |
| Kochia | 0 | 40 | 20 | 0 | 100 | 100 | 40 | 80 | Kochia | 0 | 60 |
| Pigweed | 0 | 10 | 90 | 0 | — | 100 | 100 | 100 | Pigweed | 100 | 60 |
| Ragweed | 50 | 0 | 30 | 0 | 0 | 10 | 30 | 0 | Ragweed | 0 | 0 |
| Ryegrass, Italian | 0 | 10 | 10 | 0 | 70 | 70 | 50 | 50 | Ryegrass, Italian | 10 | 0 |

| | Compounds | | | | | | | | | | | | |
|---|---|---|---|---|---|---|---|---|---|---|---|---|---|
| 31 g ai/ha | 1 | 2 | 3 | 4 | 5 | 19 | 36 | 37 | 38 | 43 | 44 | 45 | 46 | 50 |

Preemergence

| | | | | | | | | | | | | | |
|---|---|---|---|---|---|---|---|---|---|---|---|---|---|
| Barnyardgrass | 20 | 10 | 60 | 0 | 0 | 0 | 0 | 0 | 20 | 0 | 0 | 0 | 0 | 0 |
| Foxtail, Giant | 30 | 70 | 70 | 0 | 0 | 0 | 0 | 20 | 30 | 0 | 0 | 0 | 40 | 50 |
| Kochia | 0 | 30 | 0 | 0 | 0 | 0 | 0 | 0 | 0 | 100 | 0 | 0 | 0 | 0 |
| Pigweed | 20 | 40 | 50 | 0 | 0 | 0 | 0 | 0 | 60 | 30 | 0 | 0 | 50 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 31 g ai/ha | 51 | 53 | 54 | 62 | 63 | 66 | 67 | 68 | 69 | 70 | 71 | 74 | 76 | 77 |

Preemergence

| | | | | | | | | | | | | | |
|---|---|---|---|---|---|---|---|---|---|---|---|---|---|
| Barnyardgrass | 0 | 0 | 0 | 30 | 40 | 90 | 0 | 10 | 70 | 0 | 0 | 10 | 0 | 20 |
| Foxtail, Giant | 0 | 0 | 0 | 30 | 10 | 70 | 0 | 10 | 40 | 0 | 40 | 40 | 0 | 100 |
| Kochia | 0 | 0 | 0 | 20 | 0 | 0 | 0 | 0 | 0 | 0 | 0 | 0 | 0 | 80 |
| Pigweed | 0 | 0 | 0 | 60 | 0 | 20 | 0 | 20 | 40 | 0 | 0 | 20 | 0 | 100 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 31 g ai/ha | 80 | 81 | 82 | 86 | 87 | 88 | 89 | 90 | 92 | 93 | 94 | 95 | 96 | 97 |

Preemergence

| | | | | | | | | | | | | | |
|---|---|---|---|---|---|---|---|---|---|---|---|---|---|
| Barnyardgrass | 60 | 10 | 50 | 0 | 70 | 0 | 20 | 0 | 70 | 0 | 0 | 10 | 0 | 0 |
| Foxtail, Giant | 90 | 30 | 90 | 0 | 60 | 0 | 10 | 10 | 100 | 0 | 0 | 0 | 0 | 40 |
| Kochia | 100 | 0 | 70 | 10 | 30 | 0 | 10 | 0 | 90 | 0 | 0 | 0 | 0 | 0 |
| Pigweed | 100 | 100 | 90 | 20 | 40 | 0 | 10 | 0 | 100 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 30 | 0 | 0 | 0 | 0 | 0 |

| | Compounds | | | | | | | | | | | | |
|---|---|---|---|---|---|---|---|---|---|---|---|---|---|
| 31 g ai/ha | 98 | 99 | 100 | 101 | 102 | 103 | 104 | 105 | 107 | 108 | 109 | 110 | 111 | 112 |

Preemergence

| | | | | | | | | | | | | | |
|---|---|---|---|---|---|---|---|---|---|---|---|---|---|
| Barnyardgrass | 0 | 70 | 40 | 0 | 0 | 0 | 0 | 0 | 90 | 10 | 0 | 40 | 0 | 0 |
| Foxtail, Giant | 0 | 90 | 50 | 0 | 0 | 10 | 0 | 0 | 100 | 10 | 0 | 80 | 0 | 0 |
| Kochia | 0 | 40 | 0 | 0 | 0 | 0 | 0 | 0 | 90 | 0 | 0 | 10 | 0 | 0 |
| Pigweed | 0 | 50 | 0 | 0 | 0 | 40 | 0 | 0 | 100 | 0 | 0 | 40 | 0 | 60 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 30 | 0 | 0 | 0 | 0 | 10 |

| | Compounds | | | | | | | | | | | | |
|---|---|---|---|---|---|---|---|---|---|---|---|---|---|
| 31 g ai/ha | 113 | 114 | 115 | 116 | 117 | 118 | 119 | 120 | 121 | 122 | 123 | 124 | 126 | 127 |

Preemergence

| | | | | | | | | | | | | | |
|---|---|---|---|---|---|---|---|---|---|---|---|---|---|
| Barnyardgrass | 0 | 0 | 0 | 0 | 0 | 0 | 0 | 0 | 0 | 30 | 20 | 10 | 0 | 20 |
| Foxtail, Giant | 60 | 10 | 0 | 0 | 0 | 0 | 50 | 0 | 30 | 0 | 40 | 60 | 0 | 30 |
| Kochia | 10 | 0 | 70 | 0 | 0 | 0 | 0 | 0 | 20 | 10 | 0 | 0 | 0 | 0 |

TABLE A-continued

| | | | | | | | | | | | | | | |
|---|---|---|---|---|---|---|---|---|---|---|---|---|---|---|
| Pigweed | 100 | 0 | 0 | 50 | 0 | 20 | 20 | 0 | 0 | 40 | 0 | 40 | 0 | 0 |
| Ragweed | 0 | 20 | 20 | 30 | 0 | 100 | 0 | 0 | 0 | 0 | 0 | 0 | 0 | 0 |
| Ryegrass, Italian | 10 | 0 | 0 | 0 | 0 | 0 | 0 | 0 | 10 | 0 | 0 | 0 | 0 | 0 |

| | Compounds | | | | | | | | | | | | | |
|---|---|---|---|---|---|---|---|---|---|---|---|---|---|---|
| 31 g ai/ha | 128 | 129 | 131 | 132 | 133 | 134 | 135 | 137 | 138 | 140 | 141 | 142 | 143 | 144 |
| | Preemergence | | | | | | | | | | | | | |
| Barnyardgrass | 20 | 70 | 0 | 30 | 0 | 0 | 0 | 0 | 70 | 0 | 0 | 0 | 20 | 80 |
| Foxtail, Giant | 30 | 100 | 0 | 40 | 0 | 10 | 0 | 70 | 90 | 0 | 10 | 0 | 100 | 100 |
| Kochia | 0 | 30 | 10 | 10 | 0 | 0 | 0 | 0 | 50 | 0 | 10 | 0 | 100 | 90 |
| Pigweed | 0 | 90 | 90 | 70 | 70 | 0 | 0 | 10 | 80 | 0 | 0 | 0 | — | 100 |
| Ragweed | 0 | 0 | 0 | 0 | 0 | 0 | 0 | 0 | 0 | 0 | 0 | 0 | 0 | 0 |
| Ryegrass, Italian | 0 | 20 | 0 | 0 | 0 | 0 | 0 | 0 | 10 | 10 | 0 | 0 | 20 | 20 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

| | Compounds | | | | | | | | | | | | | |
|---|---|---|---|---|---|---|---|---|---|---|---|---|---|---|
| 250 g ai/ha | 1 | 2 | 3 | 4 | 5 | 6 | 7 | 8 | 9 | 10 | 11 | 12 | 13 | 18 |
| | Flood | | | | | | | | | | | | | |
| Barnyardgrass | 0 | 0 | 0 | 0 | 0 | 0 | 0 | 0 | 20 | 0 | 0 | 0 | 0 | 0 |
| Ducksalad | 20 | 30 | 30 | 0 | 0 | 0 | 0 | 0 | 75 | 80 | 0 | 0 | 70 | 0 |
| Rice | 0 | 0 | 0 | 0 | 0 | 0 | 0 | 0 | 0 | 0 | 0 | 0 | 30 | 0 |
| Sedge, Umbrella | 80 | 100 | 100 | 0 | 0 | 0 | 0 | 70 | 75 | 80 | 0 | 0 | 75 | 0 |

| | Compounds | | | | | | | | | | | | | |
|---|---|---|---|---|---|---|---|---|---|---|---|---|---|---|
| 250 g ai/ha | 19 | 20 | 21 | 22 | 23 | 24 | 25 | 26 | 30 | 33 | 35 | 36 | 37 | 38 |
| | Flood | | | | | | | | | | | | | |
| Barnyardgrass | 0 | 0 | 30 | 0 | 0 | 0 | 0 | 60 | 0 | 0 | 0 | 0 | 0 | 0 |
| Ducksalad | 0 | 30 | 70 | 40 | 30 | 0 | 0 | 100 | 40 | 80 | 50 | 0 | 0 | 40 |
| Rice | 0 | 0 | 0 | 0 | 15 | 0 | 0 | 20 | 0 | 0 | 0 | 0 | 0 | 0 |
| Sedge, Umbrella | 0 | 40 | 100 | 50 | 95 | 0 | 0 | 100 | 0 | 95 | 60 | 0 | 0 | 30 |

| | Compounds | | | | | | | | | | | | | |
|---|---|---|---|---|---|---|---|---|---|---|---|---|---|---|
| 250 g ai/ha | 43 | 44 | 45 | 46 | 47 | 48 | 49 | 50 | 51 | 53 | 54 | 56 | 57 | 58 |
| | Flood | | | | | | | | | | | | | |
| Barnyardgrass | 0 | 0 | 0 | 0 | 0 | 20 | 20 | 0 | 15 | 0 | 0 | 0 | 0 | 0 |
| Ducksalad | 0 | 0 | 0 | 75 | 0 | 0 | 0 | 65 | 0 | 0 | 0 | 0 | 0 | 0 |
| Rice | 0 | 0 | 0 | 10 | 0 | 20 | 20 | 0 | 15 | 0 | 0 | 0 | 0 | 0 |
| Sedge, Umbrella | 0 | 30 | 0 | 80 | 0 | 0 | 0 | 80 | 0 | 0 | 0 | 0 | 0 | 0 |

| | Compounds | | | | | | | | | | | | | |
|---|---|---|---|---|---|---|---|---|---|---|---|---|---|---|
| 250 g ai/ha | 61 | 62 | 63 | 64 | 65 | 66 | 67 | 68 | 69 | 70 | 71 | 74 | 75 | 76 |
| | Flood | | | | | | | | | | | | | |
| Barnyardgrass | 20 | 40 | 45 | 0 | 0 | 30 | 0 | 0 | 0 | 0 | 0 | 40 | 40 | 0 |
| Ducksalad | 100 | 100 | 100 | 0 | 70 | 100 | 0 | 0 | 75 | 70 | 90 | 100 | 95 | 85 |
| Rice | 0 | 0 | 25 | 0 | 0 | 0 | 0 | 0 | 20 | 0 | 0 | 0 | 35 | 10 |
| Sedge, Umbrella | 100 | 90 | 100 | 0 | 85 | 95 | 0 | 0 | 80 | 80 | 95 | 100 | 95 | 70 |

TABLE B-continued

| 250 g ai/ha | 77 | 78 | 79 | 80 | 81 | 82 | 83 | 84 | 85 | 86 | 87 | 88 | 89 | 90 |
|---|---|---|---|---|---|---|---|---|---|---|---|---|---|---|
| Flood | | | | | | | | | | | | | | |
| Barnyardgrass | 15 | 20 | 60 | 75 | 45 | 35 | 0 | 0 | 0 | 40 | 50 | 0 | 40 | 0 |
| Ducksalad | 85 | 70 | 90 | 100 | 100 | 100 | 80 | 0 | 0 | 100 | 100 | 0 | 95 | 30 |
| Rice | 0 | 15 | 45 | 55 | 0 | 30 | 0 | 0 | 0 | 20 | 35 | 20 | 40 | 0 |
| Sedge, Umbrella | 100 | 80 | 100 | 100 | 100 | 95 | 80 | 0 | 0 | 100 | 100 | 0 | 95 | 60 |

| 250 g ai/ha | 91 | 92 | 93 | 94 | 95 | 96 | 97 | 98 | 99 | 100 | 101 | 102 | 103 | 104 |
|---|---|---|---|---|---|---|---|---|---|---|---|---|---|---|
| Flood | | | | | | | | | | | | | | |
| Barnyardgrass | 0 | 25 | 0 | 0 | 0 | 0 | 0 | 0 | 60 | 40 | 0 | 0 | 0 | 0 |
| Ducksalad | 100 | 100 | 0 | 0 | 30 | 0 | 70 | 0 | 100 | 90 | 0 | 80 | 95 | 75 |
| Rice | 20 | 0 | 0 | 0 | 0 | 0 | 0 | 0 | 40 | 0 | 0 | 0 | 20 | 0 |
| Sedge, Umbrella | 95 | 100 | 0 | 0 | 0 | 0 | 75 | 0 | 90 | 70 | 0 | 80 | 95 | 75 |

| 250 g ai/ha | 105 | 106 | 107 | 108 | 109 | 110 | 111 | 112 | 113 | 114 | 115 | 116 | 117 | 118 |
|---|---|---|---|---|---|---|---|---|---|---|---|---|---|---|
| Flood | | | | | | | | | | | | | | |
| Barnyardgrass | 0 | 0 | 50 | 0 | 0 | 25 | 0 | 20 | 65 | 0 | 0 | 30 | 0 | 0 |
| Ducksalad | 40 | 0 | 95 | 80 | 0 | 75 | 0 | 100 | 80 | 40 | 0 | 75 | 20 | 0 |
| Rice | 0 | 0 | 35 | 0 | 0 | 25 | 0 | 40 | 20 | 0 | 0 | 70 | 0 | 0 |
| Sedge, Umbrella | 0 | 0 | 95 | 60 | 0 | 90 | 0 | 100 | 90 | 90 | 0 | 90 | 60 | 50 |

| 250 g ai/ha | 119 | 120 | 121 | 122 | 123 | 124 | 125 | 126 | 127 | 128 | 129 | 130 | 131 | 132 |
|---|---|---|---|---|---|---|---|---|---|---|---|---|---|---|
| Flood | | | | | | | | | | | | | | |
| Barnyardgrass | 0 | 0 | 50 | 80 | 40 | 45 | 45 | 90 | 40 | 20 | 45 | 55 | 15 | 45 |
| Ducksalad | 100 | 0 | 0 | 100 | 95 | 100 | 70 | 0 | 90 | 90 | 90 | 40 | 80 | 90 |
| Rice | 0 | 0 | 35 | 40 | 35 | 40 | 35 | 0 | 15 | 15 | 40 | 35 | 15 | 45 |
| Sedge, Umbrella | 90 | 0 | 70 | 100 | 95 | 100 | 90 | 0 | 90 | 85 | 80 | 98 | 90 | 80 |

| 250 g ai/ha | 133 | 134 | 135 | 136 | 137 | 138 | 139 | 140 | 141 | 142 | 143 | 144 | 145 | 146 |
|---|---|---|---|---|---|---|---|---|---|---|---|---|---|---|
| Flood | | | | | | | | | | | | | | |
| Barnyardgrass | 0 | 0 | 0 | 45 | 75 | 50 | 0 | 0 | 20 | 0 | 50 | 70 | 50 | 40 |
| Ducksalad | 0 | 95 | 85 | 60 | 95 | 100 | 30 | 0 | 70 | 0 | 90 | 100 | 100 | 100 |
| Rice | 30 | 20 | 20 | 35 | 50 | 45 | 0 | 0 | 10 | 0 | 40 | 35 | 30 | 35 |
| Sedge, Umbrella | 0 | 95 | 85 | 80 | 95 | 85 | 0 | 0 | 50 | 0 | 90 | 100 | 100 | 85 |

Test C

Seeds of plant species selected from blackgrass (*Alopecurus myosuroides*), ryegrass, Italian (Italian ryegrass, *Lolium multiflorum*), wheat (winter wheat, *Triticum aestivum*), galium (catchweed bedstraw, *Galium aparine*), corn (*Zea mays*), crabgrass, large (large crabgrass, *Digitaria sanguinalis*), foxtail, giant (giant foxtail, *Setaria faberii*), johnsongrass (*Sorghum halepense*), lambsquarters (*Chenopodium album*), morningglory (*Ipomoea coccinea*), nutsedge, yellow (yellow nutsedge, *Cyperus esculentus*), pigweed (*Amaranthus retroflexus*), ragweed (common ragweed, *Ambrosia elatior*), soybean (*Glycine max*), barnyardgrass (*Echinochloa crus-galli*), oilseed rape (*Brassica napus*), pigweed, palmer (palmer pigweed, *Amaranthus palmeri*), waterhemp (common waterhemp, *Amaranthus rudis*), velvetleaf (*Abutilon theophrasti*), kochia (*Kochia scoparia*), surinam grass (*Brachiaria decumbens*), nightshade (eastern black nightshade, *Solanum ptycanthum*), wild poinsettia (*Euphorbia heterophylla*), windgrass (*Apera spica-venti*), and oat, wild (wild oat *Avena fatua*), were planted into a blend of loam soil and sand or a silt loam soil and treated preemergence with test chemicals formulated in a non-phytotoxic solvent mixture which included a surfactant.

At the same time, plants selected from these crop and weed species and also chickweed (common chickweed, *Stellaria media*), buckwheat, wild (wild buckwheat, *Polygonum convolvulus*), wild mustard (*Sinapis arvensis*), field poppy (*Papaver rhoeas*), field violet (*Viola arvensis*), geranium, cutleaf (cutleaf *geranium, Geranium dissectum*), Canada thistle (*Cirsium arvense*), and speedwell (bird's-eye speedwell, *Veronica persica*), were planted in pots containing Sunshine Redi-Earth® planting medium comprising spaghnum peat moss, vermiculite, starter nutrients and dolomitic limestone and treated with postemergence applications of test chemicals formulated in the same manner. Plants ranged in height from 2 to 18 cm (1- to 4-leaf stage) for postemergence treatments. Treated plants and controls were maintained in a greenhouse for 13 to 15 d, after which time all species were compared to controls and visually evaluated. Plant response ratings, summarized in Table C, are based on a scale of 0 to 100 where 0 is no effect and 100 is complete control. A dash (-) response means no test result.

Plant species in the flooded paddy test consisted of rice (*Oryza sativa*), sedge, umbrella (small-flower umbrella sedge *Cyperus difformis*), ducksalad (*Heteranthera limosa*), and barnyardgrass (*Echinochloa crus-galli*) grown to the 2-leaf stage for testing. At time of treatment, test pots were flooded to 3 cm above the soil surface, treated by application of test compounds directly to the paddy water, and then maintained at that water depth for the duration of the test.

TABLE C

| 125 g ai/ha | Compounds | | | | | | | | | | | | | |
|---|---|---|---|---|---|---|---|---|---|---|---|---|---|---|
| | 7 | 15 | 16 | 20 | 21 | 22 | 23 | 26 | 33 | 35 | 72 | 73 | 75 | 77 |
| Postemergence | | | | | | | | | | | | | | |
| Barnyardgrass | 10 | 20 | 20 | 20 | 20 | 10 | 20 | 30 | 25 | 15 | 10 | 30 | — | 30 |
| Blackgrass | 5 | 10 | 5 | 10 | 5 | 5 | 20 | 35 | 20 | 10 | 30 | 35 | 30 | 25 |
| Buckwheat, Wild | — | — | — | — | — | — | — | — | — | — | — | — | 85 | — |
| Canada Thistle | — | — | — | — | — | — | — | — | — | — | — | — | 100 | — |
| Chickweed | 50 | 90 | 80 | 75 | 80 | 60 | 85 | 98 | 85 | 50 | 98 | 85 | 98 | 100 |
| Corn | 15 | 20 | 20 | 20 | 20 | 15 | 10 | 25 | 30 | 20 | 20 | 15 | 20 | 25 |
| Crabgrass, Large | 15 | 25 | 25 | 15 | 35 | 25 | 25 | 65 | 15 | 10 | 50 | 60 | 25 | 30 |
| Field Poppy | — | — | — | — | — | — | — | — | — | — | — | — | 100 | — |
| Field Violet | — | — | — | — | — | — | — | — | — | — | — | — | 100 | — |
| Foxtail, Giant | 15 | 35 | 35 | 25 | 15 | 25 | 30 | 25 | 20 | 20 | 20 | 25 | 25 | 70 |
| Galium | 40 | 95 | 55 | 98 | 80 | 70 | 80 | 95 | 85 | 60 | 98 | 98 | 80 | 98 |
| Geranium, Cutleaf | — | — | — | — | — | — | — | — | — | — | — | — | 65 | — |
| Johnsongrass | — | — | — | — | — | 20 | 25 | 20 | 10 | 10 | 20 | 70 | — | — |
| Kochia | 20 | 95 | 90 | 100 | 90 | 50 | 85 | 95 | 95 | 90 | 100 | 100 | 98 | 100 |
| Lambsquarters | 55 | 95 | 60 | 85 | 85 | 75 | 80 | 98 | 90 | 70 | 85 | 98 | 90 | 90 |
| Morningglory | 55 | 90 | 75 | 70 | 70 | 50 | 35 | 85 | 65 | 60 | 70 | 75 | 65 | 80 |
| Mustard, Wild | — | — | — | — | — | — | — | — | — | — | — | — | — | — |
| Nightshade | — | — | — | — | — | — | — | — | — | — | — | — | 98 | — |
| Nutsedge, Yellow | 5 | 20 | 20 | 10 | 10 | 5 | 10 | 10 | 10 | 5 | 15 | 30 | 5 | 15 |
| Oat, Wild | 5 | 10 | 10 | 5 | 5 | 5 | 5 | 35 | 30 | 0 | 10 | 10 | 35 | 15 |
| Oilseed Rape | 5 | 0 | 70 | 60 | 30 | 80 | 35 | 80 | 95 | 65 | 65 | 50 | 95 | 85 |
| Pigweed | 70 | 98 | 50 | 95 | 90 | 95 | 85 | 100 | 100 | 98 | 100 | 100 | — | 100 |
| Pigweed, Palmer | — | — | — | — | — | — | — | — | — | — | — | — | 85 | — |
| Poinsettia, Wild | — | — | — | — | — | — | — | — | — | — | — | — | 80 | — |
| Ragweed | 25 | 65 | 40 | 60 | 55 | 50 | 50 | 90 | 60 | 20 | 75 | 65 | 60 | 70 |
| Ryegrass, Italian | 30 | 5 | 5 | 5 | 15 | 5 | 5 | 10 | 30 | 5 | 15 | 20 | 5 | 10 |
| Soybean | 70 | 90 | 50 | 60 | 60 | 75 | 35 | 75 | 55 | 35 | 70 | 60 | 85 | 65 |
| Speedwell | — | — | — | — | — | — | — | — | — | — | — | — | 100 | — |
| Surinam Grass | — | — | — | — | — | — | — | — | — | — | — | — | 20 | — |
| Velvetleaf | 40 | 85 | 50 | 70 | 70 | 85 | 40 | 80 | 75 | 40 | 70 | 75 | 75 | 65 |
| Waterhemp | 65 | — | — | 98 | 85 | 80 | 95 | 100 | 100 | 95 | 90 | 100 | 95 | 100 |
| Wheat | 5 | 0 | 0 | 5 | 0 | 0 | 0 | 10 | 5 | 0 | 5 | 5 | 10 | 30 |
| Windgrass | — | — | — | — | — | — | — | — | — | — | — | — | 5 | — |

| 125 g ai/ha | Compounds | | | | | | | | | | | | | |
|---|---|---|---|---|---|---|---|---|---|---|---|---|---|---|
| | 79 | 80 | 82 | 89 | 92 | 107 | 110 | 125 | 130 | 136 | 137 | 138 | 143 | 144 |
| Postemergence | | | | | | | | | | | | | | |
| Barnyardgrass | — | — | 60 | — | 20 | — | 30 | 10 | 20 | 10 | 40 | — | 20 | 10 |
| Blackgrass | 30 | 25 | 45 | 45 | 20 | 60 | 25 | 30 | 30 | 15 | 40 | 65 | 40 | 15 |
| Buckwheat, Wild | 90 | 95 | 100 | 85 | — | 100 | 80 | 98 | 80 | 80 | 90 | 100 | 100 | 95 |
| Canada Thistle | 100 | 85 | 98 | 85 | — | 90 | 95 | 90 | 98 | 85 | 100 | 95 | 100 | 90 |
| Chickweed | 98 | 90 | 90 | 100 | 100 | 100 | 90 | 98 | 90 | 80 | 100 | 100 | 100 | 85 |
| Corn | 20 | 25 | 25 | 20 | 20 | 30 | 15 | 20 | 20 | 20 | 25 | 30 | 30 | 25 |
| Crabgrass, Large | 65 | 30 | 20 | 90 | 35 | 60 | 60 | 20 | 20 | 30 | 70 | 95 | 30 | 25 |
| Field Poppy | 100 | 85 | 100 | 100 | — | 100 | 100 | 100 | 100 | 90 | 100 | 100 | 100 | 100 |
| Field Violet | 90 | 95 | 90 | 100 | — | 100 | 100 | 98 | 100 | 100 | 85 | 100 | 100 | 90 |
| Foxtail, Giant | 40 | 15 | 20 | 20 | 50 | 25 | 25 | 25 | 30 | 25 | 35 | 65 | 25 | 40 |
| Galium | 95 | 90 | 90 | 90 | 100 | 95 | 90 | 90 | 80 | 75 | 85 | 85 | 95 | 90 |
| Geranium, Cutleaf | 65 | 60 | 60 | 55 | — | 75 | 60 | 55 | 60 | 45 | 35 | 60 | 75 | 40 |
| Johnsongrass | 85 | 5 | 30 | 85 | — | 98 | 15 | 25 | 15 | 15 | 25 | 90 | 20 | 5 |
| Kochia | 98 | 80 | 95 | 95 | 100 | 98 | 100 | 98 | 98 | 90 | 98 | 98 | 100 | 90 |
| Lambsquarters | 100 | 85 | 90 | 100 | 85 | 100 | 98 | 100 | 95 | 80 | 90 | 100 | 95 | 85 |
| Morningglory | 30 | 60 | 75 | 55 | 85 | 95 | 50 | 75 | 55 | 35 | 20 | 65 | 65 | 60 |
| Mustard, Wild | — | 90 | 100 | — | — | 100 | 100 | 100 | 100 | 100 | 100 | 100 | 100 | 95 |
| Nightshade | 100 | 75 | 100 | 95 | — | 100 | 98 | 90 | 90 | 80 | 90 | 98 | 90 | 90 |
| Nutsedge, Yellow | 5 | 5 | 10 | 5 | 20 | 5 | 5 | 10 | 5 | 5 | 5 | 30 | 25 | 10 |
| Oat, Wild | 35 | 5 | 50 | 30 | 5 | 45 | 55 | 15 | 15 | 10 | 10 | 70 | 20 | 35 |
| Oilseed Rape | 100 | 70 | 95 | 100 | 70 | 98 | 95 | 95 | 98 | 80 | 100 | 100 | 100 | 85 |
| Pigweed | — | — | — | — | 100 | — | — | — | — | — | — | — | — | — |
| Pigweed, Palmer | 85 | 60 | 98 | 85 | — | 100 | 95 | 85 | 65 | 70 | 70 | 98 | 100 | 80 |
| Poinsettia, Wild | 85 | 75 | 75 | 90 | — | 90 | 90 | 85 | 75 | 75 | 75 | 90 | 75 | 60 |
| Ragweed | 65 | 35 | 55 | 25 | 70 | 45 | 60 | 55 | 50 | 35 | 30 | 75 | 55 | 15 |
| Ryegrass, Italian | 30 | 5 | 25 | 10 | 30 | 50 | 20 | 15 | 15 | 10 | 10 | 35 | 20 | 20 |

TABLE C-continued

| | | | | | | | | | | | | | | |
|---|---|---|---|---|---|---|---|---|---|---|---|---|---|---|
| Soybean | 65 | 95 | 40 | 70 | 75 | 95 | 35 | 70 | 95 | 40 | 40 | 55 | 65 | 65 |
| Speedwell | 100 | 100 | 95 | 100 | — | 100 | 95 | 98 | 98 | 85 | 100 | 100 | 100 | 95 |
| Surinam Grass | 35 | 25 | 25 | 20 | — | 35 | 25 | 20 | 20 | 10 | 20 | 35 | 20 | 25 |
| Velvetleaf | 90 | 55 | 75 | 70 | 85 | 90 | 75 | 30 | 75 | 70 | 70 | 75 | 70 | 65 |
| Waterhemp | 98 | 90 | 95 | 95 | 100 | 100 | 95 | 90 | 85 | 75 | 75 | 100 | 90 | 75 |
| Wheat | 15 | 15 | 30 | 15 | 10 | 30 | 15 | 25 | 30 | 5 | 20 | 35 | 30 | 15 |
| Windgrass | 30 | 30 | 35 | 35 | — | 50 | 30 | 35 | 35 | 30 | 45 | 50 | 40 | 30 |

| | Compounds | | | | | | | | | | | | | |
|---|---|---|---|---|---|---|---|---|---|---|---|---|---|---|
| 62 g ai/ha | 7 | 15 | 16 | 20 | 21 | 22 | 23 | 26 | 33 | 35 | 72 | 73 | 75 | 77 |

| | Postemergence | | | | | | | | | | | | | |
|---|---|---|---|---|---|---|---|---|---|---|---|---|---|---|
| Barnyardgrass | 15 | 20 | 20 | 10 | 20 | 10 | 10 | 20 | 10 | 10 | 10 | 20 | — | 25 |
| Blackgrass | 0 | 10 | 0 | 5 | 5 | 0 | 15 | 15 | 10 | 10 | 10 | 40 | 10 | 20 |
| Buckwheat, Wild | — | — | — | — | — | — | — | — | — | — | — | — | 80 | — |
| Canada Thistle | — | — | — | — | — | — | — | — | — | — | — | — | 75 | — |
| Chickweed | 30 | 90 | 50 | 65 | 50 | 65 | 50 | 85 | 85 | 45 | 90 | 90 | 90 | 100 |
| Corn | 10 | 20 | 15 | 10 | 15 | 5 | 5 | 20 | 25 | 20 | 10 | 15 | 15 | 20 |
| Crabgrass, Large | 20 | 25 | 25 | 15 | 25 | 25 | 20 | 25 | 10 | 15 | 10 | 25 | 15 | 30 |
| Field Poppy | — | — | — | — | — | — | — | — | — | — | — | — | 80 | — |
| Field Violet | — | — | — | — | — | — | — | — | — | — | — | — | 98 | — |
| Foxtail, Giant | 10 | 20 | 30 | 10 | 20 | 15 | 25 | 10 | 10 | 10 | 20 | 20 | 10 | 25 |
| Galium | 10 | 95 | 55 | 80 | 75 | 60 | 55 | 95 | 80 | 55 | 5 | 75 | 70 | 95 |
| Geranium, Cutleaf | — | — | — | — | — | — | — | — | — | — | — | — | 35 | — |
| Johnsongrass | — | — | — | — | — | 15 | 20 | 20 | 10 | 10 | 20 | 10 | — | — |
| Kochia | 25 | 95 | 80 | 100 | 90 | 85 | 55 | 90 | 95 | 60 | 100 | 100 | 90 | 100 |
| Lambsquarters | 30 | 75 | 40 | 70 | 65 | 70 | 65 | 98 | 80 | 65 | 75 | 90 | 70 | 70 |
| Morningglory | 40 | 85 | 40 | 70 | 40 | 35 | 60 | 65 | 75 | 60 | 40 | 85 | 20 | 90 |
| Mustard, Wild | — | — | — | — | — | — | — | — | — | — | — | — | — | — |
| Nightshade | — | — | — | — | — | — | — | — | — | — | — | — | 85 | 15 |
| Nutsedge, Yellow | 5 | 5 | 10 | 5 | 5 | 5 | 5 | 10 | 5 | 0 | 10 | 20 | 0 | 15 |
| Oat, Wild | 5 | 5 | 5 | 5 | 5 | 0 | 10 | 15 | 25 | 0 | 5 | 5 | 40 | 10 |
| Oilseed Rape | 0 | 100 | 60 | 50 | 50 | 55 | 50 | 75 | 55 | 50 | 0 | 98 | 80 | 70 |
| Pigweed | 60 | 95 | 85 | 98 | 90 | 70 | 70 | 98 | 98 | 90 | 85 | 100 | — | 100 |
| Pigweed, Palmer | — | — | — | — | — | — | — | — | — | — | — | — | 95 | — |
| Poinsettia, Wild | — | — | — | — | — | — | — | — | — | — | — | — | 80 | — |
| Ragweed | 20 | 50 | 10 | 55 | 45 | 50 | 40 | 55 | 50 | 10 | 40 | 60 | 50 | 35 |
| Ryegrass, Italian | 30 | 10 | 0 | 10 | 0 | 0 | 5 | 10 | 5 | 5 | 10 | 10 | 10 | 10 |
| Soybean | 40 | 80 | 50 | 55 | 60 | 35 | 70 | 65 | 30 | 35 | 40 | 75 | 85 | 70 |
| Speedwell | — | — | — | — | — | — | — | — | — | — | — | — | 100 | — |
| Surinam Grass | — | — | — | — | — | — | — | — | — | — | — | — | 20 | — |
| Velvetleaf | 35 | 60 | 30 | 40 | 60 | 55 | 35 | 75 | 65 | 35 | 40 | 70 | 70 | 55 |
| Waterhemp | 60 | — | — | 90 | 90 | 85 | 85 | 98 | 100 | 90 | 90 | 100 | 90 | 100 |
| Wheat | 5 | 0 | 0 | 5 | 0 | 0 | 0 | 5 | 0 | 0 | 0 | 5 | 0 | 10 |
| Windgrass | — | — | — | — | — | — | — | — | — | — | — | — | 10 | — |

| | Compounds | | | | | | | | | | | | | |
|---|---|---|---|---|---|---|---|---|---|---|---|---|---|---|
| 62 g ai/ha | 79 | 80 | 82 | 89 | 92 | 107 | 110 | 125 | 130 | 136 | 137 | 138 | 143 | 144 |

| | Postemergence | | | | | | | | | | | | | |
|---|---|---|---|---|---|---|---|---|---|---|---|---|---|---|
| Barnyardgrass | — | — | 10 | — | 15 | — | 20 | 5 | 10 | 10 | 20 | — | 10 | 10 |
| Blackgrass | 20 | 5 | 40 | 30 | 5 | 20 | 20 | 15 | 20 | 10 | 15 | 10 | 15 | 15 |
| Buckwheat, Wild | 85 | 75 | 100 | 75 | — | 75 | 95 | 75 | 75 | 90 | 98 | 100 | 100 | 80 |
| Canada Thistle | 70 | 75 | 85 | 85 | — | 90 | 98 | 90 | 98 | 85 | 98 | 90 | 90 | 90 |
| Chickweed | 95 | 75 | 90 | 85 | 100 | 98 | 95 | 90 | 80 | 75 | 90 | 100 | 85 | 85 |
| Corn | 20 | 15 | 25 | 15 | 15 | 20 | 20 | 15 | 15 | 20 | 15 | 25 | 20 | 20 |
| Crabgrass, Large | 70 | 10 | 30 | 85 | 25 | 30 | 25 | 15 | 10 | 10 | 40 | 85 | 15 | 20 |
| Field Poppy | 100 | 85 | 100 | 100 | — | 98 | 100 | 100 | 100 | 80 | 100 | 100 | 90 | 90 |
| Field Violet | 85 | 90 | 90 | 100 | — | 98 | 95 | 98 | 95 | 95 | 85 | 100 | 98 | 80 |
| Foxtail, Giant | 25 | 10 | 10 | 10 | 25 | 20 | 25 | 10 | 10 | 10 | 40 | 30 | 10 | 30 |
| Galium | 85 | 85 | 85 | 80 | 100 | 90 | 75 | 80 | 85 | 60 | 75 | 80 | 80 | 85 |
| Geranium, Cutleaf | 55 | 35 | 40 | 50 | — | 60 | 40 | 55 | 45 | 50 | 30 | 55 | 60 | 35 |
| Johnsongrass | 60 | 5 | 10 | 10 | — | 35 | 10 | 10 | 10 | 10 | 10 | 80 | 10 | 5 |
| Kochia | 90 | 80 | 95 | 80 | 100 | 95 | 100 | 95 | 95 | 85 | 98 | 95 | 100 | 90 |
| Lambsquarters | 90 | 80 | 85 | 100 | 50 | 100 | 95 | 95 | 85 | 80 | 85 | 95 | 90 | 70 |
| Morningglory | 30 | 55 | 30 | 25 | 65 | 80 | 60 | 50 | 65 | 20 | 20 | 65 | 50 | 50 |
| Mustard, Wild | — | 80 | 100 | 100 | — | 95 | 100 | 98 | 100 | 85 | 100 | 100 | 100 | 80 |
| Nightshade | 95 | 70 | 95 | 95 | — | 98 | 95 | 85 | 85 | 70 | 90 | 100 | 90 | 75 |
| Nutsedge, Yellow | 5 | 5 | 20 | 0 | 10 | 5 | 5 | 5 | 5 | 0 | 10 | 10 | 5 | 10 |
| Oat, Wild | 45 | 10 | 40 | 40 | 5 | 35 | 45 | 15 | 15 | 10 | 10 | 50 | 10 | 30 |
| Oilseed Rape | 98 | 65 | 95 | 90 | 50 | 95 | 85 | 90 | 95 | 80 | 90 | 95 | 95 | 70 |
| Pigweed | — | — | — | — | 98 | — | — | — | — | — | — | — | — | — |
| Pigweed, Palmer | 70 | 70 | 98 | 80 | — | 100 | 98 | 80 | 45 | 70 | 50 | 90 | 80 | 40 |
| Poinsettia, Wild | 80 | 70 | 85 | 80 | — | 90 | 80 | 75 | 60 | 70 | 65 | 75 | 70 | 50 |
| Ragweed | 75 | 15 | 60 | 10 | 60 | 35 | 60 | 45 | 55 | 30 | 30 | 35 | 55 | 25 |
| Ryegrass, Italian | 25 | 5 | 20 | 5 | 10 | 20 | 15 | 10 | 10 | 5 | 5 | 30 | 10 | 15 |

TABLE C-continued

| | | | | | | | | | | | | | | |
|---|---|---|---|---|---|---|---|---|---|---|---|---|---|---|
| Soybean | 65 | 90 | 35 | 65 | 70 | 95 | 50 | 65 | 75 | 50 | 45 | 60 | 55 | 50 |
| Speedwell | 98 | 100 | 95 | 100 | — | 100 | 90 | 98 | 98 | 80 | 100 | 100 | 85 | 95 |
| Surinam Grass | 30 | 15 | 25 | 20 | — | 20 | 15 | 10 | 15 | 10 | 10 | 25 | 10 | 20 |
| Velvetleaf | 80 | 30 | 50 | 40 | 60 | 75 | 70 | 60 | 65 | 35 | 15 | 50 | 65 | 50 |
| Waterhemp | 95 | 85 | 98 | 90 | 90 | 100 | 90 | 75 | 75 | 55 | 70 | 100 | 75 | 75 |
| Wheat | 10 | 0 | 10 | 10 | 5 | 10 | 15 | 20 | 15 | 5 | 10 | 20 | 15 | 10 |
| Windgrass | 30 | 20 | 30 | 50 | — | 50 | 35 | 10 | 35 | 30 | 30 | 35 | 35 | 15 |

| | Compounds | | | | | | | | | | | | | |
|---|---|---|---|---|---|---|---|---|---|---|---|---|---|---|
| 31 g ai/ha | 7 | 13 | 15 | 16 | 20 | 21 | 22 | 23 | 26 | 33 | 35 | 72 | 73 | 75 |

| Postemergence | | | | | | | | | | | | | | |
|---|---|---|---|---|---|---|---|---|---|---|---|---|---|---|
| Barnyardgrass | 5 | 10 | 15 | 10 | 10 | 10 | 5 | 10 | 10 | 5 | 5 | 5 | 15 | — |
| Blackgrass | 0 | 5 | 5 | 0 | 5 | 0 | 0 | 5 | 15 | 5 | 0 | 10 | 5 | 5 |
| Buckwheat, Wild | — | — | — | — | — | — | — | — | — | — | — | — | — | 60 |
| Canada Thistle | — | — | — | — | — | — | — | — | — | — | — | — | — | 75 |
| Chickweed | 5 | 70 | 80 | 20 | 60 | 50 | 60 | 50 | 80 | 55 | 40 | 85 | 80 | 85 |
| Corn | 10 | 5 | 10 | 15 | 10 | 5 | 5 | 5 | 25 | 25 | 10 | 15 | 20 | 15 |
| Crabgrass, Large | 5 | 15 | 20 | 15 | 10 | 20 | 15 | 10 | 20 | 5 | 10 | 10 | 10 | 10 |
| Field Poppy | — | — | — | — | — | — | — | — | — | — | — | — | — | 80 |
| Field Violet | — | — | — | — | — | — | — | — | — | — | — | — | — | 98 |
| Foxtail, Giant | 5 | 25 | 30 | 20 | 10 | 10 | 10 | 35 | 10 | 10 | 10 | 30 | 25 | 10 |
| Galium | 0 | 50 | 60 | 50 | 60 | 80 | 25 | 55 | 80 | 70 | 35 | 80 | 70 | 70 |
| Geranium, Cutleaf | — | — | — | — | — | — | — | — | — | — | — | — | — | 40 |
| Johnsongrass | — | — | — | — | — | — | 15 | 20 | 10 | 5 | 10 | 10 | 10 | 10 |
| Kochia | 30 | 30 | 95 | 50 | 95 | 50 | 80 | 50 | 90 | 95 | 40 | 100 | 100 | 85 |
| Lambsquarters | 25 | 55 | 75 | 50 | 80 | 60 | 70 | 55 | 90 | 70 | 40 | 85 | 80 | 55 |
| Morningglory | 25 | 30 | 75 | 30 | 65 | 25 | 10 | 55 | 60 | 65 | 50 | 65 | 75 | 15 |
| Mustard, Wild | — | — | — | — | — | — | — | — | — | — | — | — | — | — |
| Nightshade | — | — | — | — | — | — | — | — | — | — | — | — | — | 80 |
| Nutsedge, Yellow | 0 | 5 | 0 | 5 | 5 | 0 | 0 | 0 | 10 | 5 | 0 | 10 | 15 | 0 |
| Oat, Wild | 0 | 5 | 5 | 5 | 0 | 0 | 5 | 5 | 10 | 10 | 0 | 5 | 5 | 35 |
| Oilseed Rape | 0 | 35 | 95 | 35 | 50 | 40 | 40 | 5 | 75 | 45 | 30 | 60 | 80 | 80 |
| Pigweed | 40 | 70 | 90 | 75 | 95 | 75 | 70 | 75 | 98 | 95 | 70 | 85 | 85 | — |
| Pigweed, Palmer | — | — | — | — | — | — | — | — | — | — | — | — | — | 90 |
| Poinsettia, Wild | — | — | — | — | — | — | — | — | — | — | — | — | — | 70 |
| Ragweed | 20 | 5 | 40 | 10 | 50 | 10 | 35 | 35 | 55 | 30 | 5 | 50 | 55 | 10 |
| Ryegrass, Italian | 0 | 0 | 5 | 0 | 5 | 0 | 0 | 0 | 5 | 5 | 0 | 5 | 5 | 10 |
| Soybean | 25 | 35 | 45 | 35 | 65 | 40 | 40 | 30 | 55 | 65 | 25 | 70 | 70 | 65 |
| Speedwell | — | — | — | — | — | — | — | — | — | — | — | — | — | 95 |
| Surinam Grass | — | — | — | — | — | — | — | — | — | — | — | — | — | 15 |
| Velvetleaf | 20 | 25 | 50 | 25 | 50 | 60 | 40 | 35 | 55 | 50 | 30 | 50 | 60 | 35 |
| Waterhemp | 70 | — | — | — | 95 | 85 | 75 | 90 | 98 | 80 | 80 | 80 | 98 | 90 |
| Wheat | 0 | 0 | 0 | 0 | 0 | 0 | 0 | 0 | 0 | 0 | 0 | 0 | 5 | 5 |
| Windgrass | — | — | — | — | — | — | — | — | — | — | — | — | — | 5 |

| | Compounds | | | | | | | | | | | | | |
|---|---|---|---|---|---|---|---|---|---|---|---|---|---|---|
| 31 g ai/ha | 77 | 79 | 80 | 82 | 89 | 92 | 107 | 110 | 125 | 130 | 136 | 137 | 138 | 143 |

| Postemergence | | | | | | | | | | | | | | |
|---|---|---|---|---|---|---|---|---|---|---|---|---|---|---|
| Barnyardgrass | 25 | — | — | 10 | — | 10 | — | 10 | 5 | 5 | 5 | 10 | — | 10 |
| Blackgrass | 20 | 10 | 5 | 35 | 15 | 10 | 20 | 15 | 20 | 5 | 10 | 10 | 35 | 15 |
| Buckwheat, Wild | — | 80 | 70 | 70 | 75 | — | 75 | 85 | 65 | 90 | 60 | 75 | 80 | 85 |
| Canada Thistle | — | 65 | 75 | 85 | 80 | — | 85 | 90 | 85 | 75 | 75 | 85 | 80 | 85 |
| Chickweed | 80 | 90 | 75 | 85 | 95 | 100 | 90 | 95 | 75 | 75 | 65 | 55 | 85 | 80 |
| Corn | 15 | 25 | 10 | 20 | 15 | 20 | 20 | 20 | 10 | 20 | 10 | 15 | 20 | 20 |
| Crabgrass, Large | 25 | 25 | 15 | 30 | 60 | 10 | 10 | 20 | 10 | 10 | 5 | 20 | 65 | 5 |
| Field Poppy | — | 98 | 75 | 85 | 95 | — | 98 | 100 | 95 | 100 | 85 | 95 | 100 | 90 |
| Field Violet | — | 75 | 85 | 70 | 100 | — | 98 | 95 | 98 | 85 | 90 | 70 | 95 | 80 |
| Foxtail, Giant | 20 | 20 | 10 | 10 | 10 | 20 | 10 | 10 | 10 | 10 | 20 | 20 | 20 | 10 |
| Galium | 98 | 80 | 75 | 75 | 75 | 85 | 80 | 75 | 70 | 80 | 65 | 70 | 80 | 85 |
| Geranium, Cutleaf | — | 50 | 35 | 30 | 35 | — | 35 | 30 | 30 | 35 | 25 | 25 | 35 | 50 |
| Johnsongrass | — | 65 | 5 | 20 | 10 | — | 10 | 10 | 5 | 5 | 5 | 10 | 25 | 5 |
| Kochia | 100 | 80 | 75 | 95 | 75 | 100 | 85 | 100 | 90 | 85 | 80 | 90 | 85 | 100 |
| Lambsquarters | 75 | 85 | 75 | 75 | 75 | 60 | 85 | 90 | 98 | 90 | 75 | 75 | 90 | 90 |
| Morningglory | 85 | 20 | 35 | 40 | 15 | 85 | 60 | 50 | 45 | 25 | 15 | 15 | 55 | 70 |
| Mustard, Wild | — | — | 80 | 95 | — | — | 90 | 90 | 95 | 90 | 95 | 85 | 100 | 100 |
| Nightshade | — | 95 | 65 | 80 | 90 | — | 90 | 85 | 75 | 80 | 75 | 80 | 80 | 85 |
| Nutsedge, Yellow | 10 | 5 | 0 | 10 | 0 | 10 | 5 | 5 | 5 | 0 | 0 | 0 | 0 | 5 |
| Oat, Wild | 5 | 60 | 0 | 40 | 10 | 5 | 40 | 30 | 10 | 10 | 5 | 10 | 55 | 10 |
| Oilseed Rape | 70 | 98 | 60 | 95 | 95 | 50 | 80 | 60 | 85 | 85 | 80 | 95 | 85 | 80 |
| Pigweed | 98 | — | — | — | — | 90 | — | — | — | — | — | — | — | — |
| Pigweed, Palmer | — | 80 | 35 | 80 | 75 | — | 95 | 95 | 85 | 65 | 55 | 45 | 80 | 75 |
| Poinsettia, Wild | — | 75 | 65 | 65 | 60 | — | 75 | 65 | 65 | 70 | 65 | 65 | 60 | 65 |
| Ragweed | 40 | 20 | 10 | 35 | 5 | 40 | 35 | 50 | 35 | 45 | 20 | 35 | 30 | 50 |
| Ryegrass, Italian | 5 | 30 | 0 | 15 | 5 | 15 | 35 | 10 | 5 | 10 | 5 | 5 | 5 | 10 |

TABLE C-continued

| | | | | | | | | | | | | | | |
|---|---|---|---|---|---|---|---|---|---|---|---|---|---|---|
| Soybean | 50 | 70 | 75 | 60 | 40 | 40 | 40 | 40 | 60 | 55 | 40 | 30 | 55 | 40 |
| Speedwell | — | 90 | 100 | 85 | 100 | — | 100 | 95 | 70 | 85 | 80 | 80 | 100 | 80 |
| Surinam Grass | — | 25 | 10 | 20 | 10 | — | 25 | 20 | 10 | 10 | 5 | 10 | 20 | 10 |
| Velvetleaf | 50 | 75 | 35 | 45 | 35 | 50 | 65 | 40 | 35 | 45 | 50 | 15 | 35 | 55 |
| Waterhemp | 98 | 95 | 80 | 95 | 70 | 85 | 98 | 90 | 80 | 75 | 70 | 60 | 98 | 80 |
| Wheat | 0 | 5 | 0 | 10 | 10 | 0 | 5 | 5 | 5 | 5 | 5 | 5 | 5 | 10 |
| Windgrass | — | 35 | 5 | 35 | 10 | — | 15 | 25 | 15 | 15 | 10 | 10 | 15 | 35 |

| 31 g ai/ha | Compound 144 | 31 g ai/ha | Compound 144 |
|---|---|---|---|
| Postemergence | | | |
| Barnyardgrass | 5 | Nightshade | 75 |
| Blackgrass | 10 | Nutsedge, Yellow | 0 |
| Buckwheat, Wild | 55 | Oat, Wild | 30 |
| Canada Thistle | 60 | Oilseed Rape | 35 |
| Chickweed | 55 | Pigweed | — |
| Corn | 15 | Pigweed, Palmer | 35 |
| Crabgrass, Large | 25 | Poinsettia, Wild | 35 |
| Field Poppy | 80 | Ragweed | 15 |
| Field Violet | 65 | Ryegrass, Italian | 10 |
| Foxtail, Giant | 10 | Soybean | 30 |
| Galium | 70 | Speedwell | 70 |
| Geranium, Cutleaf | 20 | Surinam Grass | 20 |
| Johnsongrass | 5 | Velvetleaf | 30 |
| Kochia | 90 | Waterhemp | 60 |
| Lambsquarters | 75 | Wheat | 5 |
| Morningglory | 20 | Windgrass | 10 |
| Mustard, Wild | 70 | | |

| | Compounds | | | | | | | | | | | | |
|---|---|---|---|---|---|---|---|---|---|---|---|---|---|
| 16 g ai/ha | 7 | 13 | 15 | 16 | 20 | 21 | 22 | 23 | 26 | 33 | 35 | 72 | 73 | 75 |
| Postemergence | | | | | | | | | | | | | | |
| Barnyardgrass | 5 | 10 | 20 | 5 | 10 | 10 | 5 | 10 | 10 | 5 | 5 | 5 | 10 | — |
| Blackgrass | 0 | 0 | 0 | 0 | 5 | 0 | 0 | 0 | 10 | 5 | 0 | 5 | 10 | 0 |
| Buckwheat, Wild | — | — | — | — | — | — | — | — | — | — | — | — | — | 45 |
| Canada Thistle | — | — | — | — | — | — | — | — | — | — | — | — | — | 70 |
| Chickweed | 5 | 40 | 35 | 20 | 60 | 40 | 20 | 5 | 55 | 50 | 5 | 65 | 80 | 60 |
| Corn | 5 | 10 | 15 | 5 | 5 | 5 | 5 | 5 | 20 | 20 | 5 | 10 | 10 | 10 |
| Crabgrass, Large | 5 | 5 | 30 | 10 | 10 | 10 | 10 | 10 | 10 | 5 | 10 | 10 | 15 | 10 |
| Field Poppy | — | — | — | — | — | — | — | — | — | — | — | — | — | 70 |
| Field Violet | — | — | — | — | — | — | — | — | — | — | — | — | — | 80 |
| Foxtail, Giant | 5 | 10 | 25 | 10 | 10 | 10 | 10 | 10 | 10 | 5 | 5 | 30 | 15 | 10 |
| Galium | 0 | 65 | 70 | 45 | 70 | 55 | 10 | 50 | 55 | 50 | 35 | 80 | 70 | 40 |
| Geranium, Cutleaf | — | — | — | — | — | — | — | — | — | — | — | — | — | 30 |
| Johnsongrass | — | — | — | — | — | — | 0 | 10 | 10 | 0 | 5 | 5 | 5 | 5 |
| Kochia | 0 | 30 | 90 | 40 | 95 | 60 | 50 | 5 | 90 | 90 | 5 | 100 | 98 | 75 |
| Lambsquarters | 5 | 50 | 70 | 40 | 65 | 65 | 65 | 25 | 75 | 60 | 50 | 75 | 75 | 50 |
| Morningglory | 5 | 20 | 65 | 5 | 75 | 10 | 5 | 10 | 65 | 55 | 40 | 75 | 70 | 5 |
| Mustard, Wild | — | — | — | — | — | — | — | — | — | — | — | — | — | — |
| Nightshade | — | — | — | — | — | — | — | — | — | — | — | — | — | 75 |
| Nutsedge, Yellow | 0 | 5 | 0 | 0 | 0 | 0 | 0 | 0 | 5 | 5 | 0 | 5 | 5 | 0 |
| Oat, Wild | 0 | 0 | 5 | 0 | 0 | 0 | 0 | 5 | 10 | 5 | 0 | 5 | 5 | 5 |
| Oilseed Rape | 0 | 0 | 45 | 15 | 50 | 30 | 35 | 5 | 40 | 35 | 20 | 50 | 5 | 60 |
| Pigweed | 35 | 75 | 90 | 50 | 85 | 85 | 60 | 60 | 75 | 95 | 80 | 80 | 90 | — |
| Pigweed, Palmer | — | — | — | — | — | — | — | — | — | — | — | — | — | 75 |
| Poinsettia, Wild | — | — | — | — | — | — | — | — | — | — | — | — | — | 65 |
| Ragweed | 10 | 5 | 30 | 20 | 30 | 10 | 5 | 15 | 40 | 40 | 0 | 35 | 50 | 5 |
| Ryegrass, Italian | 10 | 0 | 0 | 0 | 0 | 0 | 0 | 0 | 5 | 0 | 0 | 5 | 5 | 0 |
| Soybean | 25 | 30 | 45 | 15 | 25 | 30 | 40 | 20 | 65 | 25 | 25 | 60 | 45 | 50 |
| Speedwell | — | — | — | — | — | — | — | — | — | — | — | — | — | 90 |
| Surinam Grass | — | — | — | — | — | — | — | — | — | — | — | — | — | 10 |
| Velvetleaf | 5 | 20 | 50 | 20 | 20 | 40 | 50 | 10 | 30 | 25 | 40 | 40 | 40 | 30 |
| Waterhemp | 35 | — | — | — | 75 | 75 | 75 | 80 | 95 | 90 | 65 | 85 | 85 | 85 |
| Wheat | 0 | 0 | 0 | 0 | 0 | 0 | 0 | 0 | 0 | 0 | 0 | 0 | 0 | 0 |
| Windgrass | — | — | — | — | — | — | — | — | — | — | — | — | — | 0 |

| | Compounds | | | | | | | | | | | | |
|---|---|---|---|---|---|---|---|---|---|---|---|---|---|
| 16 g ai/ha | 77 | 79 | 80 | 82 | 89 | 92 | 107 | 110 | 125 | 130 | 136 | 137 | 138 | 143 |
| Postemergence | | | | | | | | | | | | | | |
| Barnyardgrass | 15 | — | — | 10 | — | 10 | — | 10 | 5 | 5 | 5 | 10 | — | 5 |
| Blackgrass | 5 | 20 | 0 | 30 | 10 | 5 | 5 | 10 | 10 | 5 | 5 | 5 | 5 | 10 |
| Buckwheat, Wild | — | 75 | 70 | 80 | 70 | — | 45 | 85 | 70 | 35 | 50 | 70 | 70 | 75 |

TABLE C-continued

| | | | | | | | | | | | | | | |
|---|---|---|---|---|---|---|---|---|---|---|---|---|---|---|
| Canada Thistle | — | 55 | 75 | 85 | 80 | — | 80 | 65 | 80 | 75 | 65 | 75 | 80 | 85 |
| Chickweed | 80 | 95 | 60 | 55 | 65 | 100 | 80 | 60 | 70 | 75 | 55 | 70 | 75 | 80 |
| Corn | 15 | 15 | 15 | 20 | 15 | 10 | 10 | 10 | 10 | 10 | 5 | 10 | 15 | 15 |
| Crabgrass, Large | 10 | 10 | 10 | 10 | 55 | 20 | 10 | 10 | 10 | 5 | 5 | 10 | 35 | 5 |
| Field Poppy | — | 85 | 70 | 50 | 90 | — | 80 | 85 | 90 | 100 | 65 | 85 | 100 | 80 |
| Field Violet | — | 70 | 75 | 60 | 100 | — | 95 | 80 | 90 | 80 | 85 | 65 | 90 | 75 |
| Foxtail, Giant | 10 | 10 | 5 | 10 | 10 | 10 | 10 | 10 | 10 | 10 | 10 | 20 | 10 | 20 |
| Galium | 75 | 75 | 70 | 50 | 75 | 80 | 75 | 60 | 65 | 75 | 50 | 55 | 65 | 75 |
| Geranium, Cutleaf | — | 45 | 30 | 30 | 35 | — | 25 | 5 | 25 | 25 | 15 | 10 | 30 | 30 |
| Johnsongrass | — | 40 | 5 | 5 | 5 | — | 20 | 5 | 5 | 5 | 5 | 5 | 10 | 5 |
| Kochia | 95 | 75 | 55 | 80 | 70 | 100 | 80 | 95 | 85 | 80 | 80 | 85 | 75 | 98 |
| Lambsquarters | 55 | 75 | 50 | 70 | 70 | 40 | 80 | 75 | 70 | 75 | 55 | 55 | 65 | 75 |
| Morningglory | 50 | 10 | 25 | 25 | 5 | 20 | 20 | 30 | 20 | 10 | 10 | 10 | 10 | 15 |
| Mustard, Wild | — | — | 75 | 95 | 100 | — | 85 | 90 | 90 | 98 | 85 | 100 | 100 | 100 |
| Nightshade | — | 90 | 60 | 85 | 75 | — | 75 | 75 | 50 | 75 | 70 | 60 | 75 | 65 |
| Nutsedge, Yellow | 5 | 0 | 0 | 10 | 0 | 0 | 5 | 0 | 5 | 0 | 0 | 0 | 0 | 0 |
| Oat, Wild | 0 | 15 | 0 | 25 | 15 | 5 | 5 | 20 | 5 | 5 | 5 | 5 | 10 | 10 |
| Oilseed Rape | 10 | 80 | 50 | 70 | 60 | 5 | 65 | 60 | 80 | 70 | 65 | 90 | 70 | 85 |
| Pigweed | 95 | — | — | — | — | 85 | — | — | — | — | — | — | — | — |
| Pigweed, Palmer | — | 60 | 30 | 75 | 55 | — | 90 | 75 | 40 | 35 | 50 | 20 | 75 | 45 |
| Poinsettia, Wild | — | 30 | 65 | 40 | 55 | — | 70 | 40 | 65 | 55 | 40 | 15 | 30 | 55 |
| Ragweed | 40 | 30 | 5 | 40 | 0 | 35 | 25 | 40 | 5 | 25 | 20 | 20 | 0 | 20 |
| Ryegrass, Italian | 0 | 5 | 0 | 5 | 5 | 10 | 5 | 5 | 5 | 5 | 0 | 5 | 5 | 5 |
| Soybean | 25 | 60 | 60 | 25 | 35 | 30 | 50 | 40 | 25 | 40 | 30 | 20 | 35 | 30 |
| Speedwell | — | 85 | 90 | 75 | 95 | — | 100 | 60 | 55 | 80 | 75 | 75 | 95 | 80 |
| Surinam Grass | — | 25 | 10 | 20 | 10 | — | 10 | 15 | 5 | 10 | 5 | 5 | 20 | 5 |
| Velvetleaf | 35 | 30 | 30 | 35 | 20 | 35 | 60 | 50 | 20 | 25 | 20 | 10 | 10 | 35 |
| Waterhemp | 95 | 95 | 80 | 65 | 70 | 80 | 95 | 85 | 75 | 65 | 70 | 40 | 98 | 75 |
| Wheat | 0 | 5 | 0 | 5 | 0 | 0 | 5 | 5 | 5 | 10 | 0 | 5 | 5 | 5 |
| Windgrass | — | 20 | 0 | 10 | 10 | — | 5 | 20 | 10 | 10 | 5 | 10 | 0 | 30 |

| 16 g ai/ha | Compound 144 | 16 g ai/ha | Compound 144 |
|---|---|---|---|
| Postemergence | | | |
| Barnyardgrass | 5 | Nightshade | 65 |
| Blackgrass | 10 | Nutsedge, Yellow | 0 |
| Buckwheat, Wild | 70 | Oat, Wild | 20 |
| Canada Thistle | 90 | Oilseed Rape | 35 |
| Chickweed | 50 | Pigweed | — |
| Corn | 15 | Pigweed, Palmer | 25 |
| Crabgrass, Large | 10 | Poinsettia, Wild | 30 |
| Field Poppy | 60 | Ragweed | 10 |
| Field Violet | 60 | Ryegrass, Italian | 5 |
| Foxtail, Giant | 5 | Soybean | 30 |
| Galium | 50 | Speedwell | 60 |
| Geranium, Cutleaf | 15 | Surinam Grass | 10 |
| Johnsongrass | 5 | Velvetleaf | 25 |
| Kochia | 85 | Waterhemp | 35 |
| Lambsquarters | 40 | Wheat | 5 |
| Morningglory | 30 | Windgrass | 10 |
| Mustard, Wild | 70 | | |

| 8 g ai/ha | Compound 13 | 4 g ai/ha | Compound 13 |
|---|---|---|---|
| Postemergence | | | |
| Barnyardgrass | 5 | Barnyardgrass | 5 |
| Blackgrass | 0 | Blackgrass | 0 |
| Chickweed | 5 | Chickweed | 5 |
| Corn | 5 | Corn | 5 |
| Crabgrass, Large | 5 | Crabgrass, Large | 5 |
| Foxtail, Giant | 5 | Foxtail, Giant | 5 |
| Galium | 5 | Galium | 10 |
| Kochia | 5 | Kochia | 0 |
| Lambsquarters | 60 | Lambsquarters | 30 |
| Morningglory | 5 | Morningglory | 5 |
| Nutsedge, Yellow | 0 | Nutsedge, Yellow | 0 |
| Oat, Wild | 0 | Oat, Wild | 0 |
| Oilseed Rape | 0 | Oilseed Rape | 0 |
| Pigweed | 60 | Pigweed | 30 |
| Ragweed | 5 | Ragweed | 5 |
| Ryegrass, Italian | 0 | Ryegrass, Italian | 0 |
| Soybean | 20 | Soybean | 15 |
| Velvetleaf | 15 | Velvetleaf | 15 |
| Wheat | 0 | Wheat | 0 |

TABLE C-continued

| 125 g ai/ha | Compounds | | | | | | | | | | | | | |
|---|---|---|---|---|---|---|---|---|---|---|---|---|---|---|
| | 15 | 16 | 20 | 21 | 26 | 30 | 33 | 61 | 72 | 73 | 75 | 77 | 79 | 80 |
| Preemergence | | | | | | | | | | | | | | |
| Barnyardgrass | 100 | 75 | 85 | 98 | 100 | 25 | 100 | 65 | 100 | 100 | 100 | 100 | 95 | 100 |
| Blackgrass | 80 | 10 | 100 | 90 | 90 | 0 | 90 | 5 | 100 | 100 | 75 | 100 | 90 | 90 |
| Corn | 25 | 10 | 30 | 20 | 40 | 5 | 10 | 0 | 60 | 50 | 5 | 35 | 30 | 20 |
| Crabgrass, Large | 100 | 100 | 100 | 100 | 100 | 98 | 100 | 90 | 100 | 100 | 98 | 100 | 98 | 98 |
| Foxtail, Giant | 100 | 100 | 100 | 90 | 98 | 75 | 100 | 65 | 100 | 100 | 98 | 100 | 98 | 100 |
| Galium | — | — | 95 | 100 | 100 | 85 | 95 | 15 | 100 | 100 | 0 | 98 | 5 | 98 |
| Johnsongrass | — | — | — | — | 98 | 15 | 35 | 20 | 100 | 95 | 70 | — | 70 | 60 |
| Kochia | — | — | — | — | — | — | — | 30 | — | — | 100 | — | 100 | 100 |
| Lambsquarters | 95 | 50 | 90 | 70 | 95 | 55 | 85 | 60 | 100 | 100 | 70 | 98 | 85 | 98 |
| Morningglory | 60 | 25 | 10 | 10 | 95 | 35 | 40 | 0 | 95 | 75 | 10 | 65 | 60 | 75 |
| Nightshade | — | — | — | — | — | — | — | 75 | — | — | 80 | — | 95 | 90 |
| Nutsedge, Yellow | 50 | 0 | 10 | 0 | 45 | 5 | 5 | 0 | 0 | 10 | 20 | 30 | 0 | 35 |
| Oat, Wild | — | — | — | — | — | — | — | 5 | — | — | 5 | — | 40 | 30 |
| Oilseed Rape | 100 | 100 | 50 | 100 | 100 | 100 | 100 | 10 | 100 | 65 | 40 | 100 | 95 | 100 |
| Pigweed | 100 | 95 | 100 | 100 | 100 | 100 | 100 | — | 100 | 100 | — | 100 | — | — |
| Pigweed, Palmer | — | — | — | — | — | — | — | 75 | — | — | 100 | — | 90 | 98 |
| Poinsettia, Wild | — | — | — | — | — | — | — | 0 | — | — | 35 | — | 40 | 85 |
| Ragweed | 20 | 0 | 0 | 0 | 50 | 0 | 50 | 30 | 45 | 25 | 5 | 45 | 30 | 20 |
| Ryegrass, Italian | 50 | 5 | 70 | 90 | 95 | 5 | 85 | 5 | 100 | 100 | 15 | 90 | 35 | 25 |
| Soybean | 55 | 5 | 10 | 0 | — | 60 | 30 | 10 | 90 | 40 | 50 | 25 | 5 | 85 |
| Surinam Grass | — | — | — | — | — | — | — | 25 | — | — | 80 | — | 85 | 98 |
| Velvetleaf | 100 | 75 | 50 | 100 | 100 | 40 | 100 | 5 | 100 | 95 | 25 | 100 | 75 | 100 |
| Waterhemp | 100 | 100 | 98 | 98 | 100 | 100 | 100 | 100 | 100 | 100 | 98 | 100 | 100 | 100 |
| Wheat | 5 | 0 | 5 | 0 | 15 | 10 | 5 | 10 | 80 | 70 | 10 | 0 | 15 | 15 |
| Windgrass | — | — | — | — | — | — | — | 70 | — | — | 100 | — | 100 | 100 |

| 125 g ai/ha | Compounds | | | | | | | | | |
|---|---|---|---|---|---|---|---|---|---|---|
| | 82 | 89 | 92 | 107 | 125 | 130 | 136 | 138 | 143 | 144 |
| Preemergence | | | | | | | | | | |
| Barnyardgrass | 90 | 100 | 100 | 100 | — | — | — | 95 | — | 95 |
| Blackgrass | 5 | 90 | 100 | 90 | 90 | 85 | 95 | 90 | 75 | 30 |
| Corn | 5 | 10 | 40 | 45 | 5 | 25 | 5 | 5 | 20 | 30 |
| Crabgrass, Large | 98 | 98 | 100 | 100 | 100 | 100 | 100 | 98 | 100 | 100 |
| Foxtail, Giant | 98 | 85 | 100 | 98 | 100 | 100 | 100 | 100 | 100 | 100 |
| Galium | 80 | 0 | — | 95 | 80 | 90 | 90 | 5 | 80 | 55 |
| Johnsongrass | 85 | 60 | — | 80 | 75 | 85 | 70 | 60 | 80 | 70 |
| Kochia | 95 | 90 | — | 100 | 98 | 98 | 98 | 80 | 90 | 100 |
| Lambsquarters | 70 | 65 | 100 | 95 | 95 | 95 | 80 | 70 | 95 | 75 |
| Morningglory | 10 | 20 | 70 | 85 | 50 | 10 | 30 | 10 | 25 | 20 |
| Nightshade | 85 | 85 | — | 90 | — | — | — | 80 | — | 100 |
| Nutsedge, Yellow | 0 | 0 | 50 | 0 | 5 | 0 | 5 | 0 | 5 | 70 |
| Oat, Wild | 5 | 10 | — | 65 | 55 | 60 | 45 | 30 | 5 | 10 |
| Oilseed Rape | 50 | 15 | 100 | 98 | 80 | 95 | 98 | 20 | 98 | 90 |
| Pigweed | — | — | 100 | — | — | — | — | — | — | — |
| Pigweed, Palmer | 100 | 98 | — | 100 | 100 | 85 | 100 | 100 | 100 | 100 |
| Poinsettia, Wild | 20 | 40 | — | 70 | 30 | 45 | 50 | 50 | 25 | 80 |
| Ragweed | 30 | 50 | 60 | 50 | 35 | 10 | 40 | 10 | 5 | 10 |
| Ryegrass, Italian | 5 | 40 | 95 | 90 | 85 | 70 | 65 | 80 | 45 | 60 |
| Soybean | 0 | 10 | 60 | 45 | 20 | 30 | 40 | 5 | 20 | 60 |
| Surinam Grass | 35 | 75 | — | 98 | 65 | 80 | 100 | 75 | 50 | 60 |
| Velvetleaf | 10 | 60 | 100 | 98 | 65 | 85 | 65 | 50 | 70 | 45 |
| Waterhemp | 100 | 100 | 100 | 100 | 100 | 100 | 100 | 98 | 100 | 100 |
| Wheat | 0 | 5 | 20 | 35 | 5 | 0 | 10 | 10 | 0 | 5 |
| Windgrass | 90 | 100 | — | 100 | 100 | 100 | 100 | 100 | 100 | 90 |

| 62 g ai/ha | Compounds | | | | | | | | | | | | | |
|---|---|---|---|---|---|---|---|---|---|---|---|---|---|---|
| | 15 | 16 | 20 | 21 | 26 | 30 | 33 | 61 | 72 | 73 | 75 | 77 | 79 | 80 |
| Preemergence | | | | | | | | | | | | | | |
| Barnyardgrass | 100 | 30 | 30 | 90 | 100 | 10 | 95 | 50 | 80 | 100 | 80 | 98 | 75 | 70 |
| Blackgrass | 50 | 5 | 85 | 55 | 90 | 0 | 70 | 0 | 98 | 100 | 80 | 90 | 75 | 70 |
| Corn | 10 | 0 | 0 | 5 | 25 | 0 | 10 | 10 | 20 | 40 | 0 | 20 | 5 | 5 |
| Crabgrass, Large | 100 | 90 | 98 | 98 | 100 | 80 | 100 | 75 | 100 | 100 | 98 | 100 | 100 | 100 |
| Foxtail, Giant | 100 | 90 | 90 | 95 | 98 | 65 | 98 | 60 | 75 | 100 | 65 | 100 | 80 | 85 |
| Galium | — | — | 80 | 5 | 95 | 60 | 60 | 10 | 90 | 100 | 5 | 98 | 70 | 75 |
| Johnsongrass | — | — | — | — | 80 | 0 | 25 | 0 | 70 | 80 | 30 | — | 50 | 55 |
| Kochia | — | — | — | — | — | — | — | 5 | — | — | 90 | — | 90 | 100 |
| Lambsquarters | 85 | 20 | 10 | 25 | 95 | 30 | 80 | 50 | 90 | 90 | 35 | 100 | 70 | 95 |
| Morningglory | 35 | 25 | 5 | 5 | 85 | 10 | 25 | 0 | 55 | 60 | 20 | 35 | 10 | 40 |

TABLE C-continued

| | | | | | | | | | | | | | |
|---|---|---|---|---|---|---|---|---|---|---|---|---|---|
| Nightshade | — | — | — | — | — | — | — | 50 | — | — | 75 | — | 80 | 85 |
| Nutsedge, Yellow | 5 | 0 | 0 | 0 | 15 | 0 | 5 | 0 | 0 | 0 | 0 | 0 | 0 | 0 |
| Oat, Wild | — | — | — | — | — | — | — | 5 | — | — | 0 | — | 5 | 10 |
| Oilseed Rape | 100 | 60 | 50 | 75 | 100 | 100 | 85 | 0 | 80 | 50 | 10 | 100 | 70 | 70 |
| Pigweed | 100 | 50 | 100 | 98 | 100 | 100 | 100 | — | 100 | 100 | — | 100 | — | — |
| Pigweed, Palmer | — | — | — | — | — | — | — | 70 | — | — | 95 | — | 90 | 100 |
| Poinsettia, Wild | — | — | — | — | — | — | — | 0 | — | — | 35 | — | 10 | 40 |
| Ragweed | 30 | 5 | 0 | 0 | 60 | 0 | 40 | 5 | 40 | 10 | 0 | 40 | 20 | 5 |
| Ryegrass, Italian | 15 | 5 | 30 | 15 | 85 | 0 | 30 | 0 | 45 | 85 | 5 | 35 | 30 | 5 |
| Soybean | 40 | 0 | 0 | 0 | 35 | 10 | — | 20 | 15 | 25 | 10 | 15 | 5 | 40 |
| Surinam Grass | — | — | — | — | — | — | — | 60 | — | — | 35 | — | 50 | 60 |
| Velvetleaf | 100 | 50 | 5 | 70 | 85 | 10 | 55 | 5 | 55 | 75 | 35 | 70 | 20 | 70 |
| Waterhemp | 100 | 85 | 100 | 95 | 100 | 100 | 100 | 90 | 100 | 100 | 98 | 100 | 95 | 100 |
| Wheat | 0 | 0 | 0 | 0 | 5 | 0 | 0 | 5 | 30 | 30 | 10 | 0 | 5 | 0 |
| Windgrass | — | — | — | — | — | — | — | 40 | — | — | 100 | — | 100 | 100 |

| | Compounds | | | | | | | | | |
|---|---|---|---|---|---|---|---|---|---|---|
| 62 g ai/ha | 82 | 89 | 92 | 107 | 125 | 130 | 136 | 138 | 143 | 144 |
| | Preemergence | | | | | | | | | |
| Barnyardgrass | 20 | 90 | 98 | 100 | — | — | — | 80 | — | 70 |
| Blackgrass | 5 | 85 | 100 | 90 | 60 | 60 | 60 | 80 | 80 | 40 |
| Corn | 0 | 0 | 35 | 15 | 5 | 5 | 5 | 5 | 0 | 5 |
| Crabgrass, Large | 90 | 100 | 100 | 100 | 100 | 100 | 100 | 98 | 100 | 100 |
| Foxtail, Giant | 90 | 60 | 100 | 98 | 98 | 98 | 70 | 85 | 100 | 100 |
| Galium | 0 | 0 | — | 90 | 30 | 90 | 50 | 5 | 80 | 50 |
| Johnsongrass | 40 | 30 | — | 70 | 60 | 70 | 35 | 50 | 50 | 40 |
| Kochia | 90 | 85 | — | 100 | 90 | 65 | 85 | 80 | 90 | 100 |
| Lambsquarters | 20 | 0 | 100 | 85 | 60 | 35 | 25 | 25 | 95 | 65 |
| Morningglory | 0 | 5 | 60 | 40 | 10 | 20 | 5 | 0 | 5 | 10 |
| Nightshade | 40 | 65 | — | 80 | — | — | — | 80 | — | 90 |
| Nutsedge, Yellow | 0 | 0 | 5 | 0 | 0 | 0 | 0 | 0 | 0 | 60 |
| Oat, Wild | 5 | 30 | — | 30 | 10 | 35 | 5 | 5 | 5 | 10 |
| Oilseed Rape | 5 | 0 | 100 | 85 | 50 | 40 | 70 | 5 | 80 | 5 |
| Pigweed | — | — | 100 | — | — | — | — | — | — | — |
| Pigweed, Palmer | 100 | 90 | — | 100 | 100 | 100 | 100 | 100 | 100 | 100 |
| Poinsettia, Wild | 0 | 20 | — | 40 | 25 | 10 | 25 | 5 | 20 | 40 |
| Ragweed | 20 | 5 | 60 | 50 | 5 | 5 | 0 | 0 | 0 | 0 |
| Ryegrass, Italian | 5 | 15 | 55 | 70 | 40 | 60 | 35 | 20 | 30 | 0 |
| Soybean | 0 | 5 | 70 | 35 | 0 | 10 | 15 | 0 | 15 | 30 |
| Surinam Grass | 25 | 65 | — | 98 | 40 | 65 | 10 | 65 | 35 | 70 |
| Velvetleaf | 0 | 25 | 100 | 98 | 60 | 75 | 15 | 20 | 40 | 15 |
| Waterhemp | 100 | 100 | 100 | 100 | 100 | 100 | 100 | 100 | 100 | 98 |
| Wheat | 0 | 0 | 0 | 15 | 0 | 5 | 0 | 5 | 0 | 0 |
| Windgrass | 80 | 65 | — | 100 | 90 | 100 | 85 | 100 | 100 | 80 |

| | Compounds | | | | | | | | | | | | |
|---|---|---|---|---|---|---|---|---|---|---|---|---|---|
| 31 g ai/ha | 13 | 15 | 16 | 20 | 21 | 26 | 30 | 33 | 61 | 72 | 73 | 75 | 77 | 79 |
| | Preemergence | | | | | | | | | | | | |
| Barnyardgrass | 40 | 85 | 15 | 5 | 55 | 75 | 15 | 40 | 0 | 90 | 80 | 60 | 60 | 60 |
| Blackgrass | 0 | 0 | 0 | 40 | 35 | 90 | 0 | 10 | 0 | 98 | 98 | 5 | 15 | 10 |
| Corn | 10 | 0 | 0 | 0 | 0 | 0 | 0 | 0 | 0 | 20 | 20 | 0 | 15 | 0 |
| Crabgrass, Large | 85 | 100 | 75 | 50 | 75 | 100 | 35 | 98 | 10 | 100 | 100 | 85 | 100 | 98 |
| Foxtail, Giant | 95 | 100 | 25 | 50 | 80 | 98 | 30 | 95 | 50 | 80 | 100 | 25 | 100 | 70 |
| Galium | — | — | — | 0 | 0 | 90 | 10 | 60 | 0 | 75 | 10 | 0 | 0 | 0 |
| Johnsongrass | — | — | — | — | — | 50 | 0 | 5 | 0 | 65 | 40 | 0 | — | 5 |
| Kochia | — | — | — | — | — | — | — | — | 5 | — | — | 50 | — | 90 |
| Lambsquarters | 15 | 70 | 20 | 5 | 30 | 85 | 25 | 60 | 15 | 80 | 90 | 10 | 60 | 10 |
| Morningglory | 5 | 20 | 0 | 0 | 0 | 10 | 10 | 0 | 0 | 40 | 10 | 0 | 20 | 10 |
| Nightshade | — | — | — | — | — | — | — | 60 | — | — | 75 | — | 65 | |
| Nutsedge, Yellow | 5 | 0 | 0 | 0 | 0 | 0 | 0 | 0 | 0 | 0 | 0 | 0 | 0 | 0 |
| Oat, Wild | — | — | — | — | — | — | — | 0 | — | — | 0 | — | 0 | |
| Oilseed Rape | 50 | 100 | 50 | 0 | 0 | 85 | 55 | 80 | 0 | 80 | 20 | 0 | 55 | 0 |
| Pigweed | 60 | 100 | 0 | 55 | 55 | 100 | 95 | 100 | — | 100 | 95 | — | 100 | — |
| Pigweed, Palmer | — | — | — | — | — | — | — | — | 50 | — | — | 100 | — | 85 |
| Poinsettia, Wild | — | — | — | — | — | — | — | — | 0 | — | — | 40 | — | 0 |
| Ragweed | 10 | 10 | 0 | 0 | 0 | 30 | 0 | 35 | 0 | 0 | 0 | 0 | 0 | 0 |
| Ryegrass, Italian | 0 | 5 | 0 | 0 | 10 | 75 | 0 | 30 | 0 | 45 | 35 | 5 | 30 | 10 |
| Soybean | 5 | 10 | 0 | 0 | 0 | 10 | — | — | 20 | 0 | 0 | 0 | 5 | 0 |
| Surinam Grass | — | — | — | — | — | — | — | — | 10 | — | — | 30 | — | 30 |
| Velvetleaf | 70 | 85 | 5 | 0 | 40 | 30 | 0 | 30 | 5 | 60 | 30 | 5 | 30 | 5 |
| Waterhemp | 100 | 100 | 60 | 85 | 75 | 100 | 100 | 100 | 75 | 100 | 100 | 95 | 100 | 98 |
| Wheat | 5 | 0 | 0 | 0 | 0 | 20 | 0 | 0 | 0 | 0 | 0 | 0 | 0 | 5 |
| Windgrass | — | — | — | — | — | — | — | — | 5 | — | — | 45 | — | 80 |

TABLE C-continued

| 31 g ai/ha | Compounds | | | | | | | | | | |
|---|---|---|---|---|---|---|---|---|---|---|---|
| | 80 | 82 | 89 | 92 | 107 | 125 | 130 | 136 | 138 | 143 | 144 |
| | Preemergence | | | | | | | | | | |
| Barnyardgrass | 30 | 5 | 35 | 85 | 85 | — | — | — | 40 | — | 40 |
| Blackgrass | 10 | 0 | 15 | 80 | 90 | 60 | 30 | 35 | 50 | 75 | 10 |
| Corn | 5 | 0 | 0 | 15 | 0 | 0 | 0 | 0 | 0 | 0 | 0 |
| Crabgrass, Large | 80 | 70 | 98 | 100 | 98 | 98 | 100 | 85 | 95 | 100 | 98 |
| Foxtail, Giant | 40 | 80 | 5 | 100 | 98 | 85 | 70 | 65 | 80 | 98 | 85 |
| Galium | 5 | 0 | 0 | — | 60 | 5 | 50 | 0 | 0 | 30 | 50 |
| Johnsongrass | 30 | 5 | 40 | — | 30 | 5 | 10 | 25 | 0 | 25 | 10 |
| Kochia | 95 | 50 | 60 | — | 100 | 60 | 65 | 80 | 75 | 80 | 90 |
| Lambsquarters | 70 | 20 | 0 | 100 | 75 | 30 | 30 | 30 | 35 | 10 | 40 |
| Morningglory | 20 | 0 | 0 | 40 | 0 | 10 | 5 | 0 | 0 | 0 | 0 |
| Nightshade | 70 | 20 | 75 | — | 60 | — | — | — | 50 | — | 65 |
| Nutsedge, Yellow | 0 | 0 | 0 | 5 | 0 | 0 | 0 | 0 | 0 | 0 | 20 |
| Oat, Wild | 0 | 0 | 10 | — | 5 | 0 | 15 | 0 | 0 | 0 | 5 |
| Oilseed Rape | 80 | 0 | 0 | 100 | 40 | 5 | 10 | 5 | 0 | 5 | 0 |
| Pigweed | — | — | — | 100 | — | — | — | — | — | — | — |
| Pigweed, Palmer | 85 | 85 | 70 | — | 100 | 100 | 75 | 75 | 60 | 100 | 100 |
| Poinsettia, Wild | 30 | 0 | 0 | — | 10 | 0 | 0 | 5 | 0 | 5 | 5 |
| Ragweed | 0 | 0 | 0 | 55 | 30 | 10 | 0 | 20 | 0 | 0 | 0 |
| Ryegrass, Italian | 0 | 0 | 5 | 5 | 35 | 30 | 35 | 30 | 10 | 20 | 0 |
| Soybean | 20 | 0 | 5 | 40 | 20 | 0 | 0 | 0 | 0 | 0 | 0 |
| Surinam Grass | 50 | 10 | 35 | — | 60 | 20 | 50 | 25 | 65 | 10 | 5 |
| Velvetleaf | 55 | 0 | 20 | 75 | 75 | 5 | 10 | 5 | 25 | 10 | 0 |
| Waterhemp | 100 | 50 | 85 | 100 | 98 | 100 | 100 | 100 | 85 | 98 | 98 |
| Wheat | 0 | 0 | 0 | 0 | 10 | 0 | 0 | 0 | 5 | 0 | — |
| Windgrass | 60 | 30 | 50 | — | 100 | 85 | 70 | 30 | 100 | 85 | 30 |

| 16 g ai/ha | Compounds | | | | | | | | | | | | |
|---|---|---|---|---|---|---|---|---|---|---|---|---|---|
| | 13 | 15 | 16 | 20 | 21 | 26 | 30 | 33 | 61 | 72 | 73 | 75 | 77 | 79 |
| | Preemergence | | | | | | | | | | | | |
| Barnyardgrass | 10 | 10 | 0 | 0 | 10 | 40 | 10 | 20 | 0 | 25 | 15 | 5 | 20 | 5 |
| Blackgrass | 0 | 0 | 0 | 0 | 5 | 45 | 0 | 0 | 0 | 60 | 5 | 0 | 5 | 5 |
| Corn | 5 | 0 | 0 | 0 | 0 | 0 | 0 | 0 | 0 | 5 | 0 | 0 | 0 | 0 |
| Crabgrass, Large | 60 | 95 | 5 | 5 | 20 | 98 | 0 | 75 | 0 | 100 | 98 | 65 | 98 | 65 |
| Foxtail, Giant | 0 | 100 | 5 | 35 | 20 | 95 | 5 | 60 | 0 | 55 | 98 | 0 | 95 | 40 |
| Galium | — | — | — | 10 | — | 5 | 80 | 0 | 0 | 5 | 5 | 0 | 0 | 0 |
| Johnsongrass | — | — | — | — | — | 55 | 0 | 0 | 0 | 5 | 0 | 0 | — | 0 |
| Kochia | — | — | — | — | — | — | — | — | 0 | — | — | 0 | — | 5 |
| Lambsquarters | 50 | 60 | 0 | 0 | 0 | 70 | 10 | 25 | 5 | 65 | 85 | 0 | 50 | 0 |
| Morningglory | 5 | 20 | 10 | 0 | 0 | 20 | 0 | 0 | 0 | 10 | 0 | 0 | 10 | 20 |
| Nightshade | — | — | — | — | — | — | — | — | 60 | — | — | 40 | — | 30 |
| Nutsedge, Yellow | 0 | 0 | 0 | 0 | 0 | 0 | 0 | 0 | 0 | 0 | 0 | 0 | 0 | 0 |
| Oat, Wild | — | — | — | — | — | — | — | — | 0 | — | — | 0 | — | 0 |
| Oilseed Rape | 0 | 30 | 0 | 0 | 0 | 80 | 10 | 50 | 0 | 5 | 0 | 0 | 0 | 0 |
| Pigweed | 5 | 98 | 0 | 55 | 5 | 100 | 90 | 80 | — | 100 | 90 | — | 85 | — |
| Pigweed, Palmer | — | — | — | — | — | — | — | — | 40 | — | — | 70 | — | 75 |
| Poinsettia, Wild | — | — | — | — | — | — | — | — | 0 | — | — | 10 | — | 0 |
| Ragweed | 0 | 10 | 0 | 0 | 0 | 20 | 0 | 55 | 0 | 0 | 0 | 0 | 0 | 0 |
| Ryegrass, Italian | 0 | 0 | 0 | 0 | 0 | 35 | 0 | 0 | 0 | 10 | 30 | 0 | 0 | 0 |
| Soybean | 5 | 0 | 0 | 0 | 0 | — | 0 | 15 | — | 0 | 0 | 0 | 5 | 0 |
| Surinam Grass | — | — | — | — | — | — | — | — | 0 | — | — | 0 | — | 5 |
| Velvetleaf | 20 | 60 | 0 | 0 | 10 | 0 | 0 | 5 | 0 | 10 | 0 | 0 | 10 | 10 |
| Waterhemp | 80 | 90 | 10 | 30 | 70 | 100 | 85 | 100 | 50 | 100 | 65 | 75 | 95 | 100 |
| Wheat | 0 | 0 | 0 | 0 | 0 | 0 | 0 | 0 | 0 | 0 | 0 | 0 | 0 | 0 |
| Windgrass | — | — | — | — | — | — | — | — | 0 | — | — | 5 | — | 60 |

| 16 g ai/ha | Compounds | | | | | | | | | | |
|---|---|---|---|---|---|---|---|---|---|---|---|
| | 80 | 82 | 89 | 92 | 107 | 125 | 130 | 136 | 138 | 143 | 144 |
| | Preemergence | | | | | | | | | | |
| Barnyardgrass | 10 | 5 | 5 | 35 | 65 | — | — | — | 20 | — | 10 |
| Blackgrass | 5 | 0 | 5 | 45 | 60 | 5 | 30 | 0 | 10 | 5 | 5 |
| Corn | 0 | 0 | 0 | 0 | 0 | 0 | 5 | 0 | 0 | 5 | 0 |
| Crabgrass, Large | 55 | 60 | 75 | 100 | 98 | 35 | 98 | 50 | 75 | 70 | 85 |
| Foxtail, Giant | 5 | 20 | 0 | 100 | 60 | 30 | 50 | 25 | 35 | 20 | 70 |
| Galium | 0 | 0 | 0 | — | 5 | 0 | 0 | 0 | 0 | 0 | 0 |
| Johnsongrass | 5 | 0 | 0 | — | 10 | 5 | 10 | 10 | 0 | 5 | 0 |
| Kochia | 70 | 0 | 60 | — | 100 | 5 | 10 | 50 | 5 | 30 | 70 |
| Lambsquarters | 30 | 30 | 0 | 90 | 30 | 10 | 35 | 25 | 0 | 5 | 50 |
| Morningglory | 5 | 0 | 0 | 10 | 0 | 0 | 0 | 0 | 0 | 0 | 0 |

TABLE C-continued

| | | | | | | | | | | | |
|---|---|---|---|---|---|---|---|---|---|---|---|
| Nightshade | 55 | 5 | 10 | — | 30 | — | — | — | 40 | — | 35 |
| Nutsedge, Yellow | 0 | 0 | 0 | 0 | 0 | 0 | 5 | 0 | 0 | 0 | 0 |
| Oat, Wild | 0 | 0 | 5 | — | 0 | 5 | 0 | 0 | 0 | 0 | 0 |
| Oilseed Rape | 35 | 0 | 0 | 85 | 5 | 0 | 0 | 5 | 0 | 0 | 0 |
| Pigweed | — | — | — | 100 | — | — | — | — | — | — | — |
| Pigweed, Palmer | 100 | 55 | 65 | — | 100 | 90 | 85 | 95 | 40 | 65 | 85 |
| Poinsettia, Wild | 5 | 0 | 0 | — | 0 | 0 | 0 | 0 | 0 | 5 | 0 |
| Ragweed | 0 | 0 | 0 | 30 | 0 | 0 | 0 | 0 | 0 | 0 | 0 |
| Ryegrass, Italian | 0 | 0 | 0 | 5 | 10 | 0 | 15 | 5 | 0 | 5 | 0 |
| Soybean | 0 | 0 | 0 | 0 | 0 | 0 | 0 | 0 | 0 | 0 | 0 |
| Surinam Grass | 10 | 40 | 10 | — | 15 | 5 | 10 | 0 | 30 | 5 | 10 |
| Velvetleaf | 30 | 0 | 10 | 50 | 40 | 10 | 5 | 0 | 5 | 0 | 0 |
| Waterhemp | 95 | 60 | 70 | 100 | 100 | 70 | 50 | 65 | 75 | 85 | 98 |
| Wheat | 0 | 0 | 0 | 0 | 5 | 0 | 0 | 0 | 0 | 0 | 0 |
| Windgrass | 5 | 40 | 60 | — | 80 | 20 | 30 | 0 | 70 | 25 | 0 |

| 8 g ai/ha | Compound 13 | 4 g ai/ha | Compound 13 |
|---|---|---|---|
| Preemergence | | | |
| Barnyardgrass | 0 | Barnyardgrass | 0 |
| Blackgrass | 0 | Blackgrass | 0 |
| Corn | 0 | Corn | 0 |
| Crabgrass, Large | 30 | Crabgrass, Large | 25 |
| Foxtail, Giant | 0 | Foxtail, Giant | 0 |
| Lambsquarters | 5 | Lambsquarters | 0 |
| Morningglory | 0 | Morningglory | 0 |
| Nutsedge, Yellow | 0 | Nutsedge, Yellow | 0 |
| Oilseed Rape | 0 | Oilseed Rape | 0 |
| Pigweed | 10 | Pigweed | 5 |
| Ragweed | 0 | Ragweed | 0 |
| Ryegrass, Italian | 0 | Ryegrass, Italian | 0 |
| Soybean | 0 | Soybean | 0 |
| Velvetleaf | 10 | Velvetleaf | 5 |
| Waterhemp | 10 | Waterhemp | 5 |
| Wheat | 0 | Wheat | 0 |

| 250 g ai/ha | Compounds | | | | 125 g ai/ha | Compounds | | | | |
|---|---|---|---|---|---|---|---|---|---|---|
| | 61 | 66 | 92 | 119 | | 61 | 62 | 66 | 92 | 119 |
| Flood | | | | | | | | | | |
| Barnyardgrass | 40 | 80 | 40 | 25 | Barnyardgrass | 20 | 20 | 25 | 20 | 0 |
| Ducksalad | 90 | 95 | 100 | 50 | Ducksalad | 90 | 75 | 85 | 95 | 40 |
| Rice | 20 | 20 | 15 | 0 | Rice | 20 | 10 | 0 | 15 | 0 |
| Sedge, Umbrella | 85 | 95 | 100 | 90 | Sedge, Umbrella | 85 | 65 | 85 | 90 | 80 |

| 62 g ai/ha | Compounds | | | | 31 g ai/ha | Compounds | | | | |
|---|---|---|---|---|---|---|---|---|---|---|
| | 61 | 62 | 66 | 92 | 119 | | 61 | 62 | 66 | 92 | 119 |
| Flood | | | | | | | | | | |
| Barnyardgrass | 0 | 0 | 0 | 0 | 0 | Barnyardgrass | 0 | 0 | 0 | 0 | 0 |
| Ducksalad | 75 | 40 | 80 | 60 | 0 | Ducksalad | 50 | 0 | 40 | 30 | 0 |
| Rice | 20 | 0 | 0 | 15 | 0 | Rice | 20 | 0 | 0 | 10 | 0 |
| Sedge, Umbrella | 80 | 60 | 75 | 60 | 55 | Sedge, Umbrella | 80 | 0 | 40 | 20 | 0 |

| 16 g ai/ha | Compound 62 |
|---|---|
| Flood | |
| Barnyardgrass | 0 |
| Ducksalad | 0 |
| Rice | 0 |
| Sedge, Umbrella | 0 |

What is claimed is:

1. A compound selected from Formula 1, N-oxides and salts thereof,

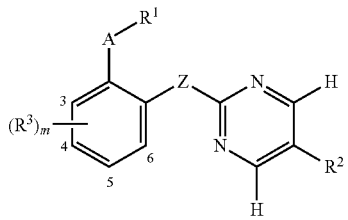

wherein

A is

   A-3

B is O or S;
R$^1$ is C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_3$-C$_6$ alkenyloxy, C$_3$-C$_6$ alkynyloxy, C$_1$-C$_6$ haloalkoxy, C$_3$-C$_6$ haloalkenyloxy, C$_3$-C$_6$ cycloalkoxy, C$_4$-C$_8$ cycloalkylalkoxy, C$_2$-C$_6$ cyanoalkyl, C$_2$-C$_6$ cyanoalkoxy, C$_1$-C$_6$ alkylthio, C$_1$-C$_6$ haloalkylthio or C$_1$-C$_6$ alkenylthio;
Z is O;
R$^2$ is halogen;
each R$^3$ is independently halogen, cyano, CHO, C(=O)NH$_2$, C(=S)NH$_2$, SO$_2$NH$_2$, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_3$-C$_6$ cycloalkyl, C$_3$-C$_6$ halocycloalkyl, C$_4$-C$_8$ alkylcycloalkyl, C$_4$-C$_8$ cycloalkylalkyl, C$_2$-C$_6$ alkylcarbonyl, C$_2$-C$_6$ haloalkylcarbonyl, C$_2$-C$_6$ alkoxycarbonyl, C$_3$-C$_7$ cycloalkylcarbonyl, C$_2$-C$_4$ alkoxy, C$_3$-C$_4$ alkenyloxy, C$_3$-C$_4$ alkynyloxy, C$_1$-C$_4$ haloalkoxy, C$_3$-C$_6$ cycloalkoxy, C$_3$-C$_6$ halocycloalkoxy, C$_4$-C$_8$ cycloalkylalkoxy, C$_2$-C$_6$ alkoxyalkyl, C$_2$-C$_6$ haloalkoxyalkyl, C$_2$-C$_6$ alkoxyhaloalkyl, C$_2$-C$_6$ alkoxyalkoxy, C$_2$-C$_4$ alkylcarbonyloxy, C$_2$-C$_6$ cyanoalkyl, C$_2$-C$_6$ cyanoalkoxy, C$_2$-C$_4$ alkylthioalkyl, —C(=O)N(R$^{11a}$)(R$^{11b}$), —C(=NOR$^{12}$)H, —C(=N(R$^{13}$))H or —SO—R$^{14}$;
m is 0, 1, 2 or 3;
each n is independently 0, 1 or 2;
each R$^{11a}$ is independently C$_1$-C$_4$ alkyl or C$_1$-C$_4$ haloalkyl;
each R$^{11b}$ is independently H, C$_1$-C$_4$ alkyl or C$_1$-C$_4$ haloalkyl;
each R$^{12}$ is independently H or C$_1$-C$_4$ alkyl;
each R$^{13}$ is independently H, amino, C$_1$-C$_4$ alkyl or C$_1$-C$_4$ alkylamino; and
each R$^{14}$ is independently C$_1$-C$_6$ alkyl, C$_1$-C$_6$ haloalkyl, C$_1$-C$_6$ alkylamino or C$_2$-C$_{10}$ dialkylamino;
provided that the compound of Formula 1 is other than methyl 2-[(5-chloro-2-pyrimidinyl)oxy]benzoate, methyl 2-[(5-bromo-2-pyrimidinyl)oxy]benzoate and 1-[2-[(5-bromo-2-pyrimidinyl)oxy]phenyl]-ethanone.

2. The compound of claim 1 wherein
R$^1$ is C$_1$-C$_6$ alkyl, C$_2$-C$_6$ alkenyl, C$_1$-C$_6$ haloalkyl, C$_1$-C$_6$ alkoxy or C$_1$-C$_6$ haloalkoxy;
R$^2$ is F, Cl or Br;
each R$^3$ is independently halogen, cyano, C$_1$-C$_4$ alkyl or C$_1$-C$_4$ haloalkyl; and
m is 1 or 2.

3. The compound of claim 2 wherein
B is O;
R$^1$ is C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_3$-C$_6$ alkenyloxy, C$_3$-C$_6$ alkynyloxy, C$_1$-C$_6$ haloalkoxy, C$_3$-C$_6$ haloalkenyloxy, C$_2$-C$_6$ cyanoalkyl, C$_2$-C$_6$ cyanoalkoxy, C$_1$-C$_6$ alkylthio, C$_1$-C$_6$ haloalkylthio or C$_1$-C$_6$ alkenylthio;
R$^2$ is Cl;
each R$^3$ is independently halogen, cyano, C$_1$-C$_3$ alkyl or C$_1$-C$_3$ haloalkyl; and
m is 1 or 2.

4. The compound of claim 2 wherein
B is O;
R$^1$ is C$_1$-C$_6$ alkyl, C$_1$-C$_6$ haloalkyl, C$_1$-C$_6$ alkoxy or C$_1$-C$_6$ haloalkoxy;
R$^2$ is F, Cl or Br;
each R$^3$ is independently halogen, cyano, C$_1$-C$_3$ alkyl or C$_1$-C$_3$ haloalkyl; and
m is 1 or 2.

5. The compound of claim 2 wherein
B is O;
R$^1$ is C$_1$-C$_6$ haloalkyl;
R$^2$ is Cl;
each R$^3$ is independently halogen, cyano, C$_1$-C$_3$ alkyl or C$_1$-C$_3$ haloalkyl; and
m is 1 or 2.

6. The compound of claim 1 selected from the group consisting of
3,3,3-trifluoropropyl 2-chloro-6-[(5-chloro-2-pyrimidinyl)oxy]benzoate;
3,3,3-trifluoro-1-methylpropyl 2-bromo-6-[(5-chloro-2-pyrimidinyl)oxy]benzoate;
propyl 2-bromo-6-[(5-chloro-2-pyrimidinyl)oxy]benzoate;
4,4,4-trifluorobutyl 2-bromo-6-[(5-chloro-2-pyrimidinyl)oxy]benzoate;
2-propen-1-yl 2-bromo-6-[(5-chloro-2-pyrimidinyl)oxy]benzoate;
3-buten-1-yl 2-bromo-6-[(5-chloro-2-pyrimidinyl)oxy]benzoate;
2,2,3,3,3-pentafluoropropyl 2-bromo-6-[(5-chloro-2-pyrimidinyl)oxy]benzoate;
3,3,3-trifluoropropyl 2-bromo-6-[(5-chloro-2-pyrimidinyl)oxy]benzoate; and
1-[2-chloro-6-[(5-chloro-2-pyrimidinyl)oxy]phenyl]-4,4,4-trifluoro-1-butanone.

7. The compound of claim 1 wherein
R$^1$ is C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_3$-C$_6$ alkenyloxy, C$_3$-C$_6$ alkynyloxy, C$_1$-C$_6$ haloalkoxy, C$_3$-C$_6$ haloalkenyloxy, C$_3$-C$_6$ cycloalkoxy, C$_4$-C$_5$ cycloalkylalkoxy, C$_2$-C$_6$ cyanoalkyl, C$_2$-C$_6$ cyanoalkoxy, C$_1$-C$_6$ alkylthio, C$_1$-C$_6$ haloalkylthio or C$_1$-C$_6$ alkenylthio;
R$^2$ is halogen;
each R$^3$ is independently halogen, cyano, CHO, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_3$-C$_6$ cycloalkyl, C$_3$-C$_6$ halocycloalkyl, C$_4$-C$_6$ alkylcycloalkyl, C$_2$-C$_6$ alkylcarbonyl, C$_2$-C$_6$ haloalkylcarbonyl, C$_2$-C$_6$ alkoxycarbonyl, C$_1$-C$_4$ alkoxy, C$_3$-C$_4$ alkenyloxy, C$_3$-C$_4$ alkynyloxy, C$_1$-C$_4$ haloalkoxy, C$_3$-C$_4$ haloalkenyloxy, $C_3$-$C_4$ haloalkynyloxy, $C_3$-$C_6$ cycloalkoxy, $C_3$-$C_6$ halocycloalkoxy, $C_2$-$C_6$ alkoxyalkyl, $C_2$-$C_6$ haloalkoxyalkyl, $C_2$-$C_4$ alkylcarbonyloxy, $C_2$-$C_6$ cyanoalkyl, —C(=O)N($R^{11a}R^{11b}$), —C(=NO$R^{12}$)H or —SO$_n R^{14}$;

$R^{11a}$ is $C_1$-$C_2$ alkyl or $C_1$-$C_2$ haloalkyl;
$R^{11b}$ is $C_1$-$C_2$ alkyl or $C_1$-$C_2$ haloalkyl;
$R^{12}$ is H or $C_1$-$C_3$ alkyl; and
$R^{14}$ is $C_1$-$C_3$ alkyl or $C_1$-$C_3$ haloalkyl.

8. The compound of claim 1 that is 1-[2-chloro-6-[(5-chloro-2-pyrimidinyl)oxy]phenyl]-4,4,4-trifluoro-1-butanone.

9. A herbicidal composition comprising a compound of claim 1 and at least one component selected from the group consisting of surfactants, solid diluents and liquid diluents.

10. A herbicidal composition comprising a compound of claim 1, at least one additional active ingredient selected from the group consisting of other herbicides and herbicide safeners, and at least one component selected from the group consisting of surfactants, solid diluents and liquid diluents.

11. The herbicidal composition of claim 10 wherein the at least one additional active ingredient is selected from the group consisting of (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solanesyltransferase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, (b16) herbicide safeners, and salts of compounds of (b1) through (b16).

12. The herbicidal composition of claim 10 wherein the at least one additional active ingredient is selected from the group consisting of (b1) photosystem II inhibitors, (b2) acetohydroxy acid synthase (AHAS) inhibitors, (b4) auxin mimics, (b5) 5-enol-pyruvylshikimate-3-phosphate (EPSP) synthase inhibitors, (b7) protoporphyrinogen oxidase (PPO) inhibitors, (b9) very long chain fatty acid (VLCFA) elongase inhibitors and (b12) 4-hydroxyphenyl-pyruvate dioxygenase (HPPD) inhibitors.

13. The herbicidal composition of claim 10 wherein the at least one additional active ingredient is selected from the group consisting of 2,4-D, acetochlor, alachlor, atrazine, bromoxynil, bentazon, bicyclopyrone, carfentrazone-ethyl, cloransulam-methyl, dicamba, dimethenamid-p, florasulam, flufenacet, flumioxazin, flupyrsulfuron-methyl, fluroxypyr-meptyl, glyphosate, halauxifen-methyl, isoxaflutole, MCPA, mesotrione, metolachlor, metsulfuron-methyl, nicosulfuron, pyrasulfotole, pyroxasulfone, pyroxsulam, rimsulfuron, saflufenacil, tembotrione, thifensulfuron-methyl, topramazone and tribenuron.

14. The herbicidal composition of claim 10 wherein the at least one additional active ingredient comprises glyphosate.

15. A method for controlling the growth of undesired vegetation comprising contacting the vegetation or its environment with a herbicidally effective amount of a compound of claim 1.

16. A method for controlling the growth of undesired vegetation in genetically modified plants that exhibit traits of glyphosate tolerance, glufosinate tolerance, ALS herbicide tolerance, dicamba tolerance, imidazolinone herbicide tolerance, 2,4-D tolerance, HPPD tolerance and mesotrione tolerance, comprising contacting the vegetation or its environment with a herbicidally effective amount of a compound of claim 1.

* * * * *